United States Patent [19]

Belanger et al.

[11] Patent Number: 5,091,533

[45] Date of Patent: Feb. 25, 1992

[54] 5-HYDROXY-2,3-DIHYDROBENZOFURAN ANALOGS AS LEUKOTRIENE BIOSYNTHESIS INHIBITORS

[75] Inventors: Patrice C. Belanger; Claude Dufresne, both of Dollard des Ormeaux; Brian Fitzsimmons, deceased, late of Pierrefondf; Maryann Fitzsimmons, Heir, Pierrefondf; Yvan Guindon, Montreal; Cheuk K. Lau, Bizzard, all of Canada; Joshua Rokach, Satellite Beach, Fla.; John Schiegetz, Dollard des Ormeaux, Canada; Michel Therien, Laval, Canada; Robert N. Young, Senneville, Canada

[73] Assignee: Merck Frosst Canada, Inc., Kirkland, Canada

[21] Appl. No.: 491,799

[22] Filed: Mar. 12, 1990

[51] Int. Cl.[5] ............... A61K 31/34; C07D 307/79
[52] U.S. Cl. .................... 544/318; 544/235; 544/286; 544/338; 544/405; 546/141; 546/152; 546/156; 546/157; 546/170; 546/262; 548/182; 548/221; 548/327; 548/371; 548/372; 548/469; 548/486; 549/28; 549/58; 549/273; 549/292; 549/294; 549/414; 549/462; 549/470
[58] Field of Search ............... 549/462, 470, 28, 60, 549/273, 292, 414; 544/235, 238, 286, 318, 405; 546/141, 152, 156, 157, 170, 262; 548/252, 182, 221, 225, 263, 327, 336, 371, 372, 469, 486, 525

[56] References Cited

U.S. PATENT DOCUMENTS

| | | | |
|---|---|---|---|
| 4,537,903 | 7/1985 | Chang et al. | 514/456 |
| 4,558,067 | 12/1985 | Thompson et al. | 514/458 |
| 4,563,476 | 1/1986 | Chang et al. | 514/459 |
| 4,686,235 | 8/1987 | Chang et al. | 514/520 |
| 4,713,393 | 12/1987 | Chang et al. | 514/469 |
| 4,857,516 | 8/1989 | Terao et al. | 514/100 |
| 4,978,761 | 12/1990 | Goto et al. | 549/470 |

FOREIGN PATENT DOCUMENTS 0273647 7/1988 European Pat. Off. .
0345593 12/1989 European Pat. Off. .

OTHER PUBLICATIONS

Alabaster et al., Synthesis, 589-603 (1989).
Baker et al., J. Chem. Soc., Chem. Comm., 1102-1104 (1987).
Iwamoto, H., J. Org. Chem, 53, pp. 1507-1515 (1988).
Maruyma, K. et al. Chem Lett., pp. 1343-1346 (1984).
Belanger, P. et al., Can. J. Physiol. Pharmacol. vol. 65, pp. 2441-2448.
Ogiso, A., et al., Chem. Pharm. Bull. 18 (1) pp. 105-114 (1979).

*Primary Examiner*—Bernard Dentz
*Attorney, Agent, or Firm*—Gabriel Lopez; John W. Harbour; Joseph F. DiPrima

[57] ABSTRACT

Compounds of the formula:

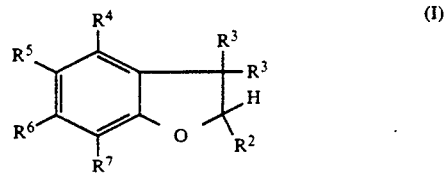

where $R^2$ contains certain aryls or heteroaryls are effective leukotriene inhibitors.

24 Claims, No Drawings

5-HYDROXY-2,3-DIHYDROBENZOFURAN ANALOGS AS LEUKOTRIENE BIOSYNTHESIS INHIBITORS

BACKGROUND OF THE INVENTION

This invention involves certain benzofuran derivatives. These compounds are useful as inhibitors of mammalian leukotriene biosynthesis. As such, these compounds are useful therapeutic agents for treating allergic conditions, asthma, cardiovascular disorders and inflammation. The compounds are also useful as analgesics and as cytoprotective agents.

The leukotrienes are a novel group of biologically active mediators derived from arachidonic acid through the action of lipoxgenase enzyme systems. There are two groups of leukotrienes derived from the common unstable precursor Leukotriene A4. The first of these are the peptido-lipid leukotrienes, the most important being Leukotrienes C4 and D4. These compounds collectively account for the biologically active material known as the slow reacting substance of anaphylaxis.

The leukotrienes are potent smooth muscle contracting agents, particularly on respiratory smooth muscle but also on other tissues (e.g. gall bladder). In addition, they promote mucous production, modulate vascular permeability changes and are potent inflammatory agents in human skin. The most important compound in the second group of leukotrienes is Leukotriene B4, a dihydroxy fatty acid. This compound is a potent chemotactic agent for neutrophils and eosinophils and in addition, may modulate a number of other functions of these cells. It also affects other cell types such as lymphocytes and, for example, may modulate the action of T-suppressor cells and natural killer cells. When injected in vivo, in addition to promoting the accumulation of leukocytes, Leukotriene B4 is also a potent hyperalgesic agent and can modulate vascular permeability changes through a neutrophil dependent mechanism. Both groups of leukotrienes are formed following oxygenation of arachidonic acid through the action of a 5-lipoxygenase enzyme. See for example, D. M. Bailey et al., *Ann. Rpts. Med. Chem.* 17 203 (1982).

The leukotrienes are potent spasmogens of human trachea, bronchus and lung parenchymal strips, and when administered to normal volunteers as aerosols are 3,800 times more potent that histamine at inducing a 50% decrease in air flow at 30% of vital capacity. They mediate increases in vascular permeability in animals and promote mucous production in human bronchial explants. In addition, Leukotriene B4 may also mediate mucous production and could be an important mediator of neutrophil and eosinophil accumulation in asthmatic lungs. 5-lipoxygenase products are also thought to be regulators of mast cell degranulation and recent studies with human lung mast cells have suggested that 5-lipoxygenase inhibitors, but not corticosteroids, may suppress antigen-induced mast cell degranulation. In vitro studies have shown that antigen challenge of human lung results in the release of leukotrienes and in addition purified human mast cells can produce substantial amount of leukotrienes. There is therefore good evidence that leukotrienes are important mediators of human asthma. 5-lipoxygenase inhibitors would therefore be a new class of drugs for the treatment of asthma. See, for example, B. Samuelson, *Science* 220, 568–575 (1983).

Psoriasis is a human skin disease which affects between two and six percent of the population. There is no adequate therapy for psoriasis and related skin conditions. The evidence for leukotriene involvement in these diseases is as follows. One of the earliest events in the development of prepapillary lesions is the recruitment of leukocytes to the skin site. Injection of Leukotriene B4 into human skin results in a pronounced neutrophil accumulation. These are gross abnormalities in arachidonic acid metabolism in human psoriatic skin. In particular, highly elevated levels of free arachidonic acid can be measured as well as large amounts of lipoxygenase products. Leukotriene B4 has been detected in biologically significant amounts in psoriatic lesions, but not in uninvolved skin.

Leukotrienes can be measured in nasal washings from patients with allergic rhinitis and are greatly elevated following antigen challenge. Leukotrienes may mediate this disease through their ability to regulate mast cell degranulation, by modulating mucous production and mucocillary clearance and by mediating the accumulation of inflammatory leukocytes.

Leukotrienes can also mediate other diseases. These include atopic dermatitis, gouty arthritis, inflammatory bowel diseases and gall bladder spasms. In addition, they may have a role in cardiovasular disease because leukotrienes C4 and D4 act as coronary and cerebral arterial vasoconstrictors and these compounds may also have negative inotropic effects on the myocardium. In addition, the leukotrienes are important mediators of inflammatory diseases through their ability to modulate leukocyte and lymphocyte function.

SUMMARY OF THE INVENTION

It has now been discovered that certain 5-hydroxy-2,3-dihydrobenzofuran analogs of Formula I are effective inhibitors of leukotriene biosynthesis. Thus, these compounds are useful therapeutic agents for treating conditions such as asthma, allergies, cardiovascular disorders such as angina and inflammation, for amelioration of skin diseases like psoriasis and atopic eczema, and as cytoprotective agents.

The compounds of the present invention are compounds of the general formula:

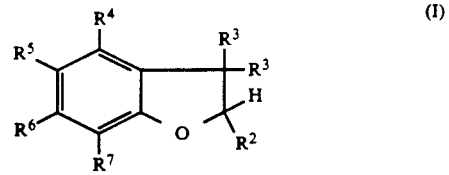

wherein:
$R^2$ is

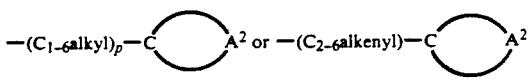

with $A^2$ completing a ring selected from the group consisting of $(Y^6)_5$ substituted phenyl, $(Y^6)_7$ substituted naphthyl, substituted or unsubstituted 5-membered heterocycle, substituted or unsubstituted 6-membered heterocycle, substituted or unsubstituted 5-membered heterocycle having fused thereto a $(Y^2)_{3or4}$ substituted benzene ring and substituted or unsubstituted 6-membered heterocycle having fused thereto a (Y²)₃ₒᵣ₄ substituted benzene ring (where the heterocycle contains 1 to 4 heteroatoms, including 0 to 1 in total of —O—, —S—, —NH— or —N(C₁₋₄alkyl)— and 0 to 3 of nitrogen the valence of which is satisfied by the ring, and where the heterocycle substituents are selected from the group consisting of hydrogen, C₁₋₆alkyl, phenyl, halogen, —C(O)OH, —C(O)OC₁₋₆alkyl and —OC₁₋₆alkyl);

R³ is independently, hydrogen or C₁₋₆alkyl;
R⁵ is hydroxy or metabolizeable to hydroxy;
R⁴ and R⁶ are, independently hydrogen, halogen, —C₁₋₆alkyl, C₂₋₆alkenyl, —(C₁₋₆alkyl)—R⁶ᵃ, —(C₂₋₆alkenyl)—R⁶ᵃ, —(C₁₋₆alkyl)ₚ—OR⁶ᵇ, —(C₂₋₆alkenyl)—OR⁶ᵇ, —(C₁₋₆alkyl)ₚ—SR⁶ᵇ, —(C₂₋₆alkenyl)—SR⁶ᵇ, —(C₁₋₆alkyl)ₚ—S(O)R⁶ᵇ, —(C₂₋₆alkenyl)—S(O)R⁶ᵇ, —(C₁₋₆alkyl)ₚ—S(O)₂R⁶ᵇ, —(C₂₋₆alkenyl)S(O)₂R⁶ᵇ, —(C₁₋₆alkyl)ₚ—N(R⁶ᶜ)(R⁶ᵇ) or —(C₂₋₆alkenyl)—N(R⁶ᶜ)(R⁶ᵇ), provided that when one of R⁴ or R⁶ is hydrogen or halogen then the other is not hydrogen or halogen and provided that R⁶ is not —C₁₋₆alkyl or —O—C₁₋₆alkyl when R⁴ is —C₁₋₆alkyl;
R⁷ is hydrogen, halogen, C₁₋₆alkyl or C₂₋₆alkenyl;
R⁶ᵃ is (Y⁶)₅ substituted phenyl, (Y⁶)₇ substituted naphthyl, —C(O)NR⁶ᶜ, —C(O)OR⁶ᶜ, or

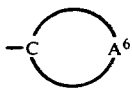

where A⁶ completes a substituted or unsubstituted 5-membered heterocycle, substituted or unsubstituted 6-membered heterocycle, substituted or unsubstituted 5-membered heterocycle having fused thereto a (Y²)₃ₒᵣ₄ substituted benzene ring, or a substituted or unsubstituted 6-membered heterocycle having fused thereto a (Y²)₃ₒᵣ₄ substituted benzene ring (where heterocycle and heterocycle substitution are defined above);
R⁶ᵇ is hydrogen, C₁₋₆alkyl, C₂₋₆alkenyl, —(C₁₋₆alkyl)ₚ—((Y⁶)₇ substituted naphthyl), —(C₁₋₆alkyl)ₚ—((Y⁶)₅ substituted phenyl), —(C₁₋₆alkyl)—C(O)N(R⁶ᶜ)₂, —(C₁₋₆alkyl)—C(O)OR⁶ᶜ or

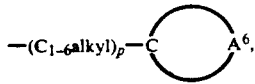

(where A⁶ is defined immediately above and R⁶ᵇ is not hydrogen when attached to sulfur);
R⁶ᶜ is hydrogen or C₁₋₆alkyl;
Y² is —H, halogen, —OH, C₁₋₆alkyl, —CN, —CF₃, —(C₁₋₆alkyl)ₚ—O—C₁₋₆alkyl, —(C₁₋₆alkyl)ₚ—S—C₁₋₆alkyl, —(C₁₋₆alkyl)ₚ—S(O)—C₁₋₆alkyl, —(C₁₋₆alkyl)ₚ—S(O)₂—C₁₋₆alkyl, —(C₁₋₆alkyl)ₚ—C(O)—C₁₋₆alkyl, —O—(C₁₋₆alkyl)ₚ—C(O)OR⁶ᶜ, —(C₁₋₆alkyl)ₚ—C(O)OR⁶ᶜ, —(C₁₋₆alkyl)ₚ—C(O)NHOR⁶ᶜ, —(C₁₋₆alkyl)ₚ—C(O)NHR⁶ᶜ, —(C₁₋₆alkyl)ₚ—NHC(O)O(C₁₋₆alkyl), —(C₁₋₆alkyl)ₚ—NHR⁶ᶜ, —(C₁₋₆alkyl)ₚ—NHS(O)₂—C₁₋₆alkyl, —(C₁₋₆alkyl)ₚ—NHS(O)₂—(R⁷)₅ substituted phenyl, or —(C₁₋₆alkyl)ₚ—NO₂;
Y⁶ is Y² or

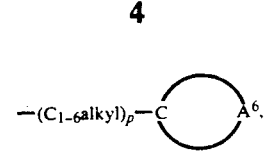

(where A⁶ is defined immediately above); and
p is 0 or 1.
Preferred compounds of formula I are those in which:
R² is —(C₁₋₆alkyl)ₚ—(Y⁶)₅ substituted phenyl or —(C₂₋₆alkenyl)—(Y⁶)₅ substituted phenyl;
R³ is independently hydrogen or C₁₋₆alkyl;
R⁵ is hydroxy or metabolizeable to hydroxy:
R⁴ is hydrogen, halogen, —C₁₋₆alkyl, C₂₋₆alkenyl, —(C₁₋₆alkyl)—R⁶ᵃ, —(C₂₋₆alkenyl)—R⁶ᵃ, —(C₁₋₆alkyl)ₚ—OR⁶ᵇ, —(C₂₋₆alkenyl)—OR⁶ᵇ, —(C₁₋₆alkyl)ₚ—SR⁶ᵇ, —(C₂₋₆alkenyl)—SR⁶ᵇ, —(C₁₋₆alkyl)ₚ—S(O)R⁶ᵇ, —(C₂₋₆alkenyl)—S(O)R⁶ᵇ, —(C₁₋₆alkyl)ₚ—S(O)₂R⁶ᵇ, —(C₂₋₆alkenyl)—S(O)₂R⁶ᵇ, —(C₁₋₆alkyl)ₚ—N(R⁶ᶜ)(R⁶ᵇ) or —(C₂₋₆alkenyl)—N(R⁶ᶜ)(R⁶ᵇ);
R⁶ is —(C₁₋₆alkyl)—R⁶ᵃ, —(C₂₋₆alkenyl)—R⁶ᵃ, —(C₁₋₆alkyl)ₚ—OR⁶ᵇ, —(C₂₋₆alkenyl)—OR⁶ᵇ, —(C₁₋₆alkyl)ₚ—SR⁶ᵇ, —(C₂₋₆alkenyl)—SR⁶ᵇ, —(C₁₋₆alkyl)ₚ—S(O)R⁶ᵇ, —(C₂₋₆alkenyl)—S(O)R⁶ᵇ, —(C₁₋₆alkyl)ₚ—S(O)₂R⁶ᵇ or —(C₂₋₆alkenyl)—S(O)₂R⁶ᵇ;
R⁷ is hydrogen, halogen, C₁₋₆alkyl or C₂₋₆alkenyl;
R⁶ᵃ is (Y⁶)₅ substituted phenyl, (Y⁶)₇ substituted naphthyl, —C(O)NR⁶ᶜ, —C(O)OR⁶ᶜ, or

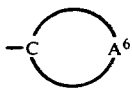

where A⁶ completes a substituted or unsubstituted 5-membered heterocycle, substituted or unsubstituted 6-membered heterocycle, substituted or unsubstituted 5-membered heterocycle having fused thereto a (Y²)₃ₒᵣ₄ substituted benzene ring, or a substituted or unsubstituted 6-membered heterocycle having fused thereto a (Y²)₃ₒᵣ₄ substituted benzene ring (where the heterocycle contains 1 to 4 heteroatoms, including 0 to 1 in total of —O—, —S—, —NH— or —N(C₁₋₄alkyl)— and 0 to 3 of nitrogen the valence of which is satisfied by the ring, and where the heterocycle substituents are selected from the group consisting of hydrogen, C₁₋₆alkyl, phenyl, halogen, —C(O)OH, —C(O)OC₁₋₆alkyl and —OC₁₋₆alkyl);
R⁶ᵇ is —(C₁₋₆alkyl)ₚ—((Y⁶)₇ substituted naphthyl), —(C₁₋₆alkyl)ₚ—((Y⁶)₅ substituted phenyl), —(C₁₋₆alkyl)—C(O)N(R⁶ᶜ)₂, —(C₁₋₆alkyl)—C(O)OR⁶ᶜ or

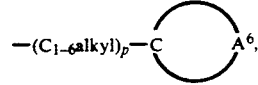

(where A⁶ is defined immediately above);
R⁶ᶜ is hydrogen or C₁₋₆alkyl;
Y² is —H, halogen, —OH, C₁₋₆alkyl, —CN, —CF₃, —(C₁₋₆alkyl)ₚ—O—C₁₋₆alkyl, —(C₁₋₆alkyl)ₚ—S—C₁₋₆alkyl, —(C₁₋₆alkyl)ₚ—S(O)—C₁₋₆alkyl, —(C₁₋₆alkyl)ₚ—S(O)₂—C₁₋₆alkyl, —O—(C₁₋₆alkyl)ₚ—C(O)OR⁶ᶜ, —(C₁₋₆alkyl)ₚ—C(O)OR⁶ᶜ, —(C₁₋₆alkyl)ₚ—C(O)NHOR⁶ᶜ, —(C₁₋₆alkyl)ₚ—C-

(O)NHR$^{6c}$, —(C$_{1-6}$alkyl)$_p$—NHC(O)O(C$_{1-6}$alkyl), —(C$_{1-6}$alkyl)$_p$—NHS(O)$_2$—C$_{1-6}$alkyl, —(C$_{1-6}$alkyl)$_p$—NHS(O)$_2$—(R$^7$)$_5$ substituted phenyl, or —(C$_{1-6}$alkyl)$_p$—NO$_2$;

Y$^6$ is Y$^2$ or

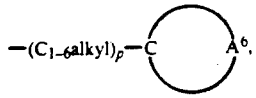

(where A$^6$ is defined immediately above); and
p is 0 or 1.

Still more preferred compounds of formula I are those in which:

R$^2$ is —(C$_{1-6}$alkyl)$_p$—(Y$^6$)$_5$ substituted phenyl or —(C$_{2-6}$alkenyl)—(Y$^6$)$_5$ substituted phenyl;

R$^3$ is independently hydrogen or C$_{1-6}$alkyl;

R$^5$ is hydroxy or metabolizeable to hydroxy;

R$^4$ is hydrogen, halogen, —C$_{1-6}$alkyl, C$_{2-6}$alkenyl, —(C$_{1-6}$alkyl)—R$^{6a}$, —(C$_{2-6}$alkenyl)—R$^{6a}$, —(C$_{1-6}$alkyl)$_p$—OR$^{6b}$, —(C$_{2-6}$alkenyl)—OR$^{6b}$, —(C$_{1-6}$alkyl)$_p$—SR$^{6b}$, —(C$_{2-6}$alkenyl)—SR$^{6b}$, —(C$_{1-6}$alkyl)$_p$—S(O)R$^{6b}$, —(C$_{2-6}$alkenyl)—S(O)R$^{6b}$, —(C$_{1-6}$alkyl)$_p$—S(O)$_2$R$^{6b}$, —(C$_{2-6}$alkenyl)-S(O)$_2$R$^{6b}$, —(C$_{1-6}$alkyl)$_p$—N(R$^{6c}$)(R$^{6b}$) or —(C$_{2-6}$alkenyl)—N(R$^{6c}$)(R$^{6b}$);

R$^6$ is —(C$_{1-6}$alkyl)—R$^{6a}$, —(C$_{2-6}$alkenyl)—R$^{6a}$, —(C$_{1-6}$alkyl)$_p$—OR$^{6b}$, —(C$_{2-6}$alkenyl)—OR$^{6b}$, —(C$_{1-6}$alkyl)$_p$—SR$^{6b}$, —(C$_{2-6}$alkenyl)—SR$^{6b}$, —(C$_{1-6}$alkyl)$_p$—S(O)R$^{6b}$, —(C$_{2-6}$alkenyl)—S(O)R$^{6b}$, —(C$_{1-6}$alkyl)$_p$—S(O)$_2$R$^{6b}$ or —(C$_{2-6}$alkenyl)—S(O)$_2$R$^{6b}$;

R$^7$ is hydrogen or halogen;

R$^{6a}$ is (Y$^6$)$_5$ substituted phenyl, —C(O)OR$^{6c}$, or

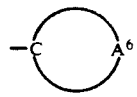

where A$^6$ completes substituted or unsubstituted 6-membered heterocycle, or a substituted or unsubstituted 6-membered heterocycle having fused thereto a (Y$^2$)$_{3or4}$ substituted benzene ring (where the heterocycle contains 1 to 4 heteroatoms, including 0 to 1 in total of —O—, —S—, —NH— or —N(C$_{1-4}$alkyl)— and 0 to 3 of nitrogen the valence of which is satisfied by the ring, and where the heterocycle substituents are selected from the group consisting of hydrogen, C$_{1-6}$alkyl, phenyl, halogen, —C(O)OH, —C(O)OC$_{1-6}$alkyl and —OC$_{1-6}$alkyl);

R$^{6b}$ is —(C$_{1-6}$alkyl)$_p$—((Y$^6$)$_5$ substituted phenyl), —(C$_{1-6}$alkyl)—C(O)OR$^{6c}$, or

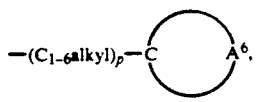

(where A$^6$ is defined immediately above);

R$^{6c}$ is hydrogen or C$_{1-6}$alkyl;

Y$^2$ is —H, halogen, —OH, C$_{1-6}$alkyl, —CN, —CF$_3$, —(C$_{1-6}$alkyl)$_p$—O—C$_{1-6}$alkyl, —(C$_{1-6}$alkyl)$_p$—S—C$_{1-6}$alkyl, —(C$_{1-6}$alkyl)$_p$—S(O)—C$_{1-6}$alkyl, —(C$_{1-6}$alkyl)$_p$—S(O)$_2$—C$_{1-6}$alkyl, —O—(C$_{1-6}$alkyl)$_p$—C(O)OR$^{6c}$, —(C$_{1-6}$alkyl)$_p$—C(O)OR$^{6c}$, —(C$_{1-6}$alkyl)$_p$—C(O)NHOH, —(C$_{1-6}$alkyl)$_p$—C(O)NHR$^{6c}$ or —(C$_{1-6}$alkyl)$_p$—NHS(O)$_2$—(R$^7$)$_5$ substituted phenyl;

Y$^6$ is Y$^2$ or

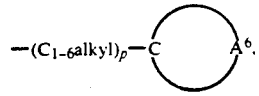

(where A$^6$ is defined immediately above); and
p is 0 or 1.

The most preferred compounds of Formula I are those in which:

R$^2$ is —(C$_{1-6}$alkyl)—(Y$^6$)$_5$ substituted phenyl or —(C$_{2-6}$alkenyl)—(Y$^6$)$_5$ substituted phenyl;

R$^3$ is independently hydrogen or C$_{1-6}$alkyl;

R$^4$ is hydrogen, halogen, —C$_{1-6}$alkyl, C$_{2-6}$alkenyl, —(C$_{1-6}$alkyl)—R$^{6a}$, —(C$_{2-6}$alkenyl)—R$^{6a}$, —(C$_{1-6}$alkyl)$_p$—OR$^{6b}$, —(C$_{2-6}$alkenyl)—OR$^{6b}$, —(C$_{1-6}$alkyl)$_p$—SR$^{6b}$, —(C$_{2-6}$alkenyl)—SR$^{6b}$, —(C$_{1-6}$alkyl)$_p$—S(O)R$^{6b}$, —(C$_{2-6}$alkenyl)—S(O)R$^{6b}$, —(C$_{1-6}$alkyl)$_p$—S(O)$_2$R$^{6b}$, —(C$_{2-6}$alkenyl)-S(O)$_2$R$^{6b}$, —(C$_{1-6}$alkyl)$_p$—N(R$^{6c}$)(R$^{6b}$) or —(C$_{2-6}$alkenyl)—N(R$^{6c}$)(R$^{6b}$);

R$^5$ is hydrogen, —OC(O)—(C$_{1-6}$alkyl), —OC(O)O—(C$_{1-6}$alkyl), —OC(O)O—(phenyl), —OC(O)—(phenyl), —OSO$_3$NH$_4$, —OC(O)NR$_2'$, —O-(O)P(OH)$_2$ or —OC(O)—(C$_{1-6}$alkyl)—COOR' where R' is hydrogen, C$_{1-6}$alkyl or phenyl;

R$^6$ is —(C$_{1-6}$alkyl)—R$^{6a}$, —(C$_{2-6}$alkenyl)—R$^{6a}$, —(C$_{1-6}$alkyl)$_p$—OR$^{6b}$, —(C$_{2-6}$alkenyl)—OR$^{6b}$, —(C$_{1-6}$alkyl)$_p$—SR$^{6b}$, —(C$_{2-6}$alkenyl)—SR$^{6b}$, —(C$_{1-6}$alkyl)$_p$—S(O)R$^{6b}$, —(C$_{2-6}$alkenyl)—S(O)R$^{6b}$, —(C$_{1-6}$alkyl)$_p$—S(O)$_2$R$^{6b}$ or —(C$_{2-6}$alkenyl)—S(O)$_2$R$^{6b}$;

R$^{6a}$ is (Y$^6$)$_5$ substituted phenyl or

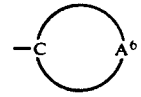

where A$^6$ completes substituted or unsubstituted 6-membered aromatic heterocycle (where the heterocycle contains 1 to 3 nitrogens the valences of which are satisfied by the ring and heterocycle substitution are defined above);

R$^{6b}$ is —(C$_{1-6}$alkyl)$_p$—((Y$^6$)$_5$ substituted phenyl) or

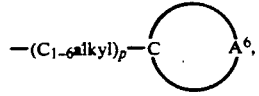

(where A$^6$ is defined immediately above); and

R$^{6c}$ is hydrogen or C$_{1-6}$alkyl;

R$^7$ is hydrogen or halogen;

Y$^2$ is —H, halogen, —OH, C$_{1-6}$alkyl, —CN, —CF$_3$, —(C$_{1-6}$alkyl)$_p$—O—C$_{1-6}$alkyl, —(C$_{1-6}$alkyl)$_p$—S—C$_{1-6}$alkyl, —(C$_{1-6}$alkyl)$_p$—S(O)—C$_{1-6}$alkyl, —(C$_{1-6}$alkyl)$_p$—S(O)$_2$—C$_{1-6}$alkyl, —O—(C$_{1-6}$alkyl)$_p$—C(O)OR$^{6c}$, —(C$_{1-6}$alkyl)$_p$—C(O)OR$^{6c}$, —(C$_{1-6}$alkyl)$_p$—C(O)NHOH, —(C$_{1-6}$alkyl)$_p$—C(O)NHR$^{6c}$ or —(C$_{1-6}$alkyl)$_p$—NHS(O)$_2$—(R$^7$)$_5$ substituted phenyl;

Y$^6$ is Y$^2$ or

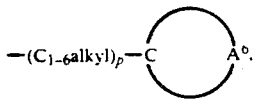

(where $A^6$ is defined immediately above); and p is 0 or 1.

DETAILED DESCRIPTION OF THE INVENTION

The invention can be readily understood by reference to the following text and flow sheet which describe the preferred embodiments and exhibit the processes for the synthesis of the instantly claimed compounds.

In general, analogs of 5-hydroxy-2,3-dihydrobenzofuran are well known. Thus, herein, the invention centers about particular substituents employed advantageously on the dihydrobenzofuran structure. Particular note should be taken of substituents $R^2$, $R^3$, $R^4$ and $R^6$ which are described below.

Herein, suitable —$C_{1-6}$alkyl, —$C_{2-6}$alkenyl, —($C_{1-6}$alkyl)— and —($C_{2-6}$alkenyl)— are well known in the art. Suitable —$C_{1-6}$alkyl, might be methyl, ethyl, propyl, i-butyl, t-butyl, n-butyl, pentyl, hexyl, cyclopropyl, or cyclohexyl. Suitable —$C_{2-6}$alkenyl may be selected from —$CHCH_2$, —$CH_2CHCH_2$, —$CH_2CHCHCH_3$, —$CH_2C(CH_3)CH_2$, and so on. Suitable —($C_{1-6}$alkyl)— might be —$CH_2$—, —$(CH_2)_2$—, —$(CH_2)_3$—, —($CH_2$)—C—$(CH_3)_2$—, —$(CH_2)$—C—$(CH_3)$—, etc. Suitable —($C_{2-6}$alkenyl)— include, —CHCH—, —$CH_2$CH—CH—, —$CH_2CH_2$CHCH—, —$CH_2$C—$(CH_3)$CH—, etc. The preferred —($C_{1-6}$alkyl)— is —(methyl)—, —(ethyl)— or —(propyl)— and —($C_{2-6}$alkenyl)— is —($CH_2$CHCH)—.

Suitable $R^2$ for use in compounds of formula (I) are $R^2$ where —($C_{1-6}$alkyl)— or —($C_{2-6}$alkenyl)— joins a phenyl, naphthyl, or 5- or 6-membered heterocycle to the 2-position of the dihydrobenzofuran. Formula (I) depicts the phenyl, naphthyl or heterocycle as

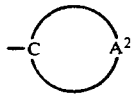

where $A^2$ completes the ring structure including substituents.

The phenyl and naphthyl of $R^2$ is $(Y^6)_5$ and $(Y^6)_7$ substituted respectively. Suitably, $Y^6$ is any of several common substituents as shown in formula (I), including the expected hydrogen. Each $Y^6$ may be independently selected. Yet while all $Y^6$ may be hydrogen or even halogen, it is clear that not all $Y^6$ may conveniently be other of the recited substituents. In the case of phenyl, it is preferred that at least two $Y^6$ are hydrogen or halogen. In the case of naphthyl, it is preferred that at least three $Y^6$ are hydrogen or halogen.

As stated above, the heterocycle of $R^2$ may be a substituted or unsubstituted 5-membered heterocycle, a substituted or unsubstituted 6-membered heterocycle, a 5-membered heterocycle with a fused $(Y^2)_{3or4}$ substituted benzene ring, or a 6-membered heterocycle having fused $(Y^2)_{3or4}$ substituted benzene ring. In the case of the 5- or 6-membered heterocycle, the point of attachment to —($C_{1-6}$alkyl)— or —($C_{2-6}$alkenyl)— is a carbon atom of the heterocyclic ring. Thus, the heterocycle must contain at least one carbon atom. In the cases of the 5- or 6-membered heterocycle with the fused benzene ring, this same point of attachment may be a carbon atom of the heterocyclic ring or a carbon atom of the fused ring. Thus, of necessity, the heterocyclic ring needs contain two carbon atoms, which are the points of fusion where attachment is through the benzene, or needs contain three carbon atoms, which are the points of fusion and attachment, where attachment is through the heterocycle. Notably, where attachment is through the heterocycle, then a fused benezene is $(Y^2)_4$ substituted, and where attachment is through a fused benezene, then such is $(Y^2)_3$ substituted.

The heterocyclic rings discussed above are well known in the art. Particularly, heterocycles herein contain 1 to 4 heteroatoms, including 0 to 1 in total of —O—, —S—, —NH— or —N($C_{1-4}$alkyl)— and 0 to 3 of nitrogen the valence of which is satisfied by the ring. Suitable 5-membered heterocycles include furanyl, thiophenyl, pyrrolyl, pyrazolyl, imidazolyl, thiazolyl, oxazolyl, triazolyl, tetrazolyl, etc. Suitable 6-membered heterocycles include alpha-pyronyl, gamma-pyronyl, pyridinyl, pyridazinyl, pyrimidinyl, pyrazinyl, thiopyronyl, etc. Suitable 5-membered heterocycles fused with a benzene ring include benzofuran-2-yl, benzofuran-6-yl, benzothiophen-2-yl benzothiophen-5-yl, indol-2-yl, indol-5-yl, benzopyrazol-3-yl, benzopyrazol-5-yl, benzimidazol-2-yl, benzimidazol-5-yl, benzoxazol-2-yl, benzoxazol-5-yl, etc. Suitable 6-membered heterocycles fused with a benzene ring include quinolin-2-yl, quinolin-4-yl, quinolin-7-yl, isoquinolin-1-yl, isoquinolin-3-yl, isoquinolin-7-yl, cinnolin-3-yl, quinazolin-2-yl, etc. Preferred heterocyclic rings are aromatic.

Substitution of the heterocycle ignoring hydrogen includes such groups as $C_{1-6}$alkyl, phenyl, halogen, —C(O)OH, —C(O)O$C_{1-6}$alkyl, —O$C_{1-6}$alkyl and the like. $Y^2$ substitution on the fused benzene ring is preferably hydrogen in the majority.

Preferred $R^2$ substituents herein are those in which the ring is phenyl. Thus, the preferred substituents are —($C_{1-6}$alkyl)—$(Y^6)_5$ substituted phenyl or —($C_{2-6}$alkenyl)—$(Y^6)_5$ substituted phenyl.

Suitable $R^3$ are selected from hydrogen, methyl, ethyl, propyl, etc. As to $R^3$ it is important to note that $R^3$ of formula (I) are independently selected. Preferably, $R^3$ is hydrogen or methyl.

As stated above, suitable $R^5$ are hydroxy or metabolizeable to hydroxy. Metabolizeable groups include: —OC(O)—($C_{1-6}$alkyl), —OC(O)O—($C_{1-6}$alkyl), —OC(O)O—(phenyl), —OC(O)—(phenyl), —O-SO$_3$NH$_4$, —OC(O)NR$_2'$, —O(O)P(OH)$_2$, —OC(O)—($C_{1-6}$alkyl)—COOR', —OC(O)—($C_{1-6}$alkyl)—NR$_2'$·HCl, etc., where R' is hydrogen, $C_{1-6}$alkyl or phenyl. Conveniently, $R^5$ is hydroxy.

$R^4$ and $R^6$ are suitably any of several classes of substituents as enumerated above. In simple cases, $R^4$ and $R^6$ are hydrogen; halogen, including chloro, fluoro, bromo, etc.; $C_{1-6}$alkyl or $C_{2-6}$alkenyl. As to this substitution, where one of $R^4$ or $R^6$ is hydrogen or halogen, then the other is not hydrogen or halogen. Preferably, at least one of $R^4$ and $R^6$ contain a heteroatom, aryl ring or both. Thus, $R^4$ and $R^6$ might contain phenyl, naphthyl, heterocycle, >C=O, —O—, —S—, —S(O)—, —S(O)$_2$— or —N<, etc. Ignoring the simple substitution named above $R^4$ and $R^6$ of formula (I) are classified according to which of aryl or heteroatom is most directly substituted to the 4- or 6-position of the dihydrobenzofuran. Where the most direct substitution is —O—, —S—, —S(O)—, —S(O)$_2$— or —N< then such substitution may be bonded directly to the dihydrobenzofuran or there may be an intervening —(C$_{1-6}$alkyl)— or —(C$_{2-6}$alkenyl)— bridge. Where the most direct substitution is phenyl, naphthyl, >C=O or heterocycle as defined, then such should be bonded to the 4- or 6-position of the dihydrobenzofuran through at least a —(C$_{1-6}$alkyl)— or a —(C$_{2-6}$alkenyl)—.

In accordance with the foregoing, R$^{6a}$ which is phenyl, naphthyl, carbonyl or heterocycle is attached to the 4- or 6-position of the dihydrobenzofuran through either a —(C$_{1-6}$alkyl)— or —(C$_{2-6}$alkenyl)—. As the most direct substitution, the phenyl or naphthyl in R$^{6a}$ may be further substituted with Y$^6$. Y$^6$ represents a range of further substitution as possible on the phenyl or naphthyl. This further substitution includes the substitution represented by Y$^2$, i.e., hydrogen, halogen, hydroxy, C$_{1-6}$alkyl, cyano, trifluoromethyl and various heteroatom containing groups. This further substitution also includes heterocycles. As the most direct substitution, the heterocycle in R$^{6a}$ is defined as

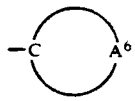

where A$^6$ completes any of the heterocycles enumerated above as completed by A$^2$. The difference between A$^2$ and A$^6$ is that A$^2$ is intended to complete non-heterocyclic rings such as phenyl and naphthyl.

Also in accordance with the foregoing, R$^{6b}$ represents further substitution where a heteroatom, such as, —O—, —S—, —S(O)—, —S(O)$_2$— or —NR$^{6c}$— is attached to the 4- or 6-position of the dihydrobenzofuran either directly or through a —(C$_{1-6}$alkyl)— or —(C$_{2-6}$alkenyl)—. In addition to other substitutents, R$^{6b}$ might be Y$^6$ substituted phenyl or naphthyl, or a heterocycle of the type completed by A$^6$.

R$^7$ is defined in formula (I) as hydrogen, C$_{1-6}$alkyl, C$_{2-6}$alkenyl or halogen. Suitable R$^7$ include hydrogen, methyl, ethyl, propyl, propenyl, t-butyl, chlorine, fluorine, bromine, etc.

Table 1 lists compounds within the scope of formula (I) and precursors thereof. In the course of listing these compounds, a number of specific R$^2$, R$^3$, R$^4$, R$^5$, R$^6$ and R$^7$ are enumerated. The following abbreviations are employed to simplify presentation. All substitution is hydrogen unless otherwise specified. Abbreviations in table 1 are:

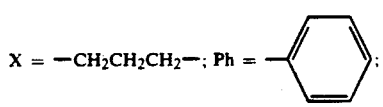

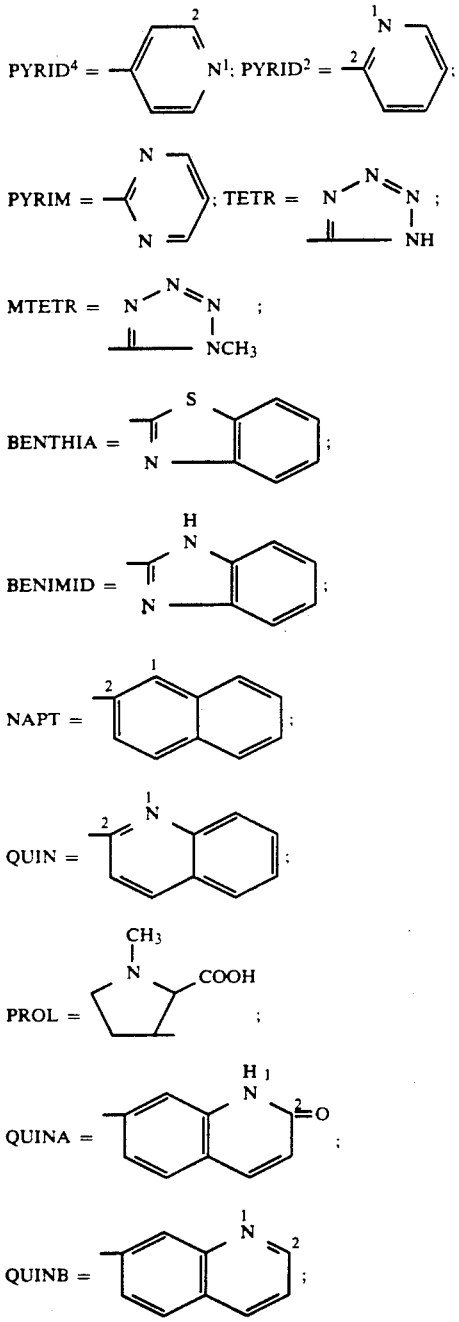

Me=methyl; Pr=propyl; Ac=—C(O)CH$_3$ and Et-=ethyl.

TABLE 1

| No. | —R$^2$ | —R$^3$/R$^3$ | —R$^4$ | —R$^5$ | —R$^6$ | —R$^7$ | Ex. No. |
|---|---|---|---|---|---|---|---|
| 1 | CH$_2$Ph | Me/H | H | OH | OH | H | |
| 2 | CH$_2$Ph-p-OMe | Me/H | Pr | OH | H | H | |
| 3 | CH$_2$Ph-p-OMe | Me/H | H | OH | H | H | 20 |
| 4 | CH$_2$Ph-p-OH | Me/H | Pr | OH | H | H | |
| 5 | CH$_2$CH$_2$Ph-p-OMe | Me/Me | H | OH | H | H | 24 |
| 6 | CH$_2$Ph-p-OMe | Me/H | H | OH | H | H | |
| 7 | CH$_2$Ph-p-F | Me/H | Pr | OH | H | H | |
| 8 | CH$_2$Ph-p-OMe | Me/H | Pr | OAc | H | H | |
| 9 | CH$_2$Ph-p-OMe | Me/H | Pr | OCO$_2$Me | H | H | |
| 10 | CH$_2$Ph-p-OCH$_2$CO$_2$Et | Me/H | allyl | OH | H | H | |
| 11 | CH$_2$Ph-p-OCH$_2$CO$_2$H | Me/H | allyl | OH | H | H | |

TABLE 1-continued

| No. | —R² | —R³/R³ | —R⁴ | —R⁵ | —R⁶ | —R⁷ | Ex. No. |
|---|---|---|---|---|---|---|---|
| 12 | CH₂Ph-p-OMe | Me/H | H | OH | allyl | H | |
| 13 | CH₂Ph-p-OMe | Me/H | H | OH | Pr | H | |
| 14 | CH₂Ph-p-OMe | Me/H | H | OH | XOH | H | |
| 15 | CH₂Ph-p-OMe | Me/H | H | OSO₃NH₄ | H | H | |
| 16 | CH₂Ph-p-OMe | H/H | H | OH | H | H | |
| 17 | CH₂Ph-p-OMe | H/H | H | OH | allyl | H | |
| 18 | CH₂Ph-p-OMe | Me/H | H | OH | CH₂CH₂CHCHPh-p-Cl | H | |
| 19 | CH₂Ph-p-OMe | Me/H | H | OH | (CH₂)₄Ph-p-Cl | H | |
| 20 | CH₂Ph-p-OMe | Me/Me | H | OH | allyl | H | |
| 21 | CH₂Ph-p-OMe | Me/H | H | OH | X—OPh | H | |
| 22 | CH₂Ph-p-OMe | Me/Me | H | OH | H | H | |
| 23 | CH₂CH₂Ph-p-OMe | Me/He | H | OH | allyl | H | |
| 24 | CH₂CH₂Ph-p-Cl | Me/Me | H | OH | Pr | H | |
| 25 | CH₂CH₂Ph-p-SMe | Me/Me | H | OH | Pr | H | 26 |
| 26 | CH₂CH₂Ph-p-SMe | Me/Me | H | OH | X—OH | H | |
| 27 | CH₂CH₂Ph-p-SO₂Me | Me/Me | H | OH | Pr | H | |
| 28 | CH₂CH₂Ph-p-SOMe | Me/Me | H | OH | Pr | H | |
| 29 | CH₂CH₂Ph-p-Cl | H/H | H | OH | O—X-Ph | H | |
| 30 | CH₂Ph-p-OMe | H/H | allyl | OH | H | H | |
| 31 | CH₂CH₂Ph | Me/Me | H | OH | X—OPh | H | |
| 32 | CH₂Ph-p-OMe | H/H | H | OH | Br | H | |
| 33 | CH₂CH₂Ph-p-Cl | Me/Me | H | OH | X—OPh-p-Cl | H | |
| 34 | CH₂CHCHPh-p-Cl | Me/Me | H | OH | SPh | H | |
| 35 | CH₂CH₂Ph-p-Cl | H/H | H | OH | allyl | H | 4 |
| 36 | CH₂CH₂Ph-p-Cl | H/H | allyl | OH | H | H | 4 |
| 37 | CH₂CH₂Ph | Me/Me | H | OH | X—OH | H | |
| 38 | CH₂CH₂Ph-p-Cl | H/H | H | OH | X—OPh-p-Cl | H | 6 |
| 39 | CH₂CH₂Ph-p-Cl | Me/Me | H | OH | X—OPh-p-Cl | H | |
| 40 | CH₂CH₂Ph-p-Cl | Me/Me | H | OH | Pr | H | |
| 41 | CH₂CH₂Ph-p-Cl | Me/Me | H | OH | t-butyl | H | |
| 42 | CH₂CH₂Ph-p-Cl | Me/Me | H | OH | H | t-butyl | |
| 43 | CH₂CH₂Ph-p-Cl | H/H | H | OH | X—OH | H | 5 |
| 44 | CH₂CH₂Ph-p-Cl | Me/Me | H | OH | X—S-PYRID⁴ | H | |
| 45 | CH₂CH₂Ph-p-Cl | Me/Me | H | OH | X—S-PYRIM | H | |
| 46 | CH₂CH₂Ph-p-Cl | Me/Me | H | OH | X—S—CH₂CH₂C(O)NMe₂ | H | |
| 47 | CH₂CH₂Ph | H/H | Pr | OH | H | H | |
| 48 | CH₂CH₂Ph | H/H | allyl | OH | H | H | 2 |
| 49 | CH₂CH₂Ph | H/H | H | OH | Pr | H | |
| 50 | CH₂CH₂Ph | H/H | H | OH | allyl | H | 2 |
| 51 | CH₂CH₂Ph | H/H | H | OH | H | H | 1 |
| 52 | CH₂CH₂Ph | H/H | H | OH | X—OPh | H | 13, 14, 15 |
| 53 | CH₂CH₂Ph | H/H | H | OH | CH₂-cyclopropyl | H | |
| 54 | CH₂CH₂Ph-p-C(O)Me | H/H | H | OAc | H | H | |
| 55 | CH₂CH₂Ph-p-C(O)Me | H/H | H | OH | H | H | |
| 56 | CH₂CH₂Ph-p-OH | H/H | H | OH | H | H | |
| 57 | CH₂CH₂Ph-p-Cl | H/H | allyl | OH | allyl | H | |
| 58 | CH₂CH₂Ph-p-Et | H/H | H | OH | H | H | |
| 59 | CH₂CH₂Ph-p-Cl | H/H | H | OH | H | H | 3 |
| 60 | CH₂CH₂Ph | H/H | H | OC(O)NMe₂ | X—OPh | H | |
| 61 | X-Ph | H/H | H | OH | allyl | H | |
| 62 | X-Ph | H/H | allyl | OH | H | H | |
| 63 | CH₂CH₂Ph | H/H | H | OSO₃NH₄ | X—OPh | H | |
| 64 | CH₂CH₂Ph | H/H | H | OH | X—S-PYRID⁴ | H | |
| 65 | CH₂CH₂Ph | H/H | H | OH | X—OPh-p-COOH | H | |
| 66 | CH₂CH₂Ph | H/H | Pr | OH | X—OPh | H | |
| 67 | CH₂CH₂Ph | Me/Me | Pr | OH | X—OPh | H | |
| 68 | CH₂CH₂Ph | H/H | H | O-β-glucuronide | X—OPh | H | |
| 69 | CH₂CH₂Ph | H/H | Pr | OH | X—OPh-p-COOH | H | |
| 70 | CH₂CH₂Ph | H/H | H | MeGLYC(O)O— | X—OPh | H | |
| 71 | CH₂CH₂Ph | H/H | H | OH | X—OPh-p-TETR | H | 8 |
| 72 | CH₂CH₂Ph | H/H | H | OH | X—OPh-p-MTETR | H | |
| 73 | CH₂CH₂Ph | H/H | H | OH | X—NMe₂ | H | |
| 74 | CH₂CH₂Ph | H/H | H | OH | X—OPh-p-C(O)NH₂ | H | |
| 75 | CH₂CH₂Ph | H/H | H | OH | CH₂CH₂C(CH₃)COOH | H | |
| 76 | CH₂CH₂Ph | H/H | H | O(CH₂)₄COOMe | X—OPh | H | |
| 77 | CH₂CH₂Ph | H/H | H | O(CH₂)₄COOH | X—OPh | H | |
| 78 | CH₂CH₂Ph | H/H | H | OC(O)—S-PROL | X—OPh | H | |
| 79 | CH₂CH₂Ph | H/H | H | OC(O)XCOOH | X—OPh | H | |
| 80 | CH₂CH₂Ph | H/H | H | OH | X—OPh-p-CH₂COOH | H | |
| 81 | CH₂CH₂Ph | H/H | H | OC(O)—S-PROL | X—OPh | H | |
| 82 | CH₂CH₂Ph | H/H | H | OH | X—OPh-p-CMe₂COOH | H | 17 |
| 83 | CH₂CH₂Ph | H/H | H | OH | X—OPh-p-CHMeCOOH | H | |
| 84 | CH₂CH₂Ph | H/H | H | OH | X—S-BENTHIA | H | 18 |
| 85 | CH₂CH₂Ph | H/H | H | OH | X—S-BENIMID | H | |
| 86 | CH₂CH₂Ph | H/H | H | OH | X—OPh-o-TETR | H | |
| 87 | CH₂CH₂Ph | H/H | H | OH | X—OPh-o-Me-p-TETR | H | |
| 88 | CH₂CH₂Ph | H/H | H | OH | X—O-NAPT-1-TETR | H | 11 |
| 89 | CH₂CH₂Ph | H/H | H | OH | (CH₂)₄Ph | H | 10 |

TABLE 1-continued

| No. | —R² | —R³/R³ | —R⁴ | —R⁵ | —R⁶ | —R⁷ | Ex. No. |
|---|---|---|---|---|---|---|---|
| 90 | CH₂CH₂Ph | H/H | H | OH | X—OPh-p-C(O)NHOH | H | 19 |
| 91 | CH₂CH₂Ph | H/H | H | OH | X—OPh-o-Cl-p-TETR | H | |
| 92 | CH₂CH₂Ph | H/H | Pr | OH | X—OPh-p-C(CH₃)₂-TETR | H | |
| 93 | CH₂CH₂Ph | H/H | H | OH | X—OPh-p-C(CH₃)₂-TETR | H | |
| 94 | CH₂CH₂Ph | H/H | X—OPh-p-TETR | OH | H | H | 12 |
| 95 | CH₂CH₂Ph | H/H | X—OPh-p-COOH | OH | H | H | |
| 96 | CH₂CH₂Ph | H/H | X—S-PYRID⁴ | OH | H | H | |
| 97 | CH₂CH₂Ph | H/H | H | OC(O)CH₂NMe₂·HCl | H | H | |
| 98 | CH₂CH₂Ph | H/H | H | OH | X—OPh-p-CH₂CH₂CMe₂COOH | H | |
| 99 | CH₂CH₂Ph | H/H | Pr | OH | X—OPh-p-CH₂CH₂CMe₂COOH | H | |
| 100 | CH₂CH₂Ph | H/H | Pr | OH | X—OPh-p-CH₂CH₂CMe₂COOH | H | |
| 101 | CH₂CH₂Ph | H/H | H | OH | X—OPh-2-Pr-3-OH-4-Ac | H | |
| 102 | CH₂CH₂Ph | H/H | H | OH | X—O-NAPT-6-TETR | H | |
| 103 | CH₂CH₂Ph | H/H | H | OH | X—S-QUIN-6-COOMe | H | |
| 104 | CH₂CH₂Ph | H/H | H | OH | X—S-QUIN-6-COOH | H | |
| 105 | CH₂CH₂Ph | H/H | H | OH | X—S-QUINB-2-OMe-3-COOMe | H | 9 |
| 106 | CH₂CH₂Ph | H/H | H | OH | X—S-QUINB-2-OMe-3-COOH | H | 9 |
| 107 | CH₂CH₂Ph | H/H | H | OH | X—OPh-2,3-Cl-4-CMe₂COOH | H | |
| 108 | CH₂CH₂Ph | H/H | H | OH | (CH₂)₄Ph-p-C(CH₃)₂COOH | H | |
| 109 | CH₂CH₂Ph | H/H | H | OH | X—OPh-o-Ac-m-OH | H | |
| 110 | CH₂CH₂Ph | H/H | H | OH | X—OPh-m-OH-p-Ac | H | |
| 111 | CH₂CH₂Ph | H/H | H | OH | X—SPh-p-C(CH₃)₂COOH | H | |
| 112 | CH₂CH₂Ph | H/H | H | OH | X—S-QUINB-2-t-bu-3-COOH | H | |
| 113 | CH₂CH₂Ph | H/H | H | OH | X-QUINA-3-COOH | H | |
| 114 | CH₂CH₂Ph | H/H | H | OH | X—OPh-p-TETR | H | |
| 115 | CH₂CH₂Ph | H/H | H | OH | X—S-PYRID²-5-COOH | H | |
| 116 | CH₂CH₂Ph | H/H | H | OH | X—S-QUINB-2-Ph-3-COOH | H | |
| 117 | CH₂CH₂Ph | H/H | H | OH | CH₂Ph | H | |
| 118 | CH₂CH₂Ph | H/H | H | OH | CH₂CH₂CHCHPh-p-CMe₂COOH | H | |
| 119 | CH₂CH₂Ph | H/H | H | OH | CH₂Ph-2,4-Cl | H | |
| 120 | CH₂CH₂Ph | H/H | H | OH | CH₂Ph-4-OMe | H | |
| 121 | CH₂CH₂Ph | H/H | H | OH | CH₂Ph-4-Cl | H | |
| 122 | CH₂CH₂Ph | H/H | H | OH | CH₂Ph-4-SMe | H | |
| 123 | CH₂CH₂Ph | H/H | H | OH | CH₂Ph-3,5-Cl | H | |
| 124 | CH₂CH₂Ph | H/H | H | OH | CH₂Ph-4-SO₂Me | H | |
| 125 | CH₂CH₂Ph | H/H | H | OH | CH₂Ph-3,4-Cl | H | |
| 126 | CH₂CH₂Ph | H/H | H | OH | CH₂Ph-4-NH₂·HCl | H | |
| 127 | CH₂CH₂Ph | H/H | H | OH | CH₂Ph-4-NHSO₂Ph | | |
| 128 | CH₂CH₂Ph | H/H | H | OH | CH₂Ph-4-NHC(O)CH₃ | H | |
| 129 | CH₂CH₂Ph | H/H | H | OH | CH₂Ph-4-S-iPr | H | |
| 130 | CH₂CH₂Ph | H/H | H | OH | CH₂Ph-4-SO₂-iPr | | |
| 131 | CH₂CH₂Ph | H/H | H | OH | X—SO₂Ph | | |
| 132 | CH₂CH₂Ph | H/H | H | OH | CH₂Ph-4-SO-Me | H | |
| 133 | CH₂CH₂Ph | H/H | H | OH | CH₂Ph-2-OMe | H | |
| 134 | CH₂CH₂Ph | H/H | H | OH | cis-CHCH-Ph | H | |
| 135 | CH₂CH₂Ph | H/H | H | OH | trans-CHCH-Ph | H | |
| 136 | CH₂CH₂Ph | H/H | H | OH | CH₂CH₂Ph | H | |
| 137 | CH₂CH₂Ph | H/H | H | OH | X-Ph-4-SO₂Me | H | |
| 138 | CH₂CH₂Ph | H/H | H | O(O)P(OH)₂ | X-Ph | H | |
| 139 | CH₂CH₂Ph | H/H | H | OH | cis-CHCH-Ph-4-Cl | H | |
| 140 | CH₂CH₂Ph | H/H | H | OH | trans-CHCH-Ph-4-Cl | H | |
| 141 | CH₂CH₂Ph | H/H | H | OH | CH₂Ph-4-NHSO₂Me | H | |
| 142 | CH₂CH₂Ph | H/H | H | OH | trans-CHCH-Ph-4-SO₂Me | H | |
| 143 | CH₂CH₂Ph | H/H | H | OH | CH₂Ph-4-NO₂ | H | |
| 144 | CH₂CH₂Ph | H/H | H | OH | trans-CHCH-Ph-4-OMe | | |
| 145 | CH₂CH₂Ph | H/H | H | OH | CH₂CH₂Ph-4-OMe | H | |
| 146 | CH₂Ph-p-OMe | Me/H | H | OH | X—O-Ph | H | 21 |
| 147 | CH₂Ph-p-OMe | Me/H | H | OH | X—CH₂Ph-p-Cl | H | 22 |

The substitution R² is suitably any of the above. Most preferrably, R² is —(C₁₋₆alkyl)$_p$—((Y⁶)₅ substituted phenyl) or —(C₂₋₆alkenyl)—(Y⁶)₅ substituted phenyl where Y⁶ may be preferably hydrogen, chlorine, —O—C₁₋₆alkyl, —S—C₁₋₆alkyl, and —C(O)—C₁₋₆ alkyl. Included within preferred R² are —CH₂Ph, —CH₂Ph—p—OMe, —CH₂Ph—p—Cl, —CH₂CH₂Ph, —CH₂CH₂Ph—p—SMe, —CH₂CH₂Ph, etc.

Preferred embodiments for R⁶ are those selected from —(C₁₋₆alkyl)—R⁶ᵃ, —(C₂₋₆alkenyl)—R⁶ᵃ, —(C₁₋₆alkyl)$_p$—OR⁶ᵇ, —(C₂₋₆alkenyl)—OR⁶ᵇ, —(C₁₋₆alkyl)-$_p$—SR⁶ᵇ, —(C₂₋₆alkenyl)—SR⁶ᵇ, —(C₁₋₆alkyl)$_p$—S-(O)R⁶ᵇ, —(C₂₋₆alkenyl)—S(O)R⁶ᵇ, —(C₁₋₆alkyl)$_p$—S(O)₂R⁶ᵇ or —(C₂₋₆alkenyl)—S(O)₂R⁶ᵇ where R⁶ᵃ and R⁶ᵇ preferably contain —((Y⁶)₅ substituted phenyl) or

where A⁶ completes substituted or unsubstituted 6-membered aromatic heterocycle or a substituted or unsubstituted 6-membered aromatic heterocycle having fused thereto a (Y²)₃ ₒᵣ ₄ substituted benzene ring (where the heterocycle contains 1 to 3 nitrogens the valences of which are satisfied by the ring and heterocycle substitution are defined above). Included within preferred R⁶ are —X—O—Ph, —X—O—Ph—p—Cl, —X—S—PYRID⁴, —X—O—Ph—p—TETR, —X—O—Ph—p—C(CH₃)₂COOH, —X—OPh—p—C(O)N-

HOH. —X—O—Ph—p—C(CH$_2$)$_2$—TETR, —X—
—S—QUINB—2—OMe—3—COOH, —X—CH$_2$-
Ph—p—C(CH$_2$)COOH, etc.

Compounds of formula (I) may be manufactured by any one of numerous reaction schemes. Obviously, different schemes will produce different compounds in yields that vary depending on substituents involved. Herein, to produce the range of subject compounds a two-part synthesis is suggested. In part one of the suggested synthesis, a dihydrofuran ring structure may be modified or synthesized within the definition of formula (I) by schemes which permit the entire selection of R$^2$ and R$^3$ substitution. Subsequent substitution in part two of the suggested synthesis results in preferred R$^4$, R$^5$, R$^6$ and R$^7$. Reactions to add and remove protecting groups may be employed as necessary. It is believed that the suggested two part synthesis will produce all desired compounds in significant yields. The examples provided later disclose other syntheses which may be more advantageous to produce specific compounds.

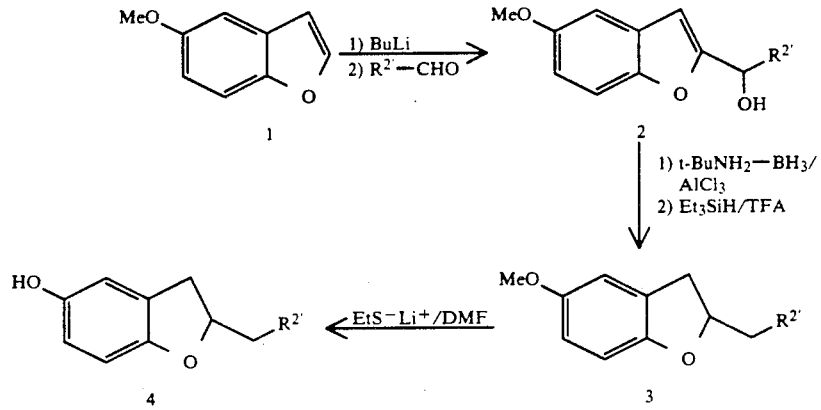

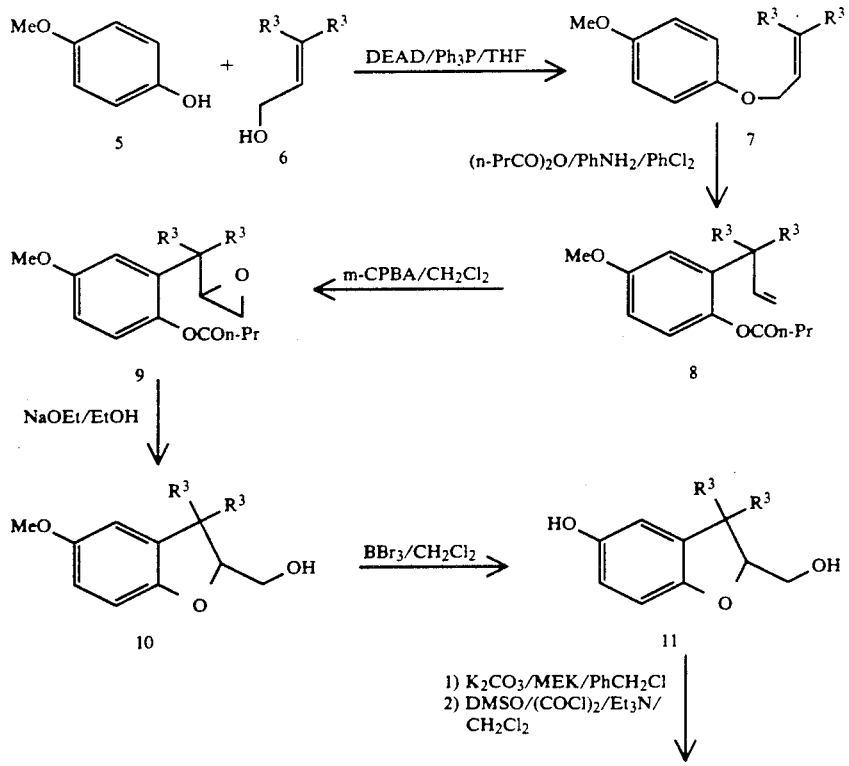

-continued
FLOW SHEET B
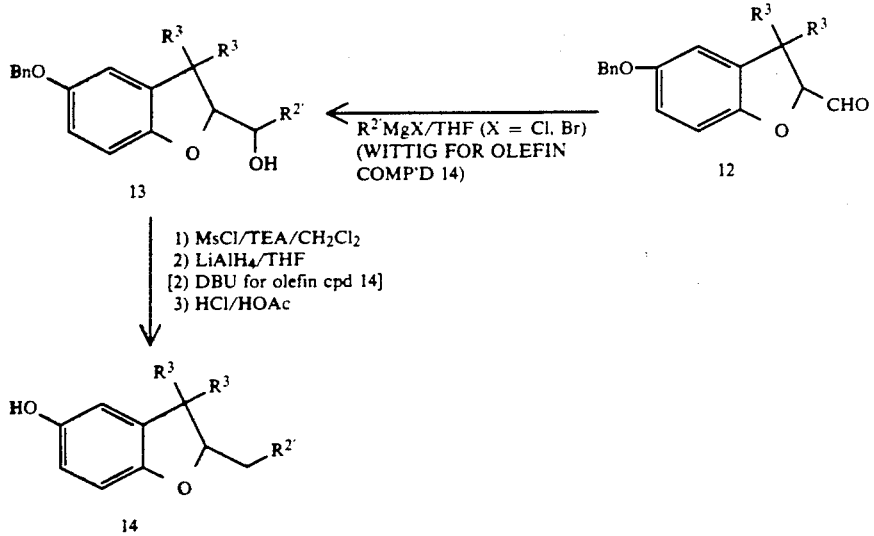
FLOW SHEET C
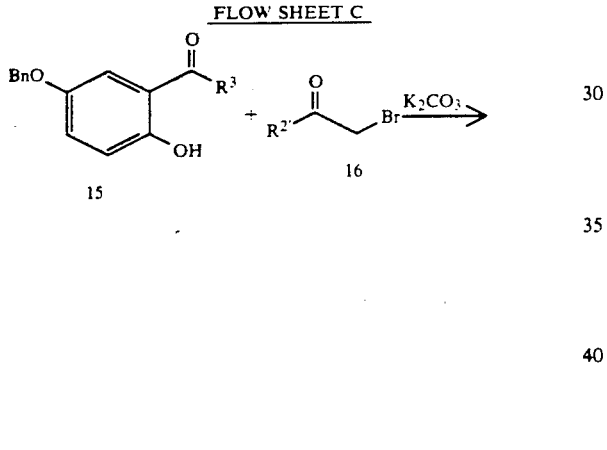
-continued
FLOW SHEET C
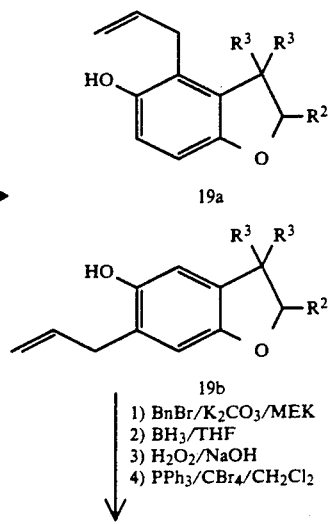
FLOW SHEET D
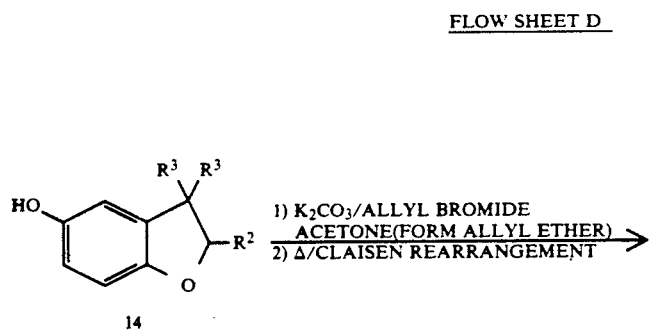

FLOW SHEET D
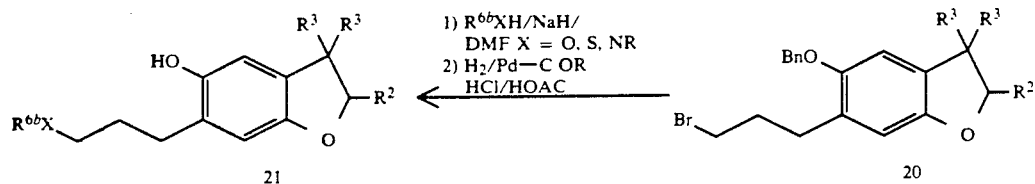
FLOW SHEET E
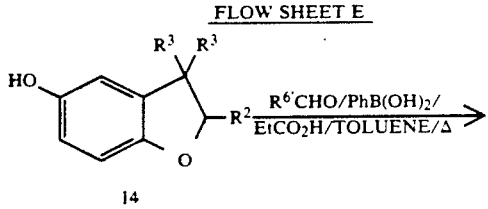
-continued
FLOW SHEET E
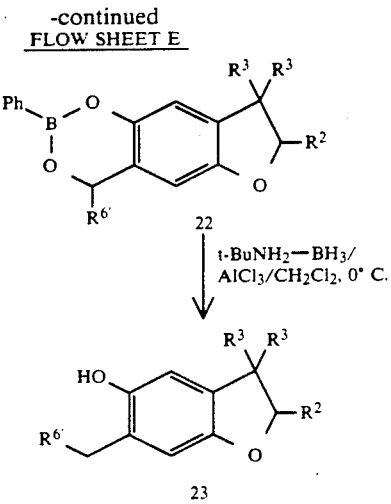
FLOW SHEET F
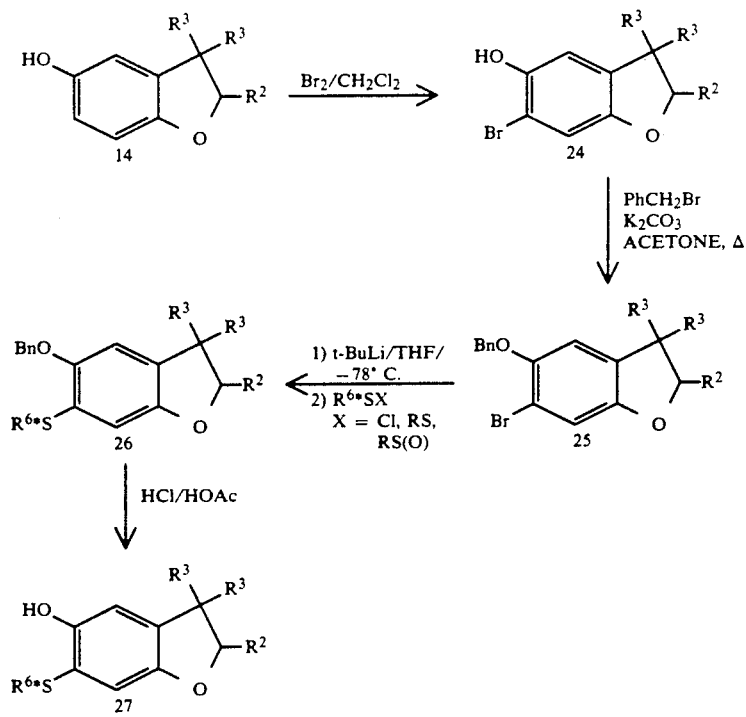

5,091,533
FLOW SHEET G
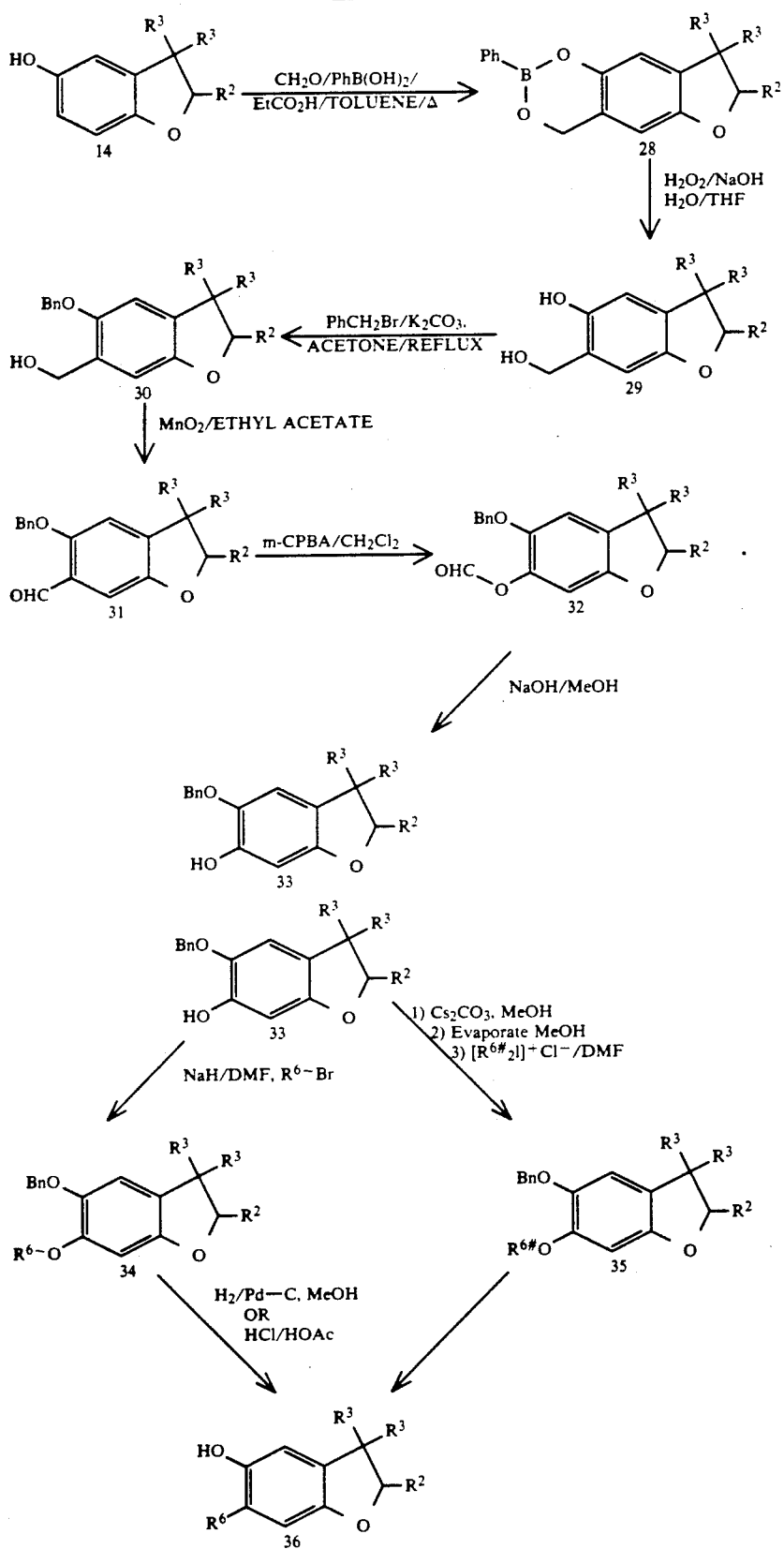

FLOW SHEET H

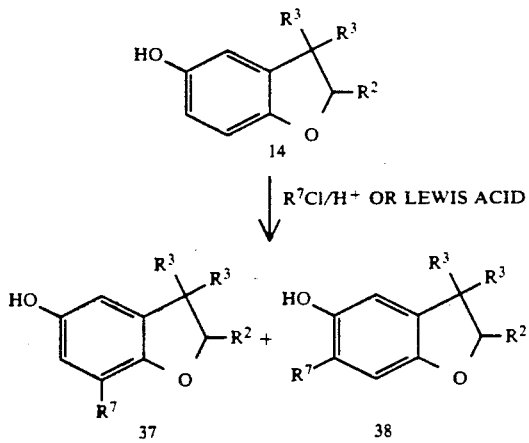

FLOW SHEET I

FLOW SHEET J

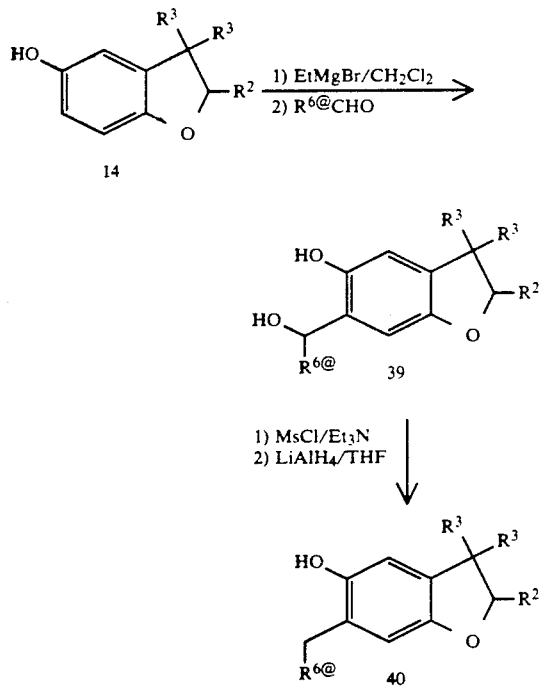

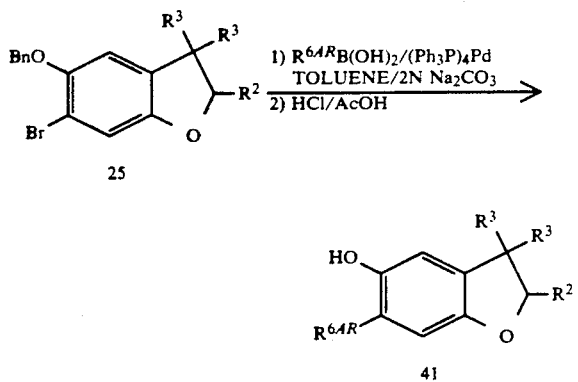

Flow Sheets A–C disclose part one of the suggested synthesis. Dihydrobenzofuran compounds of formula (I) are synthesized with $R^2$ and $R^3$ substitution selected from the entire defined class. The neccessity and advantage of the various flow sheets for part one is the difficulty in connection with obtaining desired $R^3$ substitution as seen. In Flow Sheets A–C, $R^{2'}$ represents the remainder of $R^2$ absent the alpha carbon.

Referring to Flow Sheet A, 5-methoxybenzofuran, Compound 1, is a well known and described starting material, easily obtained on the market. Compound 1 may be lithiated at about $-78°$ C. by the addition of butyl lithium in a solvent such as anhydrous tetrahydrofuran. Subsequently, the lithiated species is quenched by the addition of $R^{2'}$—CHO, preferably in an identical solvent. This quenching reaction results in a 2-position substitution of $R^{2'}$—CHO forming an alcohol of the aldehyde as shown in Compound 2.

Compound 2 may be deoxygenated to remove the alcohol by reduction using t-butylamine borane and aluminum trichloride followed by a second reduction to remove the unsaturation of the 2- and 3-position using triethylsilane in excess trifluoroacetic acid, TFA. The resulting Compound 3 has a 2-position substitution of $R^2$, a 3-position substitution of H/H and a 5-position substitution of —OMe. The —OMe of Compound 3 is not readily metabolized and may be deprotected to hydroxy by demethylation using lithium ethylthiolate in dimethyl formamide to produce Compound 4.

Referring to Flow Sheet B, 4-methoxyphenol, Compound 5 and $R^3$ substituted allyl alcohol 6 are well known and described starting materials. The phenol 5 may be etherified to ether 7 with allyl alcohol 6 in tetrahydrofuran as a solvent using diethylazodicarboxylate and triphenylphosphine at from 0° to 65° C. Ether 7 will undergo a Claisen Rearrangement to produce a 2-substituted phenol, the 1-hydroxy of which is esterified with a protective group to produce 2-, 4-substituted, protected phenol 8. The Claisen Rearrangement to produce the 2-substituted phenol and the esterification to produce the protecting group is accomplished by refluxing ether 7 in dichlorobenzene as a solvent using butanoic acid anhydride and aniline. The protecting group on phenol 8 is present to protect the 1-hydroxy in a subsequent epoxidation step. To produce Compound 9, the 2-substituent of compound 8 is epoxidized at from 0° C. to room temperature in dichloromethane using meta-chloroperbenzoic acid. Subsequently, the 2-epoxy substituent on epoxy 9 and the 1-ester substituent may be induced to close and give a base "dihydrobenzofuran" structure, Compound 10. This is accomplished by hydrolysis of the 1-ester in ethanol with NaOET at from 0° to about 68° C. with concomitant closure of the furan. Compound 10 has the basic structure of dihydrobenzofuran as well as desirable 2-, 3- and 5-position substitution. The 5-position has a protected hydroxy and the 2-position a hydroxymethyl substituent convenient to further elaboration. To proceed with the synthesis of Flow Sheet B, the 5-position protecting group is removed with $BBr_3$ in dichloromethane to form Compound 11 which is identical to Compound 10 except for the resultant 5-position hydroxy. In a two-step reaction Compound 11 is firstly reprotected in the 5-position and secondly oxidized from an alcohol to an aldehyde in the 2-position to produce aldehyde 12. Reprotection with benzyl takes place upon refluxing Compound 11 with benzyl chloride and $K_2CO_3$ in methylethylketone. The oxidation is accomplished in dichloromethane with dimethylsulfoxide and oxallyl chloride at from −78° C. to room temperature. The aldehyde 12 may be substituted with $R^{2'}$ through a Grignard Reaction in tetrahydrofuran with $R^{2'}MgBr$ to produce Compound 13. With the substitution of $R^2$, it remains only to deprotect the hydroxy of the 5-position and remove a hydroxy of the 2-position to produce the desired compound of Flow Sheet B, Compound 14. Removal of the 2-position hydroxy is accomplished firstly by forming a sulfonate ester of the hydroxy in dichloromethane with methane sulfonyl chloride and triethylamine at about −78° C. and secondly by removing the sulfonate ester with LiAlH at from 0° to 65° C. Deprotection of the 5-position hydroxy may subsequently accomplished by hydrogenolysis or treatment with HCl/acetic acid. Shown in Flow Sheet B is production of Compound 14 having a saturated alpha carbon in the 2-position substitution, i.e., $R^2$. An unsaturated alpha-beta carbon bond may be obtained in the reaction from Compound 13 to Compound 14 where instead of removing the sulfonate ester with LiAlH, it is removed with diazadicycloundecene, DBU. Alternatively, an unsaturated alpha-beta carbon bond might be obtained utilizing a Wittig Reaction and Wittig Reagent in the reaction from aldehyde 12. Other unsaturation in $R^2$ can of course pre-exist in either the Wittig Reagent or Grignard Reagent. The resulting Compound 14 has a 2-position substitution of $R^2$ a 3-position substitution of $R^3/R^3$, i.e., any of H/H, Me/H, Me/Me, etc., and a 5-position substitution of hydroxy.

Referring to Flow Chart C, Compound 15 and Compound 16 are well known starting materials. In a two-step reaction, Compound 15 is etherified with Compound 16 followed by condensation to produce benzofuran 17. Benzofuran 17 may be hydrogenated to remove the benzyl protecting group and saturate the 2-/3-position olefin followed by treatment with triethylsilane in trifluoroacetic acid to remove the carbonyl of the 2-position. The resultant Compound 18 has the basic dihydrobenzofuran structure with desired 2-, 3- and 5-position substitution.

Thus, Compounds 4, 14 and 18 in accordance with the stated objectives of part one of the suggested synthesis may have various $R^2$ and $R^3$ substitution. These compounds not only fall within formula (I), but are useful to produce additional compounds of formula (I). $R^4$, $R^5$, $R^6$ and $R^7$ may be modified as described below in the description of part two of the synthesis.

Flow Sheets D, E, F, G and H demonstrate reactions of part two of the suggested synthesis in which preferred 4-, 6- and 7-position substitution is added. Flow Sheets D, E, F, and G exhibit synthesis schemes dealing with the 4- and 6-position. Flow Sheet H exhibits a synthesis scheme dealing with 7-position.

Referring to Flow Sheet D, any of Compounds 4, 14, or 18 may be employed as a starting material to produce a 4- or 6-position substitution of $R^{6b}Z(CH_2)_3$- or $R^{6c}N(CH_2)_3$-where Z is O or S. Compound 14 which is generic to both 4 and 18 is depicted.

Compound 14 is a simple case of formula (I) on which preferred 4- or 6-position substitution is desired. As a first reaction, the 5-position hydroxy of Compound 14 is allylated using potassium carbonate and allyl bromide in allyl ether followed by a Claisen Rearrangement to obtain both 6- or 4-position allyl substitution. Compound 19b depicts the favored 6-position allyl product and Compound 19a depicts the 4-position isomer. Subsequently, the allyl substitution may be modified as depicted by Flow Sheet D employing the 6-position allyl isomer 19b as exemplary. Modification of the allyl begins with a bromine addition to the allyl unsaturation as shown in Compound 20. This addition of the bromine to the unsaturation is accomplished in four steps. Firstly, the 5-position hydroxy should be protected by reaction, for example, with benzyl bromide to produce a 5-position benzyloxy substitution. Subsequently, the allyl is hydroborated by reacting with $BH_3$ at 0° C. to room temperature. Following hydroboration, the borate is oxidized by refluxing in tetrahydrofuran at 65° C. with $H_2O_2$ and base to give the corresponding alcohol. Fourthly and finally, the alcohol is treated with triphenyl phosphine and carbon tetrabromide at from 0° C. to room temperature to produce Compound 20.

Following addition of the bromide to the allyl unsaturation, the bromide is in turn replaced with —$ZR^{6b}$ or $N(R^{6c})_2$ to produce a preferred 4- or 6-position substitution where Z is O or S. This may be accomplished in two steps by firstly, generating in the presence of Compound 20, an $R^{6b}Z$— or $R^{6c}{}_2N$— anion from $R^{6b}ZH$ or $(R^{6c})_2NH$ with NaH in dimethyl formamide and subsequently hydrogenating. The resulting 4- or 6-position substitution as described and shown in Compound 21 is —($C_3$alkyl)—Z—$R^{6b}$ or —($C_3$alkyl)—N($R^{6c}$)$_2$.

Simple modifications of the reaction scheme in Flow Sheet D will produce a broader range of substitution. For instance, —S— as —Z— may be converted to —S(O)— or —S(O)$_2$— by oxidation with hydrogen peroxide and/or oxone. Also, the alkyl chain might be shortened to $C_2$ by ozonolysis or osmium tetroxide/sodium metaperiodate treatment followed by reduction to give alcohol. This alcohol might be carried on as described for the longer chain. Further, the alkyl chain length might be lengthened by oxidation of the alcohol to an aldehyde and a subsequent Wittig Condensation. Other modifications will be clear to those skilled in the art.

Flow sheet E, as compared to Flow Sheet D depicts a synthesis providing a broader range of 4- or 6-position substitution, namely $R^{6'}CH_2$—. Again, any of Compounds 4, 14 or 18 may be employed as starting materials. Compound 14 is shown.

As the first reaction of Flow Sheet E, Compound 14 is subjected to a boron assisted electrophilic substitution of $R^{6'}CHO$ employing a catalyst such as propionic acid or trichloroacetic acid at room temperature to about 118° C. The resulting Compound 22 has $R^{6'}$ substitution through a carbon atom at the 6-position. Subsequently, a reductive deoxygeneation is carried out on Compound 22 employing t—$BuNH_2$—$BH_3$ and $AlCl_3$ in dichloromethane of 0° C. to room temperature to produce Compound 23 having preferred 6-position substitution. $R^{6'}$, similarly to $R^{2'}$ above, is the residue of $R^6$ minus the alpha carbon where such exists in $R^6$. In clarification, $R^{6'}CH_2$— is a species of $R^6$.

The synthesis of Flow Sheet E can be modified to improve yield or increase the scope of its application. For example, persons skilled in the art will readily understand that aldehydes of the formula —O—CHO or —S—CHO where a hetero atom is attached directly to the aldehyde function would produce the desired Compound 22 in poor yield. In other words, Flow Sheet E as shown would not be preferred to produce an $R^6$ having —O— or —S— attached directly to the alpha carbon. Thus, Flow Sheet E might be modified by utilizing $CH_2O$ as the aldehyde in the boron assisted electrophilic substitution and treating with $H_2O_2$ and a base to produce —$CH_2OH$ as $R^6$. This —$CH_2OH$ substitution can be easily elaborated to produce a wide range of $R^6$ where —O— or —S— is attached to the alpha carbon.

Another modification of Flow Sheet E will produce 4-position substitution rather than the 6-position substitution as shown. Where the 2-position and 3-position carbons of Compound 14 are unsaturated, then the boron assisted electrophilic substitution will substitute the 4-position rather than the 6-position. A direct approach to utilize this fact would be to take Compound 14 from whatever source and insert unsaturation and remove unsaturation between the 2- and 3-position carbons as necessary to obtain the 4-position substitution. Another option would be to modify the method of producing Compound 14 or Compound 4 or Compound 18 to obtain the desired unsaturation which can later be removed.

Referring to Flow Sheet F, any of Compounds 4, 14 or 18 may be employed as starting materials to produce a 4- or 6-position substitution of $R^{6*}S$—. Compound 14 is again depicted an typical.

As the first reaction of Flow Sheet F, Compound 14 is brominated to produce Compound 24 by stirring at room temperature in $CH_2Cl_2$ with $Br_2$. Using the unmodified starting materials, the yield is almost exclusively a bromine in the 6-position. Thus, the flow scheme demonstrates a 6-position substitution. However 4-position substitution can be obtained by protecting the 6-position with a group unreactive to bromine. For Example Flow Sheet D substitutes the 6-position with an allyl or Flow Sheet H substitutes the 6-position with t-butyl. In either case, an analogous Compound 24 would be brominated in the 4-position and further substitution made thereon.

With bromine in the 6-position, the 5-position hydroxy of Compound 24 should be protected from subsequent necessary reactions. This may be accomplished by refluxing Compound 24 in acetone with potassium carbonate and benzyl bromide to produce protected Compound 25. Protected Compound 25 may be subjected to a two-step reaction to produce desired 6-position substitution. The first step is the reaction with t-butyl lithium in THF at $-78°$ C. The second step is to add $R^{6*}SCl$ to produce Compound 26 having $R^{6*}S$— as the 6-position substituent. $R^{6*}$is, of course, a moiety which joins with —S— to produce a subgeneric group of $R^6$. Compound 26 is easily deprotected to produce the desired benzofuran 27.

Thus, 4- or 6-position $R^{6*}S$— substitution may be obtained by first producing the desired substitution in the form of $R^{6*}SCl$ and subsequently performing the substitution as shown in Flow Sheet F. Suitable $R^{6*}SCl$ are PhSCl, $PYRID^4$-SCl, BENIMID-SCl, etc. Manufacture of $R^{6*}SCl$ might be by treatment of corresponding thiolate with $Cl_2$, ClBr or ClI or by other well known methods.

Referring to Flow Sheet G, any of Compounds 4, 14 or 18 may be employed as starting materials to produce a 4- or 6-position substitution of $R^{6\sim}O$— or $R^{6\#}O$—. Compound 14 is depicted as representative.

As the first reaction of Flow Sheet G, Compound 14 is subjected to a boron assisted electrophilic substitution of $CH_2O$ employing a catalyst such as propionic acid or trichloroacetic acid in refluxing toluene. The resultant Compound 28 has a boron containing fused ring joined at the 5-and 6-position of the benzofuran. With unmodified Compound 14 as the starting material, substitution will be almost exclusively on the 6-position as shown. Substitution on the 4-position may be obtained, as explained in regard to Flow Sheet E, where the boron assisted electrophilic substitution is carried out on an analogous Compound 14 starting material having unsaturation between the 2- and 3-position carbons. Also as explained, this unsaturation might be obtained by known methods and also removed by known methods to produce the desired 4-position substitution.

Subsequent to forming the fused ring of Compound 28 through the boron assisted electrophilic substitution, the fused ring is removed by reaction with $H_2O_2$ and NaOH to produce a 5-hydroxy-6-hydroxymethyl Compound 29. Subsequently, the 5-hydroxy of Compound 29 is protected by reaction with benzyl bromide and potassium carbonate in refluxing acetone to produce protected Compound 30. With the 5-position hydroxy protected with benzyl, the 6-position hydroxymethyl of Compound 30 is converted to an aldehyde by reaction of Compound 30 with $MnO_2$ in ethyl acetate. The resultant Compound 31 having a 6-position formyl may be converted to a 6-position ester through a Baeyer-Villiger Rearrangement with a peracid. Specifically Compound 31 is reacted in such a rearrangement with metachloroperbenzoic acid to produce a 6-position formate Compound 32. Subsequently, Compound 32 is hydrolysed by reaction with sodium hydroxide in methanol to produce the 6-hydroxy Compound 33.

From Compound 33, different routes are necessary to produce various types of $R^6$ substitution. Where $R^6$ is aliphatic in character and specifically, where $R^6$ is $R^{6\sim}O$— selected from for example $(C_{1-6}alkyl)$—O—, $(R^{6c})_2NC(O)$—$(C_{1-6}alkyl)$—O—, or $R^{6c}O(O)C$—$(C_{1-6}alkyl)$—O— then a one step reaction is employed. In this reaction, Compound 33 is allowed to react with $R^{6\sim}Br$ and NaH in DMF to produce Compound 34 having $R^{6\sim}O$— in the 6-position. $R^{6\sim}$ is the residue of $R^6$ absent the —O— where such is present in $R^6$ and which contains substituted or unsubstituted aliphatic hydrocarbon. $R^{6\sim}Br$ may be manufactured by methods well known to the art. Where $R^6$ is aromatic in character, and specifically where $R^6$ is $R^{6\#}O$— selected from, for example, $(C_{2-6}alkenyl)$—O—, $(Y^6)_7$ substituted naphthyl)—$(C_{1-6}alkyl)_p$—, $(Y^6)_5$ substituted phenyl)—$(C_{1-6}alkyl)_p$— etc, then a multi-step reaction is employed. In the case of multi-step reaction, Compound 33 is first reacted with cesium carbonate in methanol, followed by stripping the methanol and finally by reacting with $[(R^{6\#})_2I]^+$ $Cl^-$ in DMF to produce $R^{6\#}O$— in the 6-position of Compound 35. $R^{6\#}$ is the olefinic or aromatic equivalent of $R^{6\sim}$ above. The reactant, $[(R^{6\#})_2I]^+$ $Cl^-$, may be made by methods known to thse skilled in the art and specific reference is made to Beringer, et al., J. Am. Chem. Soc., Vol. 75, pp 2705-2708 (1953) which teaches the manufacture of these compounds.

Both Compounds 34 and 35 are subsequently deprotected to obtain the desired 5-position hydroxy as shown in Compound 36. The $R^6$ of Compound 36 is generic to both $R^{6\sim}O$— and $R^{6\#}O$—.

Referring to Flow Sheet H, the 7-position of any of Compounds 4, 14 and 18 may be substituted in a one-step reaction. For example, Compound 14 is reacted with $R^7Cl$ and with any of several acids, including $H_2SO_4$ to produce Compounds 37 and 38. Compounds 37 and 38 have $R^7$ substitution in the 6- and 7-positions respectively. Of course where the 6-position is substituted by a reaction already described then $R^7$ will substitute the 7-position exclusively. Suitable $R^7Cl$ include t-butyl-Cl, Cl₂, allyl-Cl, propyl-Cl, etc. The manufacture of $R^7Cl$ is well known in the art.

Referring to Flow Sheet I, Compound 14 is depicted as a starting material in another reaction scheme to obtain $R^4$ or $R^6$ substitution analogous to Flow Sheet E. The $R^6$ isomer is highly favored and is shown. The $R^4$ isomer may be obtained in much greater yield as above where the 2-position and 3-position carbons are unsaturated. As a first step of this reaction scheme, Compound 14 is reacted with ethyl magnesium bromide at 0° C. for about ½ hour and then the aldehyde $R^{6'}CHO$ is added to produce the phenol alcohol 39. $R^{6'}$ is defined above and is, as stated, $R^6$ absent the alpha-carbon for those $R^6$ having an alpha-carbon. The phenol alcohol 39 is subsequently converted to the dimesylate by treating with methane sulfonylchloride and triethylamine in THF at −70° C. to room temperature. The isolated dimesylate may be easily converted to compound 40 by treatment with lithium aluminum hydride in THF.

Referring to Flow Sheet J, Compound 25 of Flow Sheet F is employed as a starting material in a reaction scheme to obtain direct substitution of an unsaturated ring, $R^{64R}$, at the 6-position. As a first step, $R^{64R}$-boronic acid, tetrakis triphenyl phosphine palladium, and 2N aqueous sodium carbonate is refluxed in toluene with Compound 25 to produce a protected compound 41. The protecting group is easily removed in a second step with acetic acid and HCl to produce Compound 41. Suitable $R^{64R}$ include the unsaturated rings of $R^{6a}$ which include the phenyl, naphthyl, 5-membered heterocycle, 6-membered heterocycle, fused 5-membered heterocycle, and fused 6-membered heterocycle. Specific $R^{64R}$ include —Ph, —PYRID⁴, PYRID², PYRIM, TETR, MTETR, BENTHIA, BENIMID, NAPT, QUINA, QUINB, etc. The $R^{64R}$-boronic acid may be made by well known methods including quenching of the corresponding organomagnesium or organometallic with $BX_3$ [X=OCH₃, Cl, Br] then aqueous hydrolysis.

For the treatment of inflammation, arthritic conditions, psoriasis, asthma, or other diseases mediated by leukotrienes, a compound of formula (I) may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscluar, intravascular injection or infusion techniques. In addition to the treatment of warm-blooded animals such as mice, rats, horses, cattle, sheep, dogs, cats, etc., the compoundspof the invention are effective in the treatment of humans.

The pharmaceutical compositions containing the active ingredient may be in a form suitable for oral use, for example, as tablets, troches, lonzenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelation or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl disterate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example, sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example, polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide with partial ester derived from fatty acids and hexitol anhydrides, for example, polyoxyethylene sorbitan monooleate. The said aqueous suspensions may also contain one or more preservatives, for example, ethyl, or n-propyl p-hydroxybenzoate.

Oily suspension may be formulated by suspending the active ingredient in a vegetable oil, for example, arachis oil, olive oil, sesame oil or coconut oil, or in a mineral oil such as liquid paraffin. The oily suspensions may contain a thickening agent, for example, beeswax, hard paraffin or cetyl alcohol. These compositions may be preserved by the addition of an antioxidant such as ascorbic acid.

Dispersible powders and granules are suitable for the preparation of an aqueous suspension by mixing them with water. They provide the active ingredient in admixture with a dispersing or wetting agent, a suspending agent and one or more preservatives. Suitable dispersing or wetting agents and suspending agents are exemplified by those already mentioned above.

The pharmaceutical compositions of the invention may also be in the form of oil-in-water emulsions. The oily phase may be a vegetable oil, for example, olive oil or arachis oils, or a mineral oil, for example, liquid paraffin or mixtures of these. Suitable emulsifying agents may be naturally occurring gums, for example, gum acacia or gum tragacanth, naturally-occurring phosphatides, for example, soy bean, lecithin, and esters or partial ester derived from fatty acids and hexitol anhydrides, for example, sorbitan mono-oleate, and condensation products of the said partial esters with enthylene oxide, for example, polyoxyethylene sorbitan monooleate.

An ointment containing the pharmaceutical compositions of the present invention may be prepared, among other methods known in the art, by combining the active ingredient with a medium consisting of a glycol, a lower alkanol, and water; a gelling agent; and optionally an adjuvant such as diisopropyl adipate, diethyl sevacate, ethyl carproate and ethyl laurate. Suitable glycols include propylene glycol, butylene glycol, polyethylene glycol and the like. Generally, a carboxyvinyl polymer preneutralized with an organic amine such as diisopropyl amine and triethylamine, or a cellulose, e.g., hydroxyethyl cellulose, methyl cellulose, carboxymethyl cellulose, hydroxypropyl cellulose, is used as the gelling agent.

The compounds of the invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Dosage levels of the order to 0.2 mg to 140 mg per kilogram of body weight per day are useful in the treatment of the above-indicated condition (10 mg to 7 gms per patient per day). For example, inflammation is effectively treated by the administration from about 0.5 to 50 mg of the compound per kilogram of body weight per day (25 mg to 5 gms per patient per day).

The amount of active ingredient that may be combined with the carrier materials to produce a single dosage will vary depending upon the host treated and the particular mode of administration. Dosage unit forms will generally contain from about 25 mg to about 1 g of active ingredient.

It will be understood, however, that the specific dose level for any particular patient will dependupon a variety of factors including the activity of the specific compound employed, the age, body weight, general health, sex, diet, time of administration, route of administration, rate of excretion, drug combination and the severity of the particular disease undergoing therapy.

The following examples illustrate the preparation of the compounds of the formula (I) and as such are not to be considered as limiting the invention set forth in the claims appended hereto.

EXAMPLE 1

Four Step Synthesis of 5-hydroxy-2-(2-phenylethyl)-2,3-dihydrobenzofuran

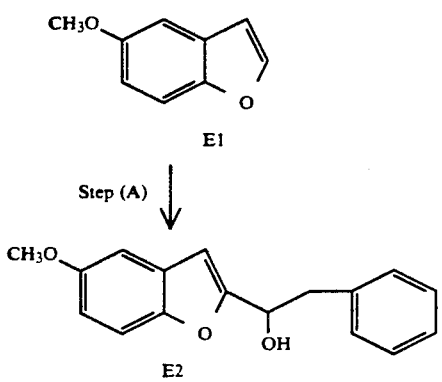

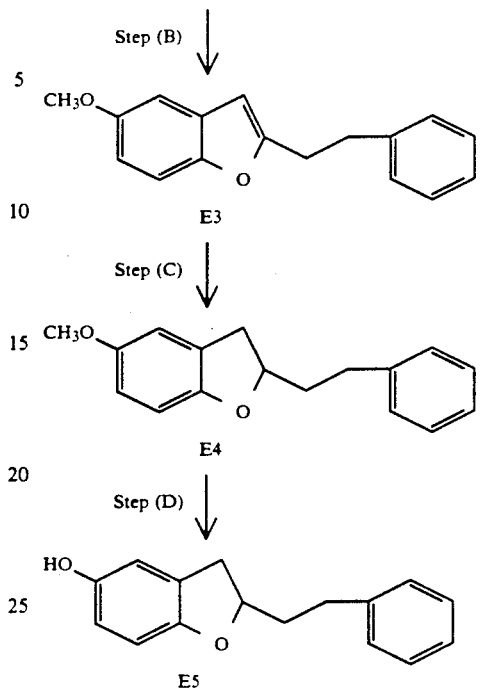

Step (A)

Preparation of 2-(1-hydroxy-2-phenyl)ethyl-5-methoxy-benzofuran, E2

To a solution of 5-methoxybenzofuran, E1, (148 gm; 1 mole) in tetrahydrofuran (2 L) at $-78°$ C. was added dropwise 2.5 molar n-butyllithium in hexane (420 mL; 1.05 moles). The mixture was stirred at $-78°$ C. for 1.5 hours and then phenyl acetaldehyde (144 gm; 1.2 moles) was added over 15 minutes. The cooling bath was removed and the mixture permitted to gradually rise to 0° C. Water (600 mL) was added. The ether layer was separated, dried over $MgSO_4$, filtered and concentrated in vacuo. The crude was chromatographed in silica gel (2 Kg) using a solvent mixture of increasing polarity of 5%, 10%, 20% and 30% ethylacetate in hexane to obtain 243 gm (90%) of 2-(1-hydroxy-2-phenyl)ethyl-5-methoxybenzofuran, E2 m.p. 69°-70° C.

Anal. Calc'd. for $C_{17}H_{16}O_3$: C, 76.09; H, 6.01. Found: C, 76.17; H, 6.12.

Step (B)

Preparation of 2-(2-phenylethyl)-5-methoxybenzofuran, E3

To a mixture aluminium chloride (204 gm; 1.5 moles) in toluene (2.5 L) at 5° C. and under nitrogen atmosphere was added in 50 gm portions t-butylamine borane (200 gm; 2.3 moles). After stirring for 30 minutes, a solution of 2-(1-hydroxy-2-phenyl)ethyl-5-methoxybenzofuran, E2, (238 gm; 880 mmoles) in toluene (600 mL) was added dropwise. The mixture was stirred at 5° C. for 2 hours and then added in portions to a stirring ice cold mixture of 10% hydrochloric acid (3 L). Stirring was continued until fizzing had stopped. The organic layer was separated and dried over $MgSO_4$, filtered and concentrated in vacuo. The residue was chromatographed in silica gel (2 Kg) using 15% ethyl acetate as eluent to obtain 129 gm (58%) of 2-(2-phenylethyl)-5-methoxybenzofuran, E3, m.p. 68°-70° C.

Anal. Calcd. for $C_{17}H_{16}O_2$: C, 80.92; H, 6.39. Found: C, 80.32; H, 6.84.

Step (C)

Preparation of 2-(2-phenylethyl)-5-methoxy-2,3-dihydrobenzofuran, E4

Trifluoroacetic acid (232 mL; 30 moles) was added over 15 minutes to a suspension of 2-(2-phenylethyl)-5-methoxybenzofuran, E3, (128 gm; 500 mmoles) in triethylsilane (465 mL; 2.8 moles) at 5° C. The mixture was stirred at 5° C. for 60 minutes and then at room temperature for 18 hours. The mixture was concentrated in vacuo. The residue was dissolved in diethyl ether, washed with 1N sodium hydroxide, dried over $MgSO_4$, filtered and concentrated in vacuo. The residue was chromatographed in silica gel using 5% ethyl acetate in hexane as eluent to obtain 128 gm (99%) of 2-(2-phenylethyl)-5-methoxy-2,3-methoxybenzofuran, E4.

Anal. Calcd. for $C_{17}H_{18}O_2$: C, 80.28; H, 7.13. Found: C, 80.61; H, 7.56.

Step (D)

Preparation of 5-hydroxy-2-(2-phenylethyl)-2,3-dihydrobenzofuran, E5

Ethanethiol (62 gm; 1 mole) was added dropwise to lithium hydride (8 gm; 1 mole) in dimethylformamide (700 mL) under nitrogen atmosphere. 2-(2-phenylethyl)-5-methoxy-2,3-dihydrobenzofuran, E4, (126 gm; 500 mmoles) in dimethylformamide (200 mL) was then added in one portion and the mixture brought to reflux for 3 hours. The mixture was poured into 1N hydrochloric acid and extracted with diethyl ether. The ether layer was separated and backwashed with water twice, dried over $MgSO_4$, filtered and concentrated in vacuo to obtain 123 gm (98%) of 5-hydroxy-2-(2-phenylethyl)-2,3-dihydrobenzofuran, E5, m.p. 56°-58° C.

Anal. Calcd. for $C_{16}H_{16}O_2$: C, 79.97; H, 6.71. Found: C, 79.44; H, 6.52.

EXAMPLE 2

Two Step Synthesis of 4 or 6-allyl-5-hydroxy-2-(2-phenylethyl)-2,3-dihydrobenzofuran

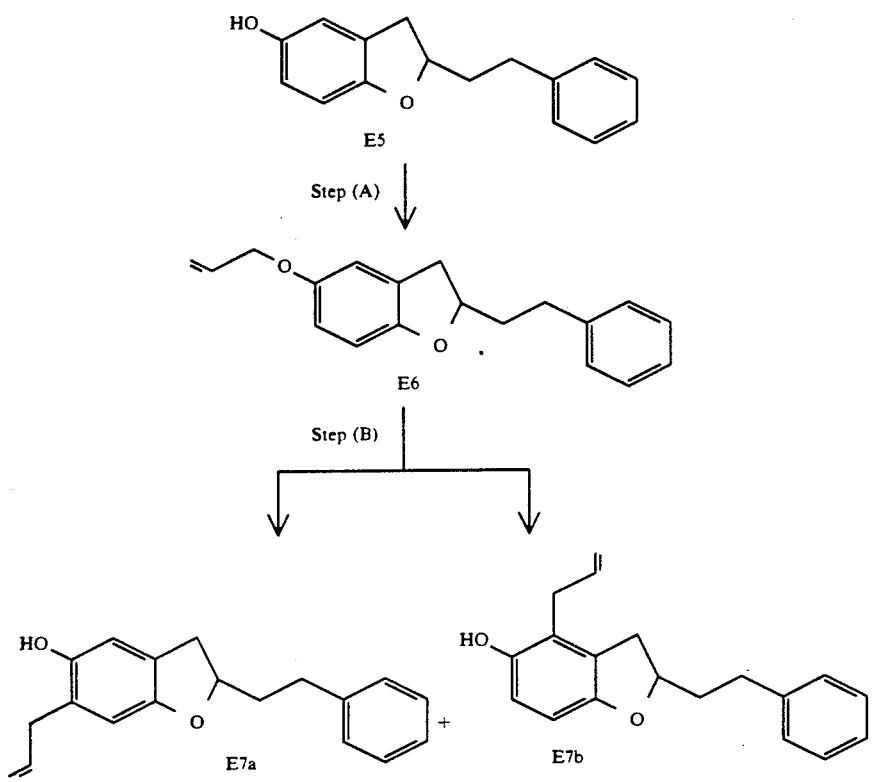

Step (A)

Preparation of 5-allyloxy-2-(2-phenylethyl)-2,3-dihydrobenzofuran, E6

A mixture 5-hydroxy-2-(2-phenylethyl)-2,3-dihydrobenzoruan, E5, (50 gm; 208 mmoles), potassium carbonate (55 gm; 400 mmoles), allyl bromide (48 gm; 400 mmoles) and acetone (500 mL) was refluxed for 18 hours. The mixture was cooled, diluted with hexane (250 mL) and filtered through celite. The filtrate was concentrated in vacuo and the residue chromatographed in silica gel using 10% ethylacetate in hexane as eluent to obtain 47.8 gm (82%) of 5-allyloxy-2-(2-phenylethyl)-2,3-dihydrobenzofuran E6 as an oil.

Step (B)

Preparation of
6-allyl-5-hydroxy-2-(2-phenylethyl)-2,3-dihydrobenzofuran and
4-allyl-5-hydroxy-2-(2-phenylethyl)-2,3-dihydrobenzofuran, E7 a+b A mixture of 5-allyloxy-2-(2-phenylethyl)-2,3-dihydrobenzoruan, E6, (47 gm; 167 mmoles) in 1,2-dichlorobenzene (100 mL) was refluxed under nitrogen atmosphere for 21 hours. The mixture was concentrated in vacuo to drive off most of the 1,2-dichlorobenzene and the residue was chromatographed on silica gel using 10% ethylacetate in hexane as eluent to obtain 41 gm (87%) of pure isomer mixture. The isomer mixture was separated by chromatography on silica gel (2.5 Kg) using 50% hexane in dichloromethane as eluent to obtain 6-allyl-5-hydroxy-2-(2-phenylethyl)-2,3-dihydrobenzofuran, E7a, 32.7 gm (69.5%), m.p. 79°-80° C. and 4-allyl-5-hydroxy-2-(2-phenylethyl)-2,3-dihydrobenzofuran, E7b, as an oil 10.4 gm (22%).

EXAMPLE 3

Five Step Synthesis to
2-(2-p-chlorophenylethyl)-5-hydroxy-2,3-dihydrobenzofuran

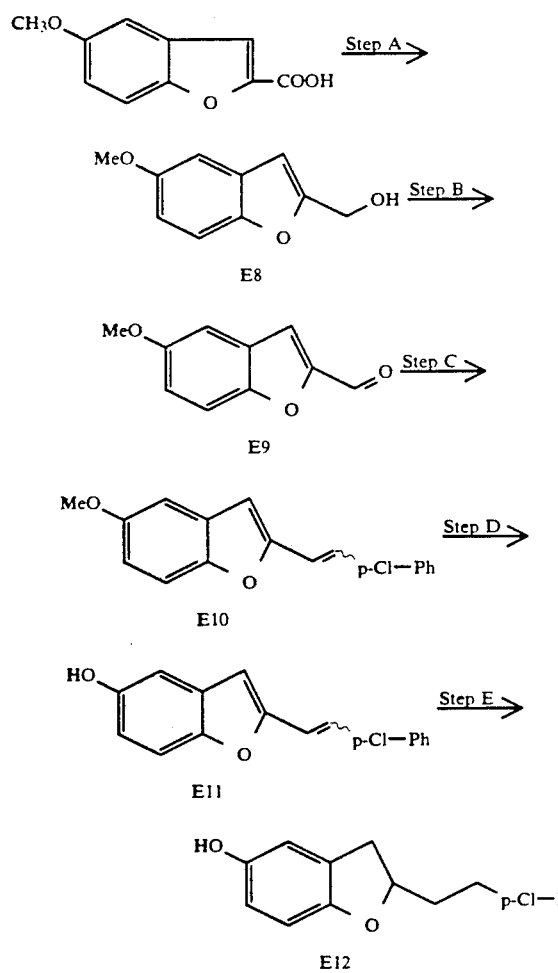

Step (A)

5-methoxy-2-hydroxymethylbenzofuran, E8

To a solution of 5 methoxybenzofuran-2-carboxylic acid (10.0 gm; 52 mmoles) in THF (300 mL) cooled at −78° C. was added diisobutylaluminium hydride (120 ml, 182 mmoles) via a syringe. The reaction mixture temperature was raised to room temperature and the solution was stirred for 3 hours. The mixture was poured into a saturated solution of ammonium chloride (500 ml) and stirred 15 minutes then was acidified with HCl 6N. This mixture was extracted with ethyl acetate (2×500 ml). The combined organic extract was concentrated in vacuo. The residue was chromatographed on silica gel using 30% ethyl acetate in hexane to yield 5-methoxy-2-hydroxymethylbenzofuran, E8, (6.5 gm, 71%).

Step (B)

5-methoxybenzofurancarboxaldehyde, E9

To a solution of 5-methoxy-2-hydroxymethylbenzofuran (16.0 gm; 90 mmoles) in ethyl acetatel (1 L) was added MnO2 (78 gm, 900 mmoles). The reaction mixture was stirred at room temperature for 3 hours. Then this suspension was filtered through celite and concentrate in vacuo. The filtrate yielded the title Compound E9, (9.5 gm, 60%).

$^1$H NMR w: 3.85 (s, 3H); 7.15 (m, 2H); 7.45 (m, 2H, olefinic +1 aromatic); 9.8 (s, 1H aldehyde portion).

Step (C)

2-(2-p-chlorostyryl)-5-methoxybenzofuran, E10

To ethanol (50 ml) was added Na (2.58 gm, 0.112 mole) portion wise at room temperature. The mixture was stirred until the sodium was completely dissolved. To this 0° C. cooled solution, was added p-chlorobenzyl triphenylphosphonium chloride (45.6 gm, 0.108 mole) and stirred for 30 minutes. To this phosphorane was added 5-methoxy-benzofuran-2-carboxaldehyde, E9, (9.5 gm, 54 mmole) as a reactant and the reaction mixture was stirred at 0° C. for 3 hours. The mixture was acidified with HCl 1N and concentrated in vacuo. The residue was chromatographed on silica gel using 5% ethyl acetate in hexane to yield 6.5 gm, 41%, E10.

$^1$H NMR w: 3.75 (2s, 3H, cis, trans mixture); 6.45 (m, 2H, olefinic proton); 6.7-7.0 (m, 2H); 7.1-7.5 (m, 6H).

Step (D)

2-(2-p-chlorostyryl)-5-hydroxybenzofuran, E11

To a solution of E10 (6.5 gm, 22.8 mmoles) in CH2Cl2 (500 ml) cooled at −78° C. was added BBr3 (68.5 ml, 68.5 mmole) via a syringe. The reaction mixture was stirred for 1 hour at −78° C., and then added dropwise to methanol (150 ml) at room temperature. The methanol mixture was concentrated in vacuo. The residue was chromatographed on silica gel using 15% ethyl acetate in hexane to yield 4.7 g, 76%, E11.

$^1$H NMR w: 6.5-7.5 (m,10H, complex aromatic proton pattern); 7.9 (s, 1H, hydroxy, exchangeable).

Step (E)

2-(2-p-chlorophenylethyl)-5-hydroxy-2,3-dihydrobenzofuran, E12

To a solution of E11 (4.65 or 17.2 mmoles) in TFH (25 ml) was added triethyl silane (8.23 ml, 51.6 mmoles) as a reactant. The resultant reaction mixture was stirred at room temperature for 1 hour. The reaction mixture was diluted with H2O then neutralized with potassium carbonate (solid), extracted with ethyl acetate (100 ml×2), dried Na2SO4 and concentrated in vacuo. The residue was chromatographed on silica gel. Elution with 10% ethyl acetate in hexane yielded 2.5 gm, 53% of E12.

1H NMR w: 1.65-2.2 (m, 2H); 2.5-2.9 (q, 3H, 1 benzylic proton +2 phenylethyl methylene); 3.2 (q, 1H, benzylic proton); 4.7 (m, 1H, methyne); 4.8 (s, 1H, hydroxy proton); 6.6 (s, 3H); 7.2 (q, 4H, p-chloro benzene protons).

EXAMPLE 4

Two Step Synthesis to 2-(2-p-chlorophenylethyl)-5-hydroxy—(4 or 6)-allyl-2,3-dihydrobenzofuran

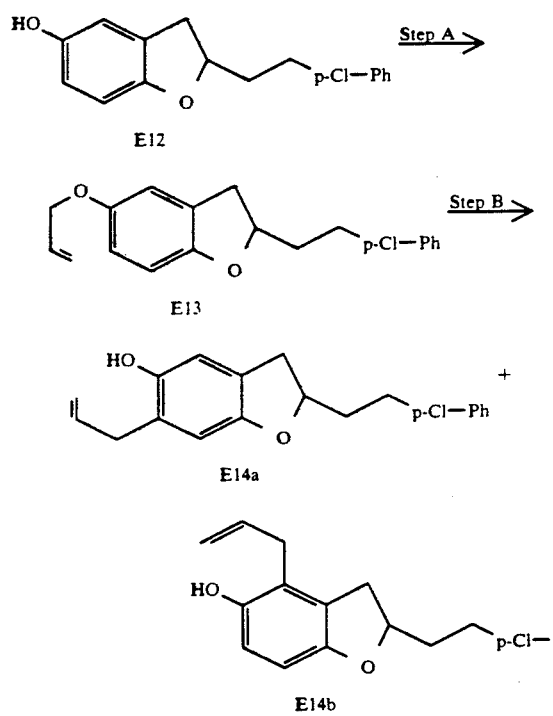

Step (A)

2-(2-p-chlorophenylethyl)-5-allyloxy-2,3-dihydrobenzofuran, E13

A mixture of E12 (2.5 gm, 9.15 mmoles), potassium carbonate (6 gm, 43 mmoles), allyl bromide (4 ml, 23.5 mmoles) was refluxed in acetone for 2 hours.

The reaction mixture was cooled, filtered through celite and concentrated in vacuo. The residue was chromatographed on silica gel using 5% ethyl acetate in hexane as eluent to yield (2.4 gm, 86%) of E13.

1H NMR w: 1.7-2.0 (m, 2H); 2.55 2.9 (m, 3H); 3.15 (q, 1H, benzylic proton); 4.35 (d, 2H methylene proton); 4.65 (m, 1H, methyne); 5.2 (m, 2H, olefinic); 5.9 (m, 1H); 6.65 (m, 3H, aromatic); 7.15 (q, 4H).

Step (B)

2-(2-p-chlorophenylethyl)-5-hydroxy-(4 or 6)-allyl-2,3-dihydrobenzofuran, E14 a+b A solution of E13 (2.4 gm, 7.6 mmoles) in orthodichlorobenzene (10 mL) was refluxed under nitrogen for a period of 10 hours. After cooling, the reaction mixture was chromatographed as such on silica gel. Eluting with 15% ethyl acetate in hexane yielded 1.5 gm, 62.5% of the 6-isomer, E14a, and the 4-isomer, E14b.

1H NMR w: 2.0 (m, 2H); 2.75 (m, 3H); 3.1 (m, 1H,); 3.3 (d, 2H, methylene); 4.55 (s, 1H, hydroxy); 5.65 (m, 1H, methyne); 5.1 (d, 2H, olefinic); 6.0 (m, 1H); 6.5 (s, 1H, H7); 6.65 (s, H, H4); 7.1 (m, 4H, p-chlorophenyl aromatic).

EXAMPLE 5

Three Step Synthesis to 2-(2-p-chlorophenylethyl)-6-(3-hydroxypropyl)-5-hydroxy-2,3-dihydrobenzofuran, E17

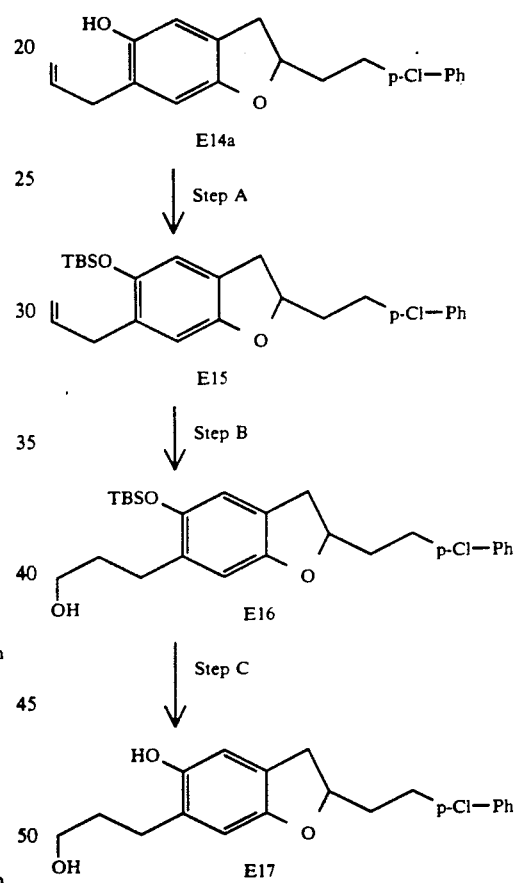

Step (A)

2-(2-p-chlorophenylethyl)-5-tertbutyldimethylsilyloxy-6-allyl-2,3-dihydrobenzofuran, E15

To a solution of E14a, (1.5 gm, 4.8 mmoles) in CH2Cl2 (20 ml) was added 4-(dimethylamino) pyridine (0.3 gm, 2.4 mmoles) triethylamine (0.66 gm, 4.8 mmoles) tert-butyldimethylchlorosilane (0.72 gm, 4.8 mmole) the reaction mixture was stirred at room temperature overnight.

The reaction mixture was concentrated in vacuo. The residue was chromatographed on silica gel using 5% ethyl acetate in hexane as eluent yielded E15 2 gm or 97%.

Step (B)

2-(2-p-chlorophenylethyl)-6-[3-hydroxy-propyl]5-tert-butyldimethylsilyloxy-2,3-dihydrobenzofuran, E16

To a solution of E15, (2.0 gm, 4.6 mmoles) in THF at 0° C. was added dropwise borane (14.37 mL, 14 mmole) and the reaction mixture was stirred for 2 hours. To the reaction mixture was subsequently added trimethylamine-N-oxide (2.15 gm, 19.4 mmoles) and the mixture was refluxed for 8 hours. The reaction mixture was concentrated in vacuo. The residue was chromatographed on silica gel using 30% ethyl acetate in hexane as eluant to yield 1.4 gm 67%) of E16.

$^1$H NMR w: 0.15 (s, 6H); 0.95 (s, 9H, tertbutyl); 1.6–2.2 (m, 4H); 2.45–2.95 (m, 5H); 3.15 (q, 1H, benzylic proton); 3.55 (d, J=6 Hz, 2H); 4.65 (m, 1H, methyne); 6.5 (d, 2H, H$_4$, H$_7$); 7.15 (q, 4H).

Step (C)

2-(2-p-chlorophenylethyl)-6-(3-hydroxypropyl)-5-hydroxy-2,3-dihydrobenzofuran, E17

To a solution of E16, 1.5 gm (3.3 mmoles) in tetrahydrofuran (20 mL) at 0° C. was added tetrabutylammonium fluoride (3.3 mL, 3.3 mmole) and the mixture was stirred for 1 hour. The reaction mixture was quenched with pH7 buffer and extracted twice with 15 mL EtOAc and the combined organic layers were evaporated in vacuo. The residue was chromatographed on silica gel and eluted with 30% ethyl acetate in hexane as eluant to yield 0.9 g or 81% of title compound E17.

$^1$H NMR w: 1.6–2.1 (m, 4H); 2.4–2.9 (m, 5H); 3.1 (q, 1H, benzylic proton); 3.5 (t, J=6H, 2H); 4.45 (m, 1H, methylene); 6.4 (s, 1H, H$_7$); 6.58 (s, 1H, H$_4$); 7.15 (s, 4H, p-chlorophenyl proton).

EXAMPLE 6

Four Step Synthesis to 2-(2-p-chlorophenylethyl)-6-(3-phenoxypropyl)-5-hydroxy-2,3-dihydrobenzofuran, E21

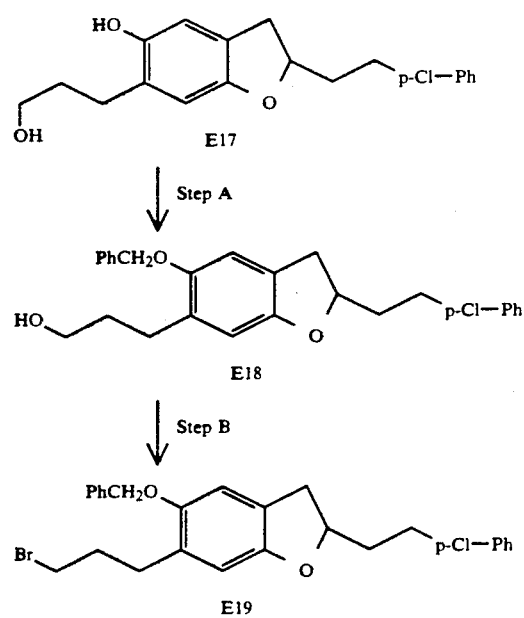

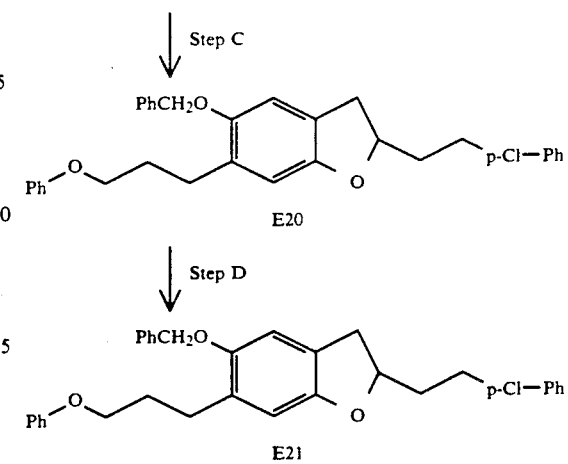

Step (A)

2-(2-p-chlorophenylethyl)-6-(3-hydroxypropyl)-5-benzyloxy-2,3-dihydrobenzofuran, E18

A mixture of E17 (1 gm, 3 mmoles), potassium carbonate (0.84 gm, 6 mmoles) benzyl chloride (0.76 gm, 6 mmoles) in acetone (25 mL) was refluxed for a period of 18 hours. The reaction mixture was cooled, filtered through celite and concentrated in vacuo. The residue was chromatographed on silica gel using 10% ethyl acetate in hexane as eluant to yield 0.9 gm (70.4%) of E18.

$^1$H NMR w: 1.75–2.2 (m, 4H); 2.6–2.9 (m, 5H); 3.15 (dd, J=8 Hz, J=16 Hz); 3.5 (t, 2H); 4.75 (m, 1H, methyne); 5 (s, 2H); 6.6 (s, 1 H$_7$); 6.8 (s, 1H, H$_4$); 7.15 (d, J=9 Hz, 2H); 7.27 (d, J=9 Hz, 2H); 7.4 (m, 5H).

Step (B)

2-(2-p-chlorophenylethyl)-6-(3-bromopropyl)-5-benzyloxy-2,3-dihydrobenzofuran, E19

To a solution of E18, (0.9 gm, 2.1 mmoles) in CH$_2$Cl$_2$ (20 mL) was added triphenylphosphine (1.12 gm, 4.27 mmoles) and carbon tetrabromide, (1.41 gm, 4.25 mmole). The resulting mixture was subsequently stirred for 15 minutes at room temperature. The reaction mixture was chromatographed as such on silica using first hexane, then 5% ethyl acetate in hexane as eluent yielded title compound E19 1.03 gm (100%).

$^1$H NMR w: 1.9–2.4 (m, 4H); 2.7–3 (m, 5H); 3.25 (q, 1H); 3.45 (t, J=6 Hz, 2H); 4.8 (m, 1H); 5.05 (s, 2H, methylene oxy); 6.7 (s, 1H, H$_4$); 6.85 (s, 1H H$_7$); 7.3 (m, 4H, p-chlorophenyl proton); 7.45 (s, 5H).

Step (C)

2-(2-p-chlorophenylethyl)-6-(3-phenoxypropyl)-5-benzyloxy-2,3-dihydrobenzofuran E20

To a solution of phenol (0.360 gm, 3.8 mmoles) in DMF (15 mL) was added NaH (0.092 gm, or 4 mmoles). After stirring for 1 hour, a solution of E19 (1.17 gm, 2.4 mmoles) in DMF (5 mL) was added and stirred at room temperature for 1 hour. The solution was diluted with brine and extracted with ether. The organic phase was washed with water, dried (Na$_2$SO$_4$), and concentrated in vacuo. The residue was chromatographed on silica gel. Elution with 5% ethyl acetate in hexane yielded 0.85 gm (70.8%) of title compound E20.

¹H NMR w: 1.8–2.2 (m, 4H); 2.6–3.0 (m, 5H); 3.2 (s, 1H, benzylic proton); 3.95 (t, J=6 Hz, 2H); 4.7 (m, 1H, methyne); 4.95 (s, 2H); 6.6 (s, 1H, H₄); 6.75 (s, 1H, H₇); 6.9 (m, 2H); 7.2 (m, 7H); 7.45 (m, 5H).

Step (D)

2-(2-p-chlorophenylethyl)-6-(3-phenoxypropyl)-5-hydroxy-2,3-dihydrobenzofuran, E21

To a solution of E20 (0.85 gm, 1.75 mmoles) CH₂Cl₂ (15 mL) at −78° C. was added BBr₃ (0.17 mL, 1.75 mmoles) and the resulting mixture was stirred for 5 minutes. The reaction was quenched by adding MeOH (10 mL) and a trace amount of K₂CO₃, then concentrated in vacuo. The residue was chromatographed on silica gel. Elution with 5% ethyl acetate in hexane yielded 0.56 gm or (80%) of title compound E21.

¹H NMR w: 1.6–2.2 (m, 4H); 2.5–2.85 (m, 5H); 3.1 (s, 1H); 3.9 (t, J=6 Hz, 2H); 4.6 (m, 1H, methyne); 5.2 (s, 1H, hydroxy proton); 6.5 (d, 2H, H₄, H₇); 6.8 (m, 3H); 7.1 (m, 6H, aromatic).

Anal. Calcd for C₂₅H₂₅O₃Cl: C, 73.43; H, 6.11; Cl, 8.69. Found: C, 73.77; H, 6.10; Cl, 10.46.

EXAMPLE 7

Two Step Synthesis of Intermediate 6-(3-bromopropyl)-5-benzyloxy-2-(2-phenylethyl)-2,3-dihydrobenzofuran, E88

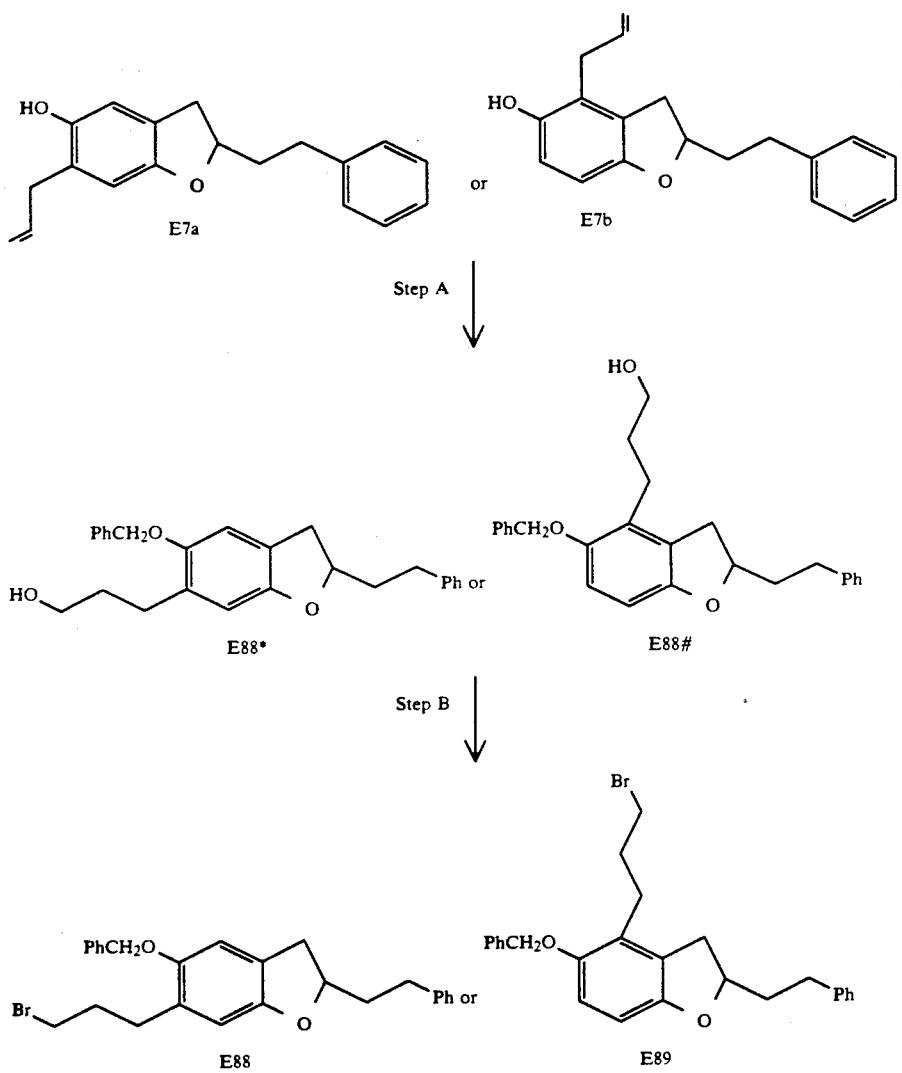

Steps (A) and (B)

In a manner analogous to the production of compound E73 from compound E71, compound E88 is produced from compound E7a and E89 from compound E7b.

EXAMPLE 8

Three Step Synthesis of
6-[3-[4-(1-H-tetrazol-5-yl)-phenoxy]propyl]-5-hydroxy-2-(2-phenylethyl)-2,3-dihydrobenzofuran, E24

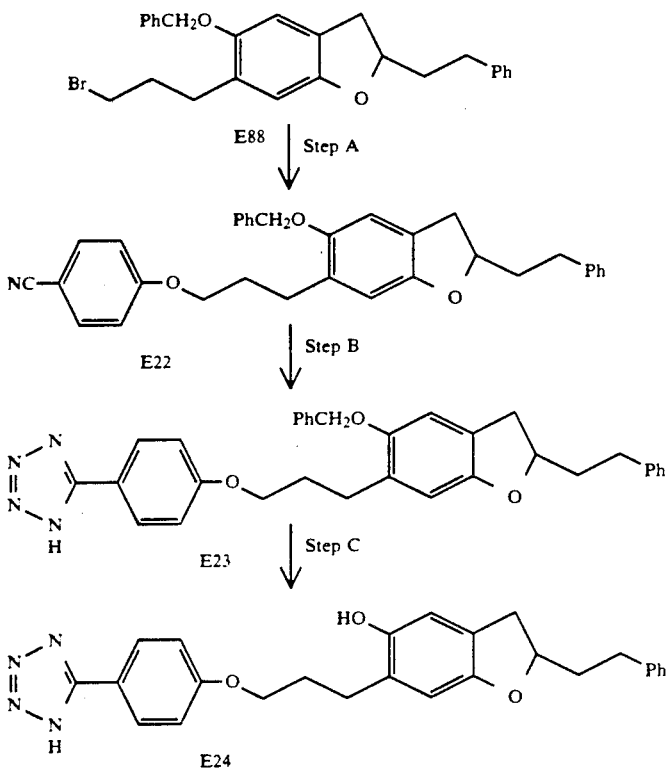

Step (A)

Preparation of
6-[3-(4-cyanophenoxy)-propyl]-5-benzyloxy-2-(2-phenylethyl)-2,3-dihydrobenzofuran, E22

4-cyanophenol (1.07 gm, 9 mmoles) was added in one portion to 50% sodium hydride dispersion (435 mgs; 9 mmoles) in dimethylformamide (30 mL) under nitrogen atmosphere. After stirring for 30 minutes, a solution of 6-(3-bromopropyl)-5-benzyloxy-2-(2-phenylethyl)-2,3-dihydrobenzofuran, E88, (1 gm, 2.2 mmoles) in dimethylformamide (5 mL) was added. The mixture was stirred at room temperature for 18 hours. The mixture was poured into excess 20% citric acid solution and extracted with diethyl ether. The ether layer was backwashed with water, dried (MgSO$_4$), filtered and concentrated in vacuo. The residue was chromatographed in silica gel using 15% ethylacetate in hexane as eluent to yield 1.06 gm (95%) as an oil of 6-[3-(4-cyanophenoxy)propyl]-5-benzyloxy-2(2-phenylethyl)-2,3-dihydrobenzofuran, E22, m.p. 154°–157° C.

$^1$H NMR w: 1.88–2.25 (m, 4H), 2.67–2.95 (m, 4H), 3.22 (dd, 1H, J=15 Hz, J'=9 Hz), 3.98 (t, 2H, J=5.5 Hz), 4.67–4.83 (m, 1H), 5.0 (s, 2H), 6.62 (s, 1H), 6.79 (s, 1H), 6.85 (d, 2H, J=7.4 Hz), 7.15–7.46 (m, 10H), 7.54 (d, 2H, J=7.4 Hz).

Step (B)

Preparation of
6-{3-[4-(1H-tetrazol-5-yl)phenoxy]propyl}-5-benzyloxy-2-(2-phenylethyl)-2,3-dihydrobenzofuran, E23

A mixture of 6-[3-(4-cyanophenoxy)propyl]-5-benzyloxy-2-(2-phenylethyl)-2,3-dihydrobenzofuran E22 (1 gm, 2.0 mmoles) and tri-n-butyl tin azide (2.2 gm; 6.6 mmoles) was heated in an oil bath at 125° C. for 90 minutes. The total mixture was chromatographed on silica gel using 1:1 ethyl acetate in hexane and containing 10% acetic acid to yield 1.2 gm of 6-{3-[4-(1H-tetrazol-5-yl)phenoxy]propyl}-5-benzyloxy-2-(2-phenylethyl)-2,3-dihydrobenzofuran, E23.

$^1$H NMR w: 1.82–2.24 (m, 4H), 2.65–2.94 (m, 4H), 3.24 (dd, 1H, J=15 Hz, J'=9.3 Hz), 4.0 (t, 2H, J=7.4 Hz), 4.65–4.85 (m, 1H), 5.0 (s, 2H), 6.65 (s, 1H), 6.79 (s, 1H), 6.94 (d, 2H, J=9.3 Hz), 7.07–7.49 (m, 10H), 7.89 (d, 2H, J=9.3 Hz).

Step (C)

Preparation of
6-{3-[4-(1H-tetrazol-5-yl)phenoxy]propyl}-5-hydroxy-2-(2-phenylethyl)-2,3-dihydrobenzofuran, E24

A mixture of 6-{3-[4-(1H-tetrazol-5-yl)-phenoxy]propyl}-5-benzyloxy-2-(2-phenylethyl)-2,3-dihydrobenzofuran, E23, (450 mgs; 0.84 mmoles), 6N hydrochloric acid (2 mL) and acetic acid (18 mL) was heated in an oil bath at 125° C. for 4 hours and under nitrogen atmosphere. The mixture was concentrated in vacuo. The residue was chromatographed on silica gel using 30:70 ethylacetate in hexane and containing 5% acetic acid to yield 251 mgs (67%) of 6-{3-[4-(1H-tetrazol-5-yl-phenoxy]propyl}-5-hydroxy-2-(2-phenylethyl-2,3-dihydrobenzofuran, E24, m.p. 154°–157° C.

¹H NMR w: 1.85-2.28 (m, 4H), 2.59-2.97 (m, 4H), 3.21 (dd, 1H, J=11 Hz, J'=7.4 Hz), 4.04 (t, J=3.7 Hz), 4.64-4.83 (m, 1H), 6.58 (s, 1H), 6.65 (s, 1H), 7.03 (d, 2H).

Anal. Calcd for $C_{26}H_{26}N_4O_3 \cdot \frac{1}{2} H_2O$: C, 69.16; H, 6.02; N, 12.40. Found: C, 69.20 H; 6.38; N, 12.08.

EXAMPLE 9

Three Step Synthesis to 6-[3-(3-carboxy-2-methoxyquinolin-7-yl)thiopropyl]-5-hydroxy-2-(2-phenylethyl)-2,3-dihydrobenzofuran E27

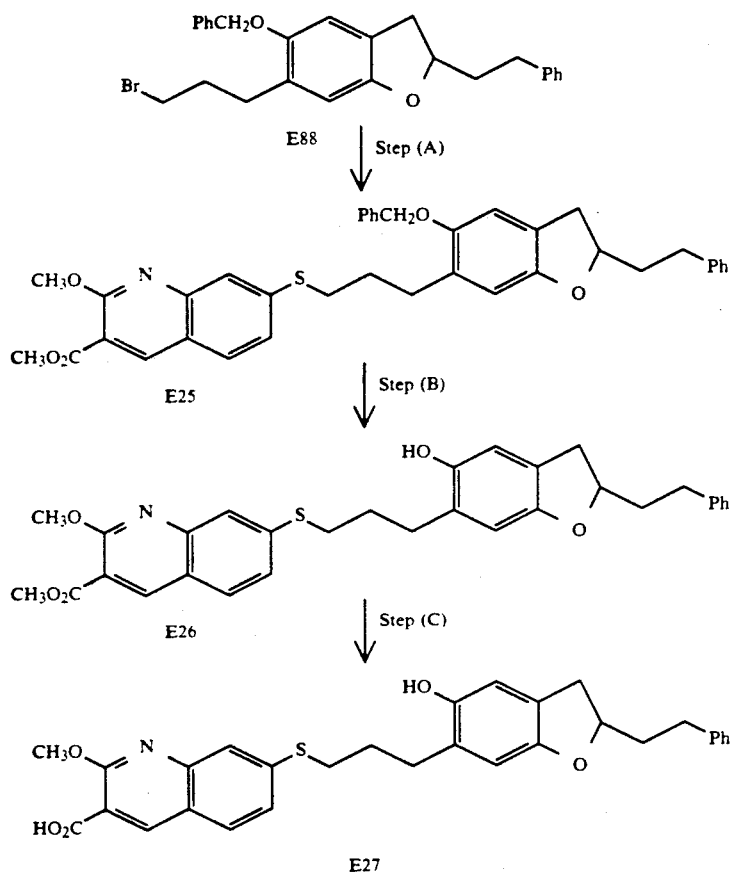

Step (A)

Preparation of 6-[3-(3-carbomethoxy-2-methoxyquinolin-7-yl)thiopropyl]-5-benzyloxy-2-(2-phenylethyl)-2,3-dihydrobenzofuran, E25

A mixture of 6-(3-bromopropyl)-5-benzyl-oxy-2-(2-phenylethyl)-2,3-dihydrobenzofuran, E88, (823 mgs; 1.8 mmols), 2-methoxy-3-carbomethoxy-7-mercaptoquinoline (700 mgs; 2.8 mmoles) and potassium carbonate (414 mgs; 3.0 mmoles) in methylethylketone (50 mL) was refluxed for a period of 60 minutes. The reaction mixture was cooled, filtered through celite and concentrated in vacuo. The residue was chromatographed on silica gel using 20% ethylacetate in hexane as eluent to yield 1.0 gm (96%) of 6-{3-[3-carbomethoxy-2-methoxyquinolin-7-yl)thiopropyl]-5-benzyloxy-2-(2-phenylethyl)-2,3-dihydrobenzofuran, E25, m.p. 96°-98°.

¹H NMR w: 1.88-2.21 (m, 4H), 1.45-1.92 (m, 4H), 3.01-3.15 (m, 2H), 3.22 (dd, 1H, J=18 Hz, J'=7.5 Hz), 3.95 (s, 3H), 4.13 (s, 3H), 4.65-4.79 (m, 1H), 5.01 (s, 1h), 6.64 (s, 1H), 6.77 (s, 1H), 7.13-7.46 (m, 11H), 7.55-7.64 (m, 2H) 8.55 (s, 1H).

Anal. Calcd. for $C_{31}H_{31}NSO_5$: C, 70.29; H, 5.89; N, 2.64; S, 6.05. Found: C, 69.91; H, 5.95; N, 2.65; S, 6.29.

Step (B)

Preparation of 6-[3-(3-carbomethoxy-2-methoxyquinolin-7-yl)thiopropyl]-5-hydroxy-2-(2-phenylethyl)-2,3-dihydrobenzofuran, E26

Methanesulfonic acid (0.5 mL) was added dropwise to a solution of 6-[3-(carbomethoxy-2-methoxyquinolin-7-yl)thiopropyl]-5-benzyloxy-2-(2-phenylethyl)-2,3-dihydrobenzofuran, E25, (1.1 gm; 1.7 mmoles), trifluoroacetic acid (11 mL) and thioanisole (3 mL) at 5° C. The mixture was stirred for 30 minutes and then added in portions to an ice cold stirring biphasic mixture of saturated sodium bicarbonate solution (150 mL), brine (25 mL), tetrahydrofurane (125 mL) and diethyl ether (25 mL). The organic layer was separated, dried (MgSO₄), filtered and concentrated in vacuo. The residue was chromatographed on silica gel using 30% ethyl acetate in hexane as eluent to yield 900 mgs (95%) of 6-[3-(3-carbomethoxy-2-methoxyquinolin-7-yl)thiopropyl]-5-hydroxy-2-(2-phenylethyl-2,3-dihydrobenzofuran, E26, that had crystallized from diethyl ether, m.p. 112°-114° C.

¹H NMR w: 1.85-2.22 (m, 4H), 2.65-2.92 (m, 4H), 3.12 (t, 2H, J=3.7 Hz), 3.21 (dd, 1H, J=15 Hz, J'=7.5 Hz), 3.94 (s, 3H), 4.16 (s, 3H), 4.48 (s, 1H, phenolic proton), 4.48–4.66 (m, 1H), 6.58 (s, 1H), 6.61 (s, 1H), 7.12–7.34 (m, 6H), 7.56–7.68 (m, 2H), 8.55 (s, 1H).

Anal. Calcd. for $C_{31}H_{31}NSO_5$: C, 70.29; H, 5.89; N, 2.64; S, 6.05. Found: C, 69.91; H, 5.95; N, 2.65; S, 6.29.

Step (C)

Preparation of 6-[3-(3-carbomethoxy-2-methoxyquinolin-7-yl)thiopropyl]-5-hydroxy-2-(2-phenylethyl)-2,3-dihydrobenzofuran, E27

A mixture of 6-[3-(3-carbomethoxy-2-methoxyquinolin-7-yl)thiopropyl]-5-hydroxy-2-(2-phenylethyl)-2,3-dihydrobenzofuran, E26, (794 mg; 1.5 mmoles), methanol (12 mL) and 1N sodium hydroxide (12 mL) was heated in an oil bath at 75° C. and under nitrogen atmosphere for 45 minutes. The mixture was concentrated in vacuo to remove most of the methanol and the residue was neutralized with excess 25% ammonium acetate solution. The mixture was extracted with ethylacetate, dried (MgSO$_4$), filtered and concentrated in vacuo. The residue was chromatographed on silica gel using 65:30:5 hexane:ethylacetate:acetic acid as eluent to yield 165 mgs (21%) of 6-[3-(3-carboxy-2-methoxyquinolin-7-yl)thiopropyl]-5-hydroxy-2-(2-phenylethyl)-2,3-dihydrobenzofuran, E27, m.p. 157°–161° C.

$^1$H NMR w: 1.77–2.27 (m, 4H), 2.65–2.94 (m, 4H), 3.06–3.27 (m, 3H), 4.25 (s, 3H), 4.62–4.79 (m, 1H), 6.56 (s, 1H), 6.68 (s, 1H), 7.10–7.36 (m, 6H), 7.62–7.73 (m, 2H) 8.78 (s, 1H).

Anal. Calcd. for $C_{30}H_{29}NSO_5$: C, 69.88; H, 5.66; N, 2.71; S, 6.21. Found; C, 70.25; H, 5.94; N, 2.24; S, 5.92.

EXAMPLE 10

Two Step Synthesis to 5-hydroxy-2-(2-phenylethyl)-6-(4-phenylbutyl)-2,3-dihydrobenzofuran

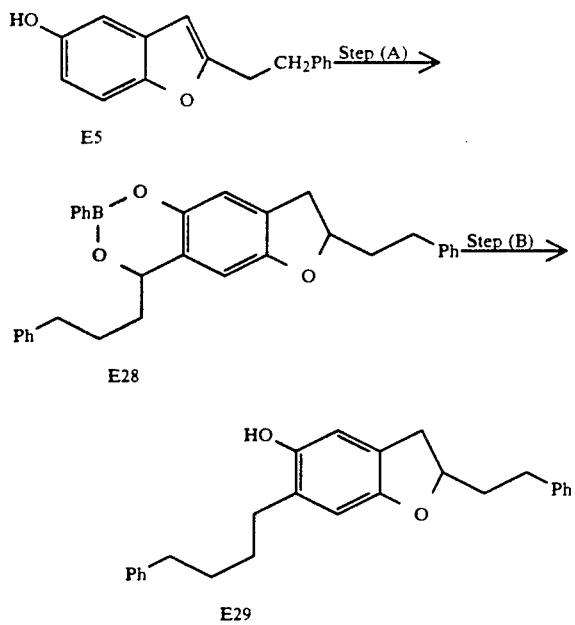

Step (A)

Preparation of 7,8-dihydro-2-(2-phenyl-7-(2-(2-phenylethyl)-4-(3-phenylpropyl)-4H-furo[2,3-g]-1,3,2-benzodioxaborin, E28

A mixture of 5-hydroxy-2-(2-phenylethyl)-2,3-dihydrobenzofuran, E5, (1.4 gm; 6 mmoles), phenylboronic acid (876 mgs; 7.2 mmoles), 4-phenylbutyraldehye (1.3 gm; 9 mmoles), trichloroacetic acid (300 mgs; 1.8 mmoles) and toluene (120 mL) was refluxed under nitrogen atmosphere for 7 hours and using a Dean Stark to collect azeotroped water. The mixture was cooled and stirred with saturated sodium bicarbonate solution. The toluene layer was separated, dried (MgSO$_4$), filtered and concentrated to obtain 3.3 gm of crude 7,8-dihydro-2-(2-phenyl-7-(2-(2-phenylethyl)-4-(3-phenyl-propyl)-4H-furo[2,3-g]-1,3,2-benzodioxaborin, E28.

$^1$H NMR w: 1.43–2.24 (m, 6H), 2.43–2.95 (m, 8H), 4.61–4.85 (m, 1H), 5.12–5.27 (m, 1H), 7.04–7.55 (m, 14H), 7.97 (d, 1H, J=7.45).

Step (B)

Preparation of 5-hydroxy-2-(2-phenylethyl)-6-(4-phenylbutyl)-2,3-dihydrobenzofuran, E29

A mixture of aluminum chloride (2.4 gm; 18 mmoles) in toluene (30 mL) at 0° C. and under nitrogen atmosphere was added t-butylamine borane (3.8 gm; 36 mmoles). The mixture was stirred for 15 minutes after which a solution was obtained. A solution of 7,8-dihydro-2-(2-phenyl-7-(2-(2-phenylethyl)-4-(3-phenyl-propyl)-4H-furo[2,3-g]-1,3,2-benzodioxaborin, E28, (3.3 gm, crude) in toluene (15 mL) was added in several portions and the resulting mixture was stirred in the cold for 3 hours and at room temperature for 3 hours. The mixture was added slowed to ice-cold stirring 1N hydrochloric acid and the mixture stirred until fizzing stopped. The organic layer was separated, dried (MgSO$_4$), filtered and concentrated in vacuo. The residue was chromatographed on silica gel using 80:15:5 hexane:ethylacetate:triethylamine to obtain 995 mgs of 5-hydroxy-2-(2-phenylethyl)-6-(4-phenylbutyl)-2,3-dihydrobenzofuran, E29, m.p. 50°–53° C.

$^1$H NMR w: 1.52–1.79 (m, 4H), 1.85–2.21 (m, 2H), 2.46–2.94 (m, 7H), 3.21 (dd, 1H, J=15 Hz, J'=7.4 Hz) 4.25 (s, 1H), 4.64–4.80 (m, 1H), 6.56 (s, 1H), 6.61 (s, 1H), 7.06–7.37 (m, 10H).

Anal. Calcd. for $C_{26}H_{28}O_2$: C, 83.83; H, 7.57. Found: C, 84.10; H, 7.68.

EXAMPLE 11

Three Step Preparation of
5-hydroxy-2-(2-phenylethyl)-6-[3-[1(1H-tetrazol-5-yl)naphthyl)-2-yloxy]propyl]-2,3-dihydrobenzofuran, E32

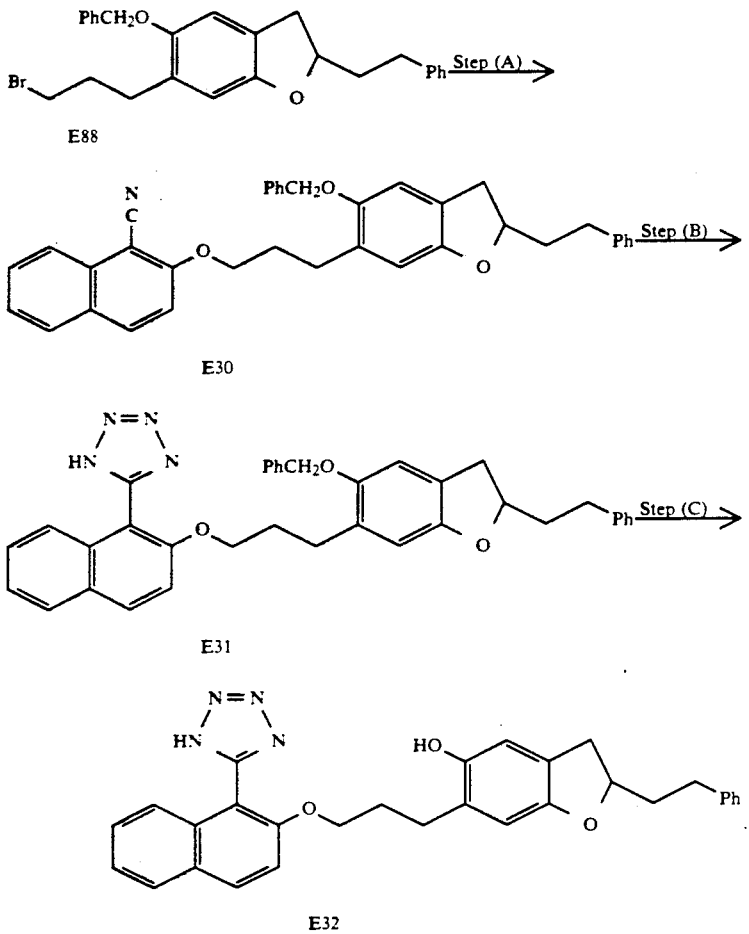

Step (A)

To 1-cyano-2-hydroxynaphthalene (1.5 g; 8.9 mmoles) in N,N-dimethylformamide (10 mL) at room temperature was added sodium hydride (210 mg; 8.8 mmoles) and the mixture was stirred for 30 minutes. Then a solution of E88 (1 g; 2.2 mmoles) in N,N-dimethylformamide (5 mL) was added and the reaction was stirred for 24 hours at room temperature. More sodium hydride (80 mg; 3.3 mmoles) was added and the reaction mixture was heated at 50° C. for 4 hours. After cooling to room temperature, the mixture was extracted with diethylether (2×50 mL). The organic layer was washed with 2N sodium hydroxide (2×15 mL), brine (3×20 mL) then dried over anhydrous magnesium sulfate, filtered and the solvent was evaporated to dryness. The oily residue was triturated with ether giving a solid which after filtration gave 600 mg (1.11 mmoles, 50%) of 5-benzyloxy-6-[3-(1-cyanonaphthyl-2-yloxy)propyl]-2-(2-phenylethyl)-2,3-dihydrobenzofuran, E30.

$^1$H NMR w: (CDCl$_3$, 250 MHz), 1.67–2.26 (m, 4H, 2CH$_2$), 2.95–3.28 (m, 6H, 3CH$_2$), 4.22 (t, 2H, J=6 Hz, CH$_2$), 4.74 (m, 1H, CH), 5.06 (s, 2H, CH$_2$) 6.67 (s, 1H, CH, Ar) 6.78 (s, 1H, CH, A) 7.13–8.12 (m, 16H, Ar)

Step B

A mixture of E30 (600 mg; 1.1 mmoles) and tri-n-butyltin azide (0.95 mL; 3.3 mmole) was heated at 120° C. for 2 hours. After cooling to room temperature, the mixture was dissolved in tetrahydrofuran, applied to a Bio-Sil silicic acid column, and eluted with a 35:65 mixture of ethyl acetate:hexane. The reaction yielded 470 mg (0.8 mmoles; 73%) of 5-benzyloxy-2-(2-phenylethyl)-6-{3-[1-(1-H-tetrazol-5-yl)naphth-2-yloxy]-propyl}-2,3-dihydrobenzofuran, E31.

$^1$H NMR w: (CDCl$_3$, DMSO-d$_6$, 250 MHz), 1.87–2.19 (m, 4H), 2.54–3.28 (m, 6H), 4.14 (t, br, 2H), 4.73 (m, 1H), 4.99 (s, 2H) 6.58 (s, 1H), 6.76 (s, 1H), 7.16–7.53 (m, 14H), 7.82 (d, 1H, J=8 Hz), 7.94 (d, 1H, 9 Hz), 8.24 (s, br, 1H).

Step C

A solution of E31 (470 mg; 0.8 mmoles) in acetic acid (12 mL) and 6N hydrochloric acid (1 mL) was heated at 125° C. for 18 hours. After cooling to room temperature, the solvent was evaporated under vaccum, pentane (2×15 mL) was added, and this solvent was also evaporated under vacuum. The compound was chromatographed on Bio-Sil silicic acid using 25:75 ethyl acetate:hexane as eluant. The reaction yielded 100 mg (0.2 mmole, 25%) of 5-hydroxy-2-(2-phenylethyl)-6-{3-[1-(1-H-tetrazol-5-yl)naphth-2-yloxyl]propyl}-2,3-dihydrobenzofuran, E32, m.p. 121°–123° C.

¹H NMR w: (CDCl₃, 250 MHz), 1.90–2.26 (m, 4H), 2.70–3.28 (m, 6H), 4.315 (t, 2H, 7H₂), 4.75 (m, 1H), 6.62 (s, 1H) 6.72 (s, 1H), 7.19–8.03 (m, 11H), 9.34 d, J=8 Hz).

EXAMPLE 12

Three Step Synthesis of 5-hydroxy-2-(2-phenylethyl)-4-[3-[(1-H-tetrazol-5-yl)phen-4-oxy]propyl]-2,3-dihydrobenzofuran, E35

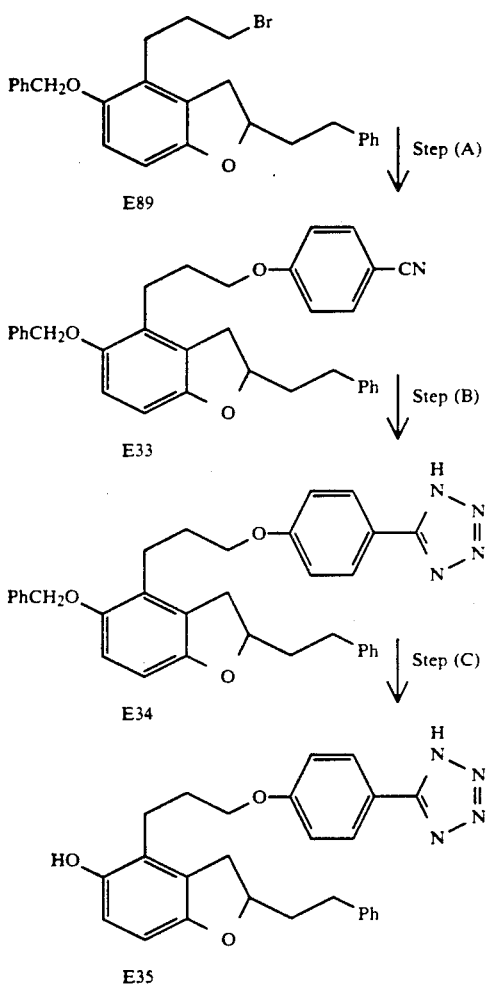

Step A

To a solution of cyanophenol (5.29 mg, 4.4 mmoles) in N,N-dimethylformamide (5 mL) at room temperature was added sodium hydridic (106 mg, 4.4 mmoles). After stirring for 30 minutes a solution of 4-(3-bromopropyl)-5-benzyloxy-2-(2-phenylethyl)-2,3-dihydrobenzofuran, E89, (500 mg, 1.1 mmoles) in N,N-formamide (2 mL) was added to the reaction mixture and this was stirred for 18 hours at room temperature. Ether was added and the solution was washed with 2N sodium hydroxide (2×), brine (3×) then dried over anhydrous magnesium sulfate and filtered. The filtrate was concentrated in vacuo and purified by column chromatography using 5:95 ethylacetate:hexane as elutant, affording 410 mg (0.8 mmoles, 76%) of 5-benzyloxy-4-[3-(1-cyanophen-4-oxypropyl]-2-(2-phenylethyl)-2,3-dihydrobenzofuran, E33.

¹H NMR δ: (CDCl₃, 250 MHz), 1.79–2.15 (m, 4H), 2.67–3.24 (m, 6H), 3.95 (t, 2H, J=8 Hz) 4.72 (m, 1H), 5.00 (s, 2H), 6.59 (d, 1H, J=8 Hz), 6.71 (d, 1H, J=8 Hz), 6.82 (s, 1H), 6.84 (s, 1H) 7.17–7.52 (m, 12H).

Step B

A mixture of E33 (400 mg, 0.8 mmoles) and tri-n-butyltinazide (0.7 mL, 2.4 mmoles) were heated at 120° C. for 2 hours. After cooling to room temperature, the mixture was chromatographed on Bio-Sil silicic acid using 35:65 ethyl acetate:hexane as elutant. The resulting oil was triturated in ether to give 315 mg (0.6 mmoles, 75%) of 5-benzyloxy-2-(2-phenylethyl)-4-{3-[1-(1-H-tetrazol-5-yl)phen-4-oxy]-propyl}-2,3-dihydrobenzofuran, E34, as a solid.

¹H NMR δ: (CDCl₃, 250 MHz) 1.75–2.16 (m, 4H), 2.61–3.27 (m, 6H), 3.97 (m, 2H), 4.71 (m, 1H), 5.00 (s, 2H), 6.58 (d, 1H, J=9 Hz), 6.70 (d, 1H, J=9 Hz), 6.93 (s, 1H), 6.96 (s, 1H), 7.14–7.44 (m, 10He, 7.93 (s, 1H), 7.96 (s, 1H).

Step C

To a solution of E34 (3.15 mg, 0.6 mmoles) in acetic acid (12 mL) and 6N hydrochloric acid (1 mL) was heated at 120° C. for 36 hours. After cooling to room temperature, the solvent was evaporated in vacuo and pentane (5×15 mL) was added and evaporated in vacuo. The residue was purified by column chromatography on Bio-Sil silicic acid using 30:70 ethyl acetate:hexane affording 200 mg (0.4 mmoles, 67%) of 5-hydroxy-2-(2-phenylethyl)-4-{3-[(1-H-tetrazol-5-yl)phen-4-oxy]propyl}-2,3-dihydrobenzofuran, E35, m.p. 193°–196° C.

¹H NMR δ: (CDCl₃, 250 MHz) 1.79–2.18 (m, 2H), 2.60–3.24 (m, 6H), 4.03 (t, 2H, J=7 Hz) 4.68 (m, 1H), 6.48 (d, 1H, J=8 Hz), 6.52 (d, J=8 Hz), 6.98 (s, 1H), 7.02 (s, 1H), 7.14–7.28 (m, 5H), 8.00 (s, 1H), 8.04 (s, 1H).

EXAMPLE 13

Two Step Preparation of 5-hydroxy-2-(2-phenylethyl)-6-(3-phenoxypropyl)-2,3-dihydrofuran

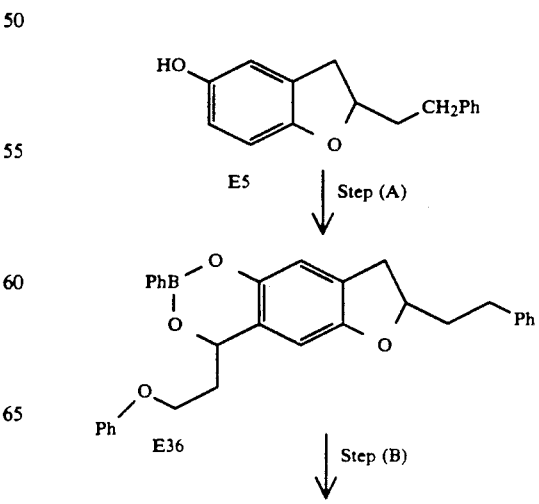

-continued

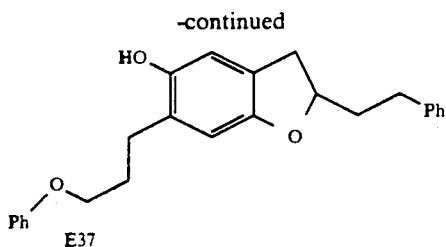

Step A

A mixture of E5 (18.4 g, 76 mmoles), 3-phenoxypropionaldehyde (23 g, 153 mmoles), phenylboronic acid (14.8 g, 121.4 mmoles) and propionic acid (1.8 g) was refluxed in toluene (460 mL), with azeotropic removal of water (Dean-Stark apparatus), for 4 hours. After cooling to room temperature, a saturated solution of sodium bicarbonate was added and the mixture was stirred for 15 minutes. The mixture was extracted with ether, washed with brine (2×), dried over magnesium sulfate and filtered. The filtrate was concentrated in vacuo. A white solid crystallized after trituration of the oily residue with ether/hexane. After filtration and air drying, 34 g (71.4 mmoles, 94%) of 7-(2-phenylethyl)-4-(2-phenoxyethyl)-2-phenyl-7,8-dihydrobenzofuran[6,5-e]-1,3,2-dioxaborin, E36, were obtained. This compound was not characterized, but used as such in the next step.

Step B

To a suspension of aluminum trichloride (26.86 g, 202 mmoles) in dry methylene chloride (640 mL), at 0° C., was added t-butylamine borane (35.07 g, 403 mmoles) portionwise. After 10 minutes a clear solution was obtained then E36 (32 g, 67.2 mmoles) was added as a solid. The solution was stirred at 0° C. for 2 hours, then slowly poured over ice (1900 mL) and concentrated hydrochloric acid (128 mL) with vigorous stirring.

The mixture was stirred until the bubbling stopped. The layers were separated, the aqueous layer was extracted with methylene chloride, the organic layers were combined and washed with brine (2×), dried over magnesium sulfate, filtered, and the filtrate was concentrated in vacuo. The residue was chromatographed using 15:85 ethylacetate:hexane as a solvent give 14 g (37.4 mmoles 56%) of 5-hydroxy-2-(2-phenylethyl)-6-(3-phenyloxypropyl)-2,3-dihydrobenzofuran, E37, identical to the material obtained in Example 14.

EXAMPLE 14

Two Step Preparation of 5-hydroxy-2-(2-phenylethyl)-6-(3-phenoxypropyl)-2,3-dihydrofuran E37

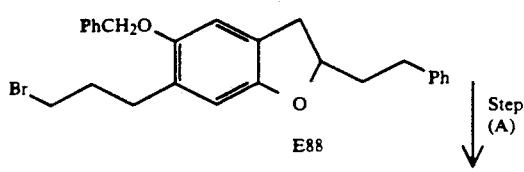

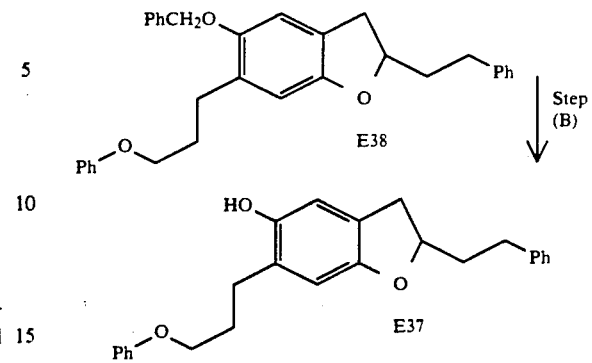

Step A

Dry phenol (14 gm, 152 mmoles) was added to 50% sodium hydride dispersion (7 gm; 145 mmoles) in dimethylformamide (200 mL) under nitrogen atmosphere. After stirring for 30 minutes, a solution of 6-(3-bromopropyl)-5-benzyloxy-2-(2-phenylethyl)-2,3-dihydrobenzofuran, E88, (8.7 gm; 16.9 mmoles) in dimethylformamide (25 mL). The mixture was stirred at room temperature for 3 hours, poured into excess 1N hydrochloric acid and extracted with diethylether. The ether layer was washed with 1N sodium hydroxide twice, dried (MgSO$_4$), filtered and concentrated in vacuo. The residue was chromatographed on silica gel using 5% ethyl acetate in hexane to yield 6.3 g (82%) of 5-benzyloxy-2-(2-phenylethyl)-6-(3-phenoxypropyl)-2,3-dihydrobenzofuran, E38, as an oil.

$^1$H NMR δ: 1.86–2.25 (m, 4H), 1.15–2.95 (m, 5H), 3.24 (dd, 1H, J=16 Hz, J'=8.5 Hz), 3.96 (t, 3H, J=6.5 Hz), 4.6–4.83 (m, 1H), 4.99 (s, 2H), 6.65 (s, 1H), 6.77 (s, 1H), 6.80–7.0 (m, 2H), 7.1–7.5 (m, 13H).

Step B 1 molar boron tribromide solution in dichloromethane (18.8 mL; 18.8 mmoles) was added dropwise to a solution of E38 in dichloromethane (300 mL) at −78° C. The mixture was stirred for 10 minutes and methanol (5 mL) was then added dropwise. The mixture was brought to room temperature and saturated sodium bicarbonate solution added. The organic layer was separated, dried (MgSO$_4$), filtered and concentrated in vacuo. The residue was chromatographed on silica gel using 15% ethyl acetate in hexane to yield 4.5 gm (76%) of 5-hydroxy-2-(2-phenylethyl)-6-(3-phenoxypropyl)-2,3-dihydrobenzofuran, E37, m.p. 65°–70° C.

Anal Calcd. for C$_{25}$H$_{26}$O$_3$: C, 80.18; H, 6.99. Found: C, 80.51; H, 7.15.

$^1$H NMR δ: 1.86–2.24 (m, 4H), 2.68–2.95 (m, 5H), 3.2 (dd, 1H, J=15 Hz, J'=7.4), 4.0 (t, 2H, J=5.5) 4.67–4.83 (m, 1H), 5.21 (s, 1H), 6.58 (s, 1H), 6.67 (s, 1H), 6.88–7.04 (m, 3H), 7.13–7.39 (m, 7H).

EXAMPLE 15

Two Step Preparation of 5-hydroxy-2-(2-phenylethyl)-6-(3-phenoxypropyl)-2,3-dihydrofuran E37

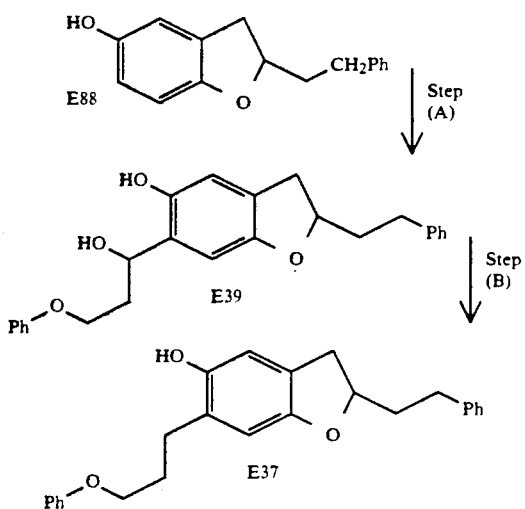

Step A

To a solution of E5 (100 gm, 0.4 mmoles) in dry dichloromethane (1.6 L) at 0° C. under $N_2$ was added a 3.0M solution of ethyl magnesium bromide in ether (147 mL, 0.44 moles) slowly with stirring. After 20 minutes, 3-phenoxypropanaldehyde (90 g, 0.6 mole) was added as a solution in dichloromethane (90 mL). The reaction mixture was stirred at 0° C. for 6 hours then triethylamine was added (9 mL) and the reaction concentrated to approximately 30% of the original volume at reduced pressure. The residue was diluted with ether (4.5 L) and the organic phase was washed sequentially with equal volumes of saturated aqueous ammonium chloride containing hydrochloric acid (35 mL) and saturated aqueous sodium chloride containing 10% w/v potassium carbonate. The residue was subsequently dried over anhydrous magnesium sulfate. Filtration and removal of the solvent at reduced pressure gave a solid which was purified by first slurrying with ether (500 mL) at 0° C. for 16 hours, then diluting with an equal volume of hexane. After stirring for 1 hour at 0° C. the product E39 was isolated by filtration (113 gm). The mother liquors were chromatographed (silica, 20% ethyl acetate in hexane) to yield a further product (8 gms).

Step B

To a solution of the product E39 from above (121 gm, 0.31 mole) in dry THF (1.2 L) at −78° C. under $N_2$ was added sequentially methane sulfonyl chloride (57.6 mL, 0.74 mole) in one portion and triethylamine (103.8 mL, 0.79 mole) dropwise. After stirring at −78° C. for 15 minutes the reaction mixture was allowed to warm to room termperature, then quenched by the addition of saturated aqueous sodium chloride (1.2 L). The organic phase was separated and then washed with equal volumes saturated aqueous sodium chloride containing 1% HCl then saturated aqueous sodium chloride containing 5% potassium carbonate. The aqueous washed were extracted with 500 mL of THF and the organic phase from this was added to the original organic phase before the subsequent wash. The combined organic phases were dried for 1 hour over anhydrous magnesium sulfate with stirring. The magnesium sulfate was then removed by filtration and the volume of the filtrate was reduced to approximately 600 mL. The concentrated filtrate was added cautiously to a stirred suspension of lithium tetrahydridoaluminate (30 gm) in dry THF (2 L) at 0° C. under nitrogen. The resulting mixture was then allowed to warm to room temperature and maintained at room temperature for 16 hours. The reaction mixture was cooled to 0° C. and diluted with, sequentially, ether (1.5 L), water (30 ml), aqueous 15% sodium hydroxide (30 mL), and water (90 mL) dropwise. The resulting mixture was stirred at 0° C. for 2 hours and the pH was adjusted to approximately 7 (moist test strip) with acetic acid. Filtration and removal of the solvent at reduced pressure gave a oily residue which was dissolved in ether 2 L, and washed with aqueous 10% potassium carbonate (2×1 L). Drying of the organic phase over anhydrous magnesium sulfate and removal of the solvent at reduced pressure gave 5-hydroxy-2-(2-phenylethyl)-6-(3-phenoxypropyl)-2,3-dihydrobenzofuran, E37, as an off white solid. Purification of this material as described for the other methods for its preparation gave product which was indistinguishable from that prepared in Examples 13 and 14.

EXAMPLE 16

Two Step Preparation of 5-carboxymethoxy-2-(2-phenylethyl)-6-(3-phenoxypropyl)-2,3-dihydrofuran E41

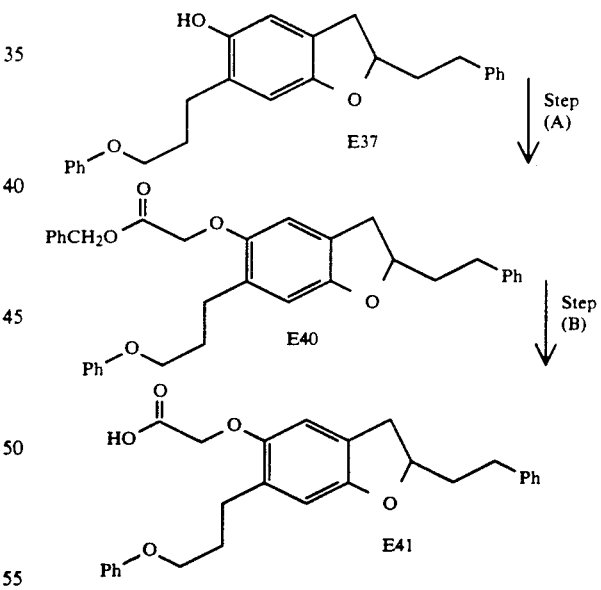

Step A

To a solution of E37 (500 mg, 1.34 mmoles) in butan-2-one (10 mL) and potassium carbonate (370 mg; 2.68 mmole) was added benzyl bromoacetate (0.468 mL; 2.68 mmoles) and the mixture was refluxed for 18 hours. After cooling to room temperature, the reaction mixture was filtered on celite and the filtrate purified by column chromatography using 10:90 ethyl acetate: hexane as elutant giving 667 mg (1.28 mmoles, 96%) of 5-carbobenzyloxymethoxy-2-(2-phenylethyl)-6-(3-phenoxypropyl)-2,3-dihydrobenzofuran, E40.

$^1$H NMR δ: (CDCl$_3$, 250 MHz) 1.88–2.21 (m, 4H), 2.70–3.24 (m, 6H), 3.96 (t, 2H, J=8 Hz), 4.59 (s, 2H), 4.74 (m, 1H), 5.23 (s, 2H), 6.58 (s, 1H), 6.64 (s, 1H), 6.88–7.37 (m, 15H).

Step B

To a solution of E40 (200 mg, 0.38 mmoles) in ethanol (5 mL) was added 10% palladium on charcoal (50 mg) and the mixture was hydrogenated for 2 hours on the Parr apparatus at 50 p.s.i. The mixture was filtered on celite and the filtrate was concentrated in vacuo. The residue was triturated with diethylether to obtain a solid which was filtered and air dried. The solid comprised of 140 mg (0.32 mmoles, 84%) of 5-carboxymethoxy-2-(2-phenylethyl)-6-(3-phenoxypropyl)-2,3-dihydrobenzofuran, E41, m.p. 120°–121° C.

$^1$H NMR δ: (CDCl$_3$, 250 MHz) 1.89–2.23 (m, 4H), 2.71–3.30 (m, 6H), 4.02 (t, 2H, J=7 Hz) 4.58 (s, 2H), 4.76 (m, 1H), 6.64 (s, 1H), 6.66 (s, 1H), 6.91–6.98 (m, 3H), 7.18–7.33 (m, 8H).

EXAMPLE 17

Two Step Synthesis to 2-[4-[3-[2,3-dihydro-5-hydroxy-2-(2-phenylethyl)benzofuran-6-yl]propoxy]phenyl]-2-methylpropionic acid

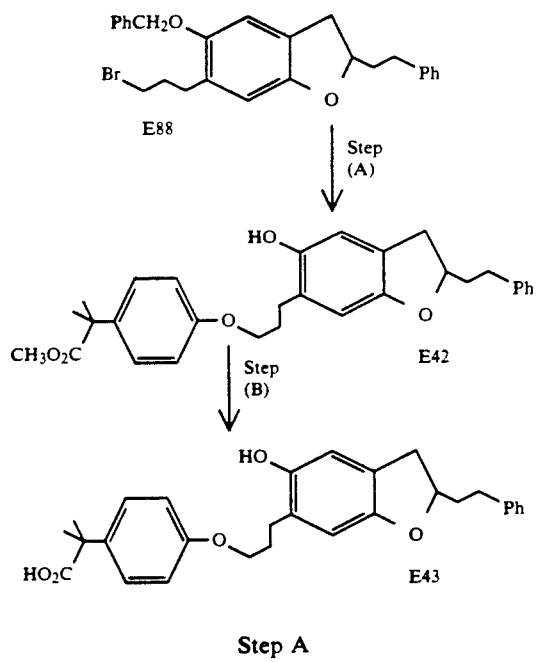

Step A

To a stirring solution of methyl 2-(4-hydroxyphenyl)-2-methylpropionate (0.81 g; 4.19 mmol) in dry diemthylformamide (8 mL) was added sodium hydride (192 mg, 4 mmol) as a 50% dispersion in oil. The mixture was stirred at room temperature for 30 minutes. A solution of 6-(3-bromopropyl)-5-benzyloxy-2-(2-phenylethyl)-2,3-dihydrobenzofuran, E88, in dry dimethylformamide (2 mL) was added. The resulting mixture was stirred at room temperature for 20 hours. The mixture was poured into cold dilute HCl (1N, 25 mL) and extracted twice with ethylacetate (50 mL). The combined organic extracts were washed with 1N HCl (25 ml×2) and brine (25 mL), dried (Na$_2$SO$_4$) and concentrated in vacuo. The residue was chromatographed on silica gel to give 500 mg (87% yield) methyl-2-[4-[3-[2,3-dihydro-5-benzyloxy-2-(2-phenylethyl)benzofuran-6-yl]propoxy]phenyl]-2-methylpropanoate, E42.

$^1$H NMR δ: 1.85–2.2 (m, 2H), 2.65–2.94 (m, 3H), 3.21 (d, d, 1H, J=15 Hz, J'=9 Hz), 3.64 (s, 2H), 3.92 (t, 2H), 4.73 (m, 1H), 4.98 (s, 2H), 6.63 (s, 1H) 6.76 (s, 1H), 6.80 (d, 2H, J=7.5 Hz), 7.13–7.48 (m, 12H)

Step B

The methyl ester E42 (500 mg) was hydrolysed by treating it with ethanol (5 ml) and sodium hydroxide (5N, 2 ml) for 2½ hours at room temperature. The resulting mixture was neutralized with cold dilute (1N) HCl and extracted with ethyl acetate (50 ml). The organic extracts were dried (Na$_2$SO$_4$) and concentrated in vacuo to give 442 mg of the corresponding acid which was hydrogenated without further characterization. A mixture of the acid (400 mg) and palladium on charcoal (40 mg, 10%) in ethanol (40 ml) was hydrogenated at 50 p.s.i. for 1½ hours. The mixture was filtered through celite. The filtrate was concentrated in vacuo and chromatographed on Bio-Sil (eluted with 20% ethyl acetate in hexane) to give 300 mg (92%) yield of 2-[4-[3-[2,3-dihydro-5-hydroxy-2-(2-phenylethyl) benzofuran-6-yl]propoxy]phenyl]-2-methylpropionic acid, E43, m.p. 134°–136° C.

$^1$H NMR δ: 1.83–2.22 (m, 2H), 2.75–2.92 (m, 3H), 3.2 (dd, 1H, J=16.7 Hz, J'=7.5 Hz), 3.97 (t, 2H, J=5.5 Hz), 4.75 (m, 1H), 6.58 (s, 1H), 6.66 (s, 1H) 6.90 (d, 2H, J=8.3 Hz), 7.15–7.39 (m, 7H).

Anal Calcd. for C$_{29}$H$_{32}$O$_5$: C, 76.63; H, 7.00. Found: C, 75.30; H, 7.14.

EXAMPLE 18

One Step Production to 2-[3-(2,3-dihydro-5-hydroxy-2-(2-phenylethyl)benzofuran-6-yl]propanthio)benzothiazole E44

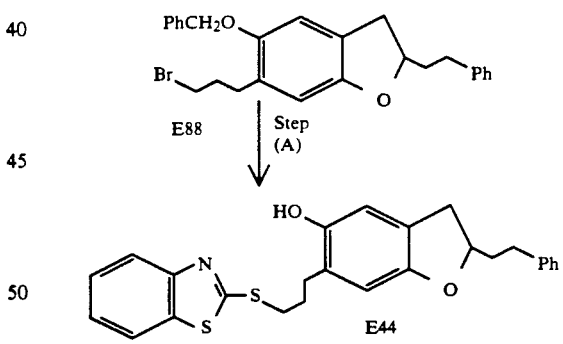

Step A

Following the same procedure described above for producing compound E26 from E88 and using 2-thiolbenzothiazole (658 mg, 1.46 mmole), 2-(3-[2,3-dihydro-5-benzyloxy-2-(2-phenylthyl)benzofuran-6-yl]propanthiol)benzothiazole, E44, was isolated in 91% yield (712 mg). Without further characterization, the benzyl protecting group was cleaved by treating the latter (507 mg, 1.05 mmol) with HCl (6N, 1.4 ml) and acetic acid (11 ml). The mixture was refluxed for 18 hours. The mixture was concentrated in vacuo. The residue was chromatographed on silica gel (eluted with 20% ethyl acetate in hexane) to give 223 mg (50%) of the title compound mp 134°–136° C.

¹H NMR δ: 1.83-2.03 (m, 1H), 2.03-2.25 (m, 3H), 2.67-2.95 (m, 5H), 3.20 (dd, 1H, J=15 Hz, J'=9 Hz), 3.35 (t, 2H, J=6.3 Hz), 4.62-4.82 (m, 1H), 5.24 (s, 1H), 6.61 (s, 1H), 6.67 (s, 1H), 7.12-7.50 (m, 7H), 7.75 (d, 1H, J=7 Hz), 7.94 (d, 1H, J=7 Hz).

Anal Calcd. for $C_{26}H_{25}NO_2S_2$: C, 69.79; H, 5.63; N, 3.13; S, 14.30. Found: C, 69.83; H, 5.94; N, 2.95; S, 14.36.

EXAMPLE 19

Three Step Preparation of p-[3-[2,3-dihydro-5-hydroxy-2-(2-phenylethyl)benzofuran-6-yl]propoxy]phenylhydroxamic acid E47

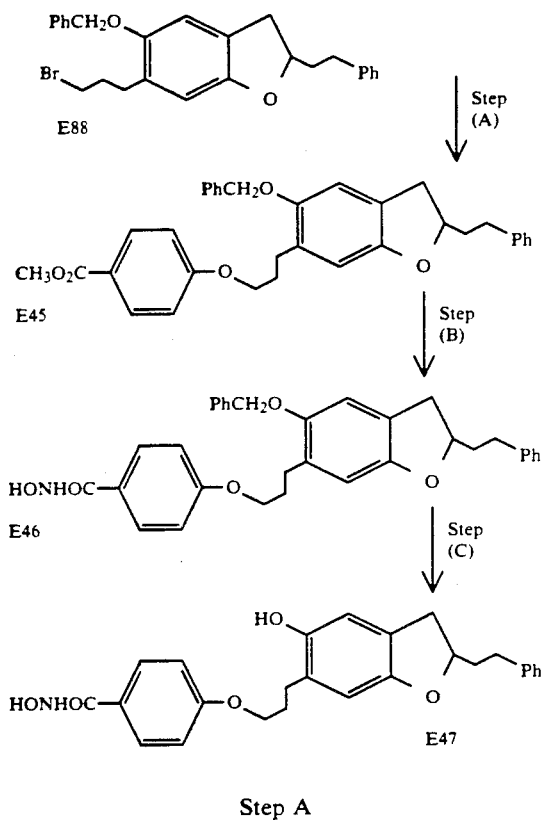

Step A

To a stirred solution of E88 (650 mg, 1.44 mmol) and methyl-4-hydroxybenzoate (610 mg, 4.0 mmols) in dry dimethylformamide (5 mL) at 0° C. under an atmosphere of dry nitrogen was added dry sodium hydride (98%, 88 mg, 3.67 mmoles) in one portion. The resulting mixture was stirred for 10 minutes at 0° C. then allowed to warm to room temperature. The reaction mixture was allowed to stand at room temperature for 16 hours then diluted with Et₂O 25 mL. The organic phase was washed sequentially with equal volumes of H₂O in 1N NaOH (aqueous) and saturated aqueous sodium chloride then dried over anhydrous magnesium sulfate. Filtration and removal of the solvent at reduced pressure gave the coupling product p-[3-[2,3-dihydro-5-benzyloxy-2-(2-phenylethyl)benzofuran-6-yl]propoxy]benzoic acid, E45, as an oil which was used without further purification.

Step B

To a solution of hydroxylamine hydrochloride (140 mg, 2 mmol) in absolute ethanol (2 mL) was added a 2M solution of sodium ethoxide in ethanol (2 mL). The resulting mixture was stirred at room temperature for 30 minutes then a solution of the coupling product E45 from above in tetrahydrofuran (dry, 4 mL) was added. The resulting mixture was stirred at room temperature for 16 hours then diluted with dichloromethane (50 mL). The organic phase was washed sequentially with equal volumes of saturated aqueous sodium chloride, aqueous 20% citric acid solution (2×) and dryed over anhydrous magnesium sulfate. Filtration and removal of the solvent at reduced pressure gave a residue which was purified by swishing with ether at 0° C. (2×20 mL) to remove any remaining starting material to give p-[3-[2,3-dihydro-5-benzyloxy-2-(2-phenylethyl)benzofuran-6-yl]propoxy]phenyl hydroxamic acid, E46 (245 mg).

¹H NMR (250 MHz,CDCl₃)δ: 1.9-2.2 (4H, m, —O—CH—C$\underline{H}_2$—CH₂—Ph, Ar—CH₂—C$\underline{H}_2$—CH₂—O—); 2.6-2.95 (5H, m, —CH₂—C$\underline{H}_2$—Ph, Ar—C$\underline{H}_2$—CH₂—, Ar—CH$_A$H$_B$—CH—O); 3.24 (1H, dd, J=8.25 Hz, J'=14.6 Hz, Ar—CH$_A$$\underline{H}_B$—CH—O); 4.00 (2H, t, J=6.6 Hz, CH₂C$\underline{H}_2$—O—); 4.76 (1H, m, Ar—CH₂C$\underline{H}$—O); 5.00 (2H, s, Ph—CH₂—O—); 6.64 (s, 1H, Ar $\underline{H}$(H-7)); 6.78 (s, 1H, ArH(H-4)); 6.88 (d, 2H, J=7.5 Hz, —Ar—C(O) NHOH-meta H's); 7.1-7.5 (10H, m, 2Ph); 7.67 (2H, d, J=7.5 Hz, —Ar—C(O)NHOH-ortho H's). *

Step C

To a solution of E46 from above (200 mg, 0.46 mmol) in ethanol (20 mL) under nitrogen was added 10% palladium on carbon (25 mg). The resulting suspension was shaken under an atmosphere of hydrogen (50 psi) for 4 hours then filtered through washed celite and the solvent was removed at reduced pressure. Chromatography of the residue on 100-200 mesh Biosil-A (30-5-0-75%) ethyl acetate in hexane) gave the title compound for this example, E47, (101 mg), m.p. 146°-148° C.

¹H NMR (250 MHz, CDCl₃+CD₃CO₂D)δ: 1.8-2.2 (4H, m, —O—CH—C$\underline{H}_2$, Ar—CH₂—C$\underline{H}_2$—); 2.6-3.0 (5H, m, —CH₂—C$\underline{H}_2$—Ph, Ar—CH₂—C$\underline{H}_2$—, Ar—CH$_A$H$_B$—CH—O); 3.21 (1H, dd, J=8.3 Hz, J'=14.5 Hz, Ar—CH$_A$$\underline{H}_B$—CH—O); 4.03 (2H, bt, J= 6.3 Hz, CH₂C$\underline{H}_2$—O—); 4.75 (1H, m, Ar—CH₂C$\underline{H}$—O); 6.65 (1H, s, ArH(H-7)); 6.78 (1H, s, ArH (H-4)); 6.86 (2H, bd, J=7.5 Hz); 7.1-7.35 (5H, m, Ph—H's); 7.72 (2H, bd, J=7.5 Hz). *

EXAMPLE 20

Three Step Synthesis of 5-hydroxy-3-methyl-2-(p-methoxybenzyl)-2,3-dihydrobenzofuran E50

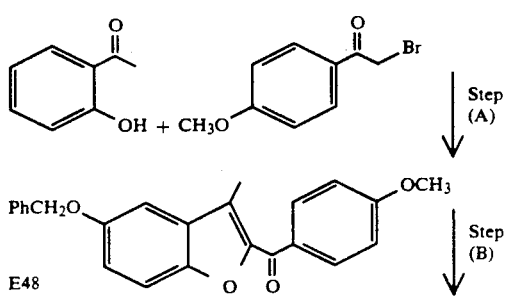

-continued

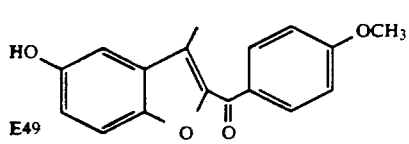

↓ Step (C)

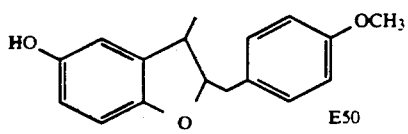

Step A

A mixture of 2-hydroxy-5-benzyloxyacetophenone (93 g, 380 mmoles), p-methoxyphenacyl bromide (88 g, 384 mmoles) and potassium carbonate (106 g, 768 mmoles) in acetone (1.5 L) was refluxed for 46 hours. The reaction mixture was cooled and filtered. The filtrate was evaporated in vacuo. The residue was chromatographed on silica gel using 10% ethylacetate in hexane as eluent to yield (127 g, 89%) of 2-(p-methoxybenzyl)-3-methyl-5-benzyloxybenzofuran, E48.

$^1$H NMR δ: 2.55 (s, 3H, CH$_3$), 3.85 (s, 3H, CH$_3$O), 5.1 (s, 2H, benzylic proton), 7.00 (d, J=9 Hz, 2H, proton ortho to methoxy), 7.15 (m, 2H, aromatic proton), 7.45 (m, 6H, benzylic proton +1 proton), 8.15 (d, J=9 Hz, 2H, proton ortho to benzoyl).

Step B

A solution of E48 (5 g, 13.44 mmoles) in ethanol (100 ml) was hydrogenated in a Parr apparatus in presence of 5% palladium on carbon for a period of 1 hour. The catalyst was removed by filtration and the filtrate was concentrated to dryness. The product the 2-(p-methoxybenzoyl)-3-methyl-5-hydroxybenzofuran, E49, was used as such in the next step.

Step C

To a solution of E49 (3.8 g, 13.44 mmoles) in trifluoro acetic acid (30 ml) was added triethyl silane (15 ml, 94 mmoles). The reaction mixture was stirred at room temperature for a period of 18 hours. The mixture was diluted with H$_2$O 50 ml and neutralized with K$_2$CO$_3$ (solid). The solution was extracted with ethyl acetate and the combined organic phases were dried Na$_2$SO$_4$ and concentrated in vacuo. The residue was chromatographed on silica gel using 10% ethylacetate in hexane as eluent to yield 3 g, 84% of 5-hydroxy-3-methyl-2-p-methoxybenzyl-2,3-dihydrobenzofuran, E50.

$^1$H NMR δ: 1.15 (d, J=6 Hz, 3H), 3.05 (m, 3H, benzylic protons), 3.78 (s, 3H, methoxy), 4.4 (q, 1H, methyne), 4.72 (m, 1H, benzylic methyne), 6.65 (s, 3H, aromatic), 6.85 (d, J=9 Hz, 2H), 7.2 (d, J=9 Hz, 2H).

EXAMPLE 21

Six Step Synthesis to 6-(3-phenoxypropyl)-5-hydroxy-2-p-methoxybenzyl-3-methyl-2,3-dihydrofuran E56

↓ Step (A)

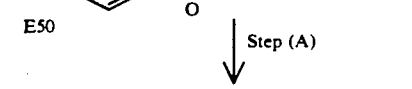

↓ Step (B)

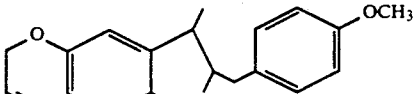

↓ Step (C)

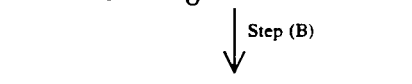

↓ Step (D)

↓ Step (E)

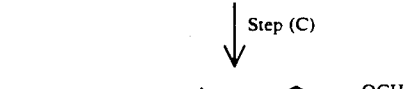

↓ Step (F)

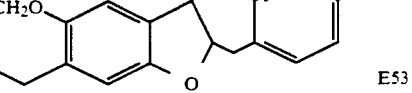

Step A

A mixture of E50 (16 g, 59.25 mmoles), allyl bromide (10 g, 82.6 mmole), K$_2$CO$_3$ (8.17 g, 59.2 mmoles) in acetone (300 ml) was refluxed for a period of 18 hours. The reaction mixture was cooled, filtered through celite and concentrated in vacuo. The residue was chromatographed on silica gel using 5% ethyl acetate in hexane as eluent to yield 22 g (100%) of 5-allyloxy-3-methyl-2-p-methoxybenzyl-2,3-dihydrobenzofuran, E51.

¹H NMR δ: 1.05 (d, J=6 Hz, 3H), 2.7-3.3 (m, 3H,), 3.7 (s, 3H), 4.4 (m, 2H), 5.1-5.3 (m, 2H olefinic proton), 6.0 (m, 1H), 6.6 (s, 3H), 6.8 (d, J=9 Hz, 2H), 7.15 (d, J=9 Hz, 2H).

Step B

A solution of 5-allyloxy-3-methyl-2-p-methoxybenzyl-2,3-dihydrobenzofuran, E51, (22 g, 59 mmoles) in dichlorobenzene (100 ml) was refluxed for a period of 18 hours. The solution was concentrated in vacuo. The residue was chromatographed on silica gel using 15% ethyl acetate in hexane as eluent to yield 18 g (82%) of 6-allyl-5-hydroxy-3-methyl-2-p-methoxybenzyl-2,3-dihydrobenzofuran, E52.

¹H NMR δ: 1.05 (d, J=6 Hz, 3H) 2.6-3.2 (m, 3H,) 3.25 (d, 2H) 3.7 (s, 3H) 4.35 (m, 1H) 4.65 (s, 1H, phenolic proton) 5.05 (m, 2H, olefinic proton) 6.0 (m, 1H) 6.5 (s, 2H), 6.8 (d, J=9 Hz, 2H) 7.15 (d, J=9 Hz, 2H).

Step C

A solution of E52 (0.5 g, 1.35 mmoles) was added potassium carbonate (0.44 g, 3.2 mmoles) and benzyl bromide (0.38 ml, 3.2 mmoles). The reaction mixture was refluxed for 6 hours. The suspension was filtered through celite and concentrated in vacuo. The residue was chromatographed on silica gel using 5% ethyl acetate in hexane to yield (0.6 g, 96%) of 5-benzyloxy-6-allyl-3-methyl-2-p-methoxybenzyl-2,3-dihydrobenzofuran, E53.

Step D

To a solution of E53 (0.5 g, 1.25 mmoles) in THF (5 ml) cooled at 0° C. was added 1M borane in THF (3.2 ml, 3.2 mmoles). The reaction mixture was stirred for 3 hours. Trimethylamine-N-oxide (1.1 g, 10 mmoles) was then added and the reaction mixture was refluxed for 3 hours. The mixture was concentrated in vacuo and the residue was chromatographed on silica gel using 20% ethyl acetate in hexane to yield 6-(3-hydroxypropyl)-5-benzyloxy-2-p-methoxybenzyl-3-methyl-2,3-dihydrobenzofuran, E54, (0.34 g, or 47%).

¹H NMR δ: 1.1 (d, J=6 Hz, 3H), 1.6-2.0 (m, 2H,), 2.65 (t, J=6 Hz, 2H), 2.8-3.3 (m, 3H), 3.5 (t, J=6 Hz, 2H), 3.7 (s, 3H, methoxy), 4.4 (q, 1H, methyne), 4.95 (s, 2H), 6.5 (d, 2H, H₄, H₇), 6.75 (d, J=9 Hz, 2H), 7.15 (d, J=9 Hz, 2H), 7.3 (s, 5H).

Step E

To E54 (0.425 g, 1 mmole) dissolved in THF (50 ml) was added diethyl azodicarboxylate (0.265 g, 1.5 mmoles) and phenol (0.1 g, 1 mmole). The solution temperature was lowered to 0° C. and a solution of triphenyl phosphine (0.4 g, 1.5 mmoles) in THF (5 ml) was added dropwise. Then the reaction mixture temperature was raised to room temperature and stirred for 3 hours. The mixture was concentrated in vacuo. The residue was chromatographed on silica gel using 20% ethyl acetate in hexane to yield 0.21 g or 42% of 6-(3-phenoxypropyl)-5-benzyloxy-2-p-methoxybenzyl-3-methyl-2,3-dihydrobenzofuran, E55.

¹H NMR δ: 1.15 (d, J=6 Hz, 3H), 2.05 (m, 2H,), 2.75 (t, J=6 Hz, 2H), 3.05 (m, 2H), 3.75 (s, 3H), 3.95 (t, J=6 Hz, 2H), 4.4 (s, 1H, methyne), 4.95 (s, 2H), 6.55 (s, 1H, H₇), 6.6 (s, 1H, H₄), 6.75-6.95 (m, 5H), 7.05-7.45 (m, 9H).

Step F

A solution of E55 (0.1 g, 0.2 mmole) in ethanol (15 ml) was hydrogenated in a Parr apparatus in the presence of 10% palladium on carbon at 35 psi for 4 hours. The catalyst was removed by filtration and filtrate was concentrated to dryness. The residue was chromatographed on silica gel using 10% ethyl acetate in hexane as eluent to yield 60 mg or 75% of 6-(3-phenoxypropyl)-5-hydroxy-2-p-methoxybenzyl-3-methyl-2,3-dihydrobenzofuran, E56.

¹H NMR δ: 1.05 (d, J=6 Hz, 3H), 1.9 (q, 2H), 2.6 (t, 2H), 2.7-3.1 (m, 3H), 3.65 (s, 3H), 3.85 (t, 2H, CH₂-O), 4.35 (q, 1H, methyne), 6.4 (s, 2H, H₄, H₇), 6.6-6.9 (m, 5H), 7.0-7.25 (m, 4H).

EXAMPLE 22

Four Step Preparation of 6-(4-(p-chlorophenyl)-butyl)-5-hydroxy-3-methyl-2-p-methoxybenzyl)-2,3-dihydrofuran E59

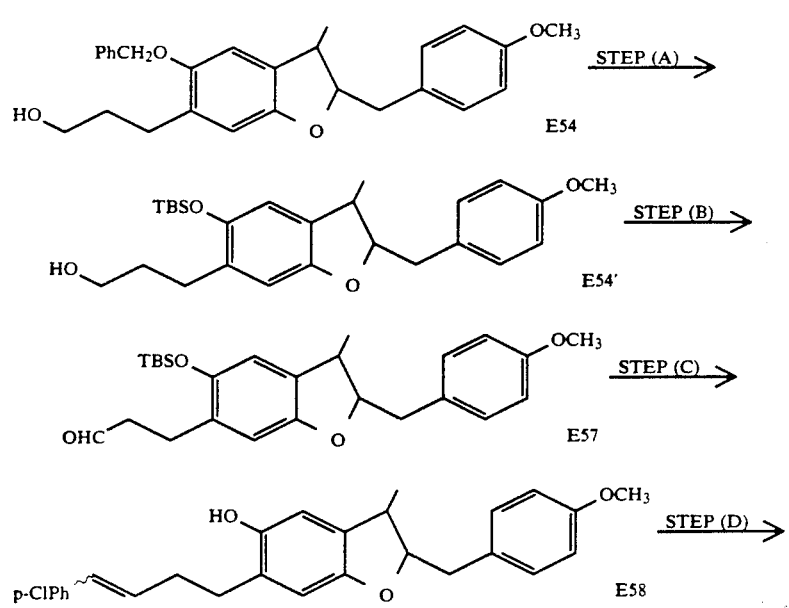

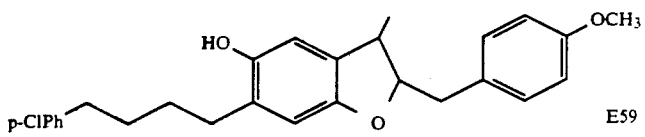

Step A

The 5-position hydroxy protecting group of E54 which is benzyl, is converted by standard methods to t-butyldimethyl silyl. Produced is 6-(3-hydroxypropyl)-5-t-butyldimethylsiloxy-3-methyl-2-p-methoxybenzyl-2,3-dihydrobenzofuran, E54'.

Step B

To a cooled solution (−60° C.) of oxalyl chloride (34 mL, 0.4 mmole) in $CH_2Cl_2$ (5 mL) was added DMSO (68 mL, 0.87 mmoles) dissolved in $CH_2Cl_2$ (1 mL) dropwise. This mixture was stirred for 10 minutes. Then E54' (161 mg, 0.36 mmole) in $CH_2Cl_2$ (4 mL) was added dropwise. After 15 minutes at −60° C., triethylamine (250 mL, 1.7 mmoles) was then added to the solution. The temperature of the mixture was raised to room temperature, water (3.0 mL) was added, the organic phases were separated and the aqueous were reextracted with $CH_2Cl_2$. The combined organic phases were dried ($Na_2SO_4$) and concentrated under vacuo. The residue was chromatographed on silica gel using 10% ethyl acetate in hexane as eluent to yield (0.15 gm, 94%) of title compound 5-t-butyldimethylsilyoxy-6-(3-oxopropyl)-3-methyl-2-p-methoxybenzyl-2,3-dihydrobenzofuran, E57.

$^1$H NMR δ: 0.15 (s, 6H), 0.95 (s, 9H), 1.15 (d, J=6 Hz, 3H), 2.4–3.3 (m, 7H), 3.75 (s, 3H), 4.35 (m, 1H, methyne), 6.48 (s, 2H, $H_4$, $H_7$), 6.8 (d, J=9 Hz, 2H), 7.15 (d, J=9 Hz, 2H), 9.8 (s, 1H, aldehyde proton).

Step C

To ethanol (5 ml) was added Na (4.6 mg, 0.2 mmoles) at room temperature. The mixture was stirred until the sodium was completely dissolved. To this cooled at 0° C. solution was added p-chlorobenzyl triphenylphosphonium chloride, (84.4 mg, 0.2 mmole) and this solution was stirred for 30 minutes. To this phosphorane solution was added E57 (50 mg, 0.11 mmoles). The reaction mixture was stirred at 0° C. for 1.30 hours. This solution was acidified with HCl 1N and concentrated in vacuo. The residue was chromatographed on silica gel using 10% ethyl acetate in hexane to yield 30 mg, 61% of 5-tert-butyldimethylsilyoxy derivative that was treated with tetrabutyl ammonium fluoride (53 mL, 0.05 mmole) and stirred for 1 hour at 0° C. The reaction mixture was then concentrated in vacuo. The residue was chromatographed on silica gel and eluted with 10% ethyle acetate in hexane to yield 6-(1-p-chlorophenyl-buten-4-yl)-5-hydroxy-3-methyl-2-p-methoxybenzyl-2,3-dihydrobenzofuran, E58.

$^1$H NMR δ: 1.15 (d, J=6 Hz, 3H), 1.28 (d, J=6 Hz, 3H), 2.3–3.3 (m, 7H), 3.8 (s, 3H), 4.1 (m, 1H), 4.35 (s, 1H, hydroxy), 6.3 (s, 1H, olefinic), 6.5 (s, 2H), 6.85 (d, 7.5 Hz, 2H), 7.28 (m, 6H, p-chlorophenyl).

Step D

A solution of E58 (30 mg, 0.07 mmole) in ethanol was hydrogenated in a Parr apparatus in the presence of 10% palladium on carbon. The catalyst was removed by filtration and the filtrate was concentrated to dryness. The residue was chromatographed on silica gel to yield 20 mg or 66% of 6-(4-(p-chlorophenyl)butyl)-5-hydroxy-3-methyl-2-p-methoxybenzyl-2,3-dihydrobenzofuran, E59.

$^1$H NMR δ: 1.18 (d, J=6 Hz, 3H), 1.55 (m, 4H), 2.5 (m, 4H), 2.8–3.2 (m, 3H), 3.75 (s, 3H), 4.3 (m, 1H, methyne), 6.45 (s, 2H, $H_4$, $H_7$), 6.85 (d, 2H), 7.15 (m, 6H, aromatic).

EXAMPLE 23

Eight Step Preparation of 2-(2-p-methoxystyryl)-3,3-dimethyl-5-benzyloxy-2,3-dihydrobenzofuran E67

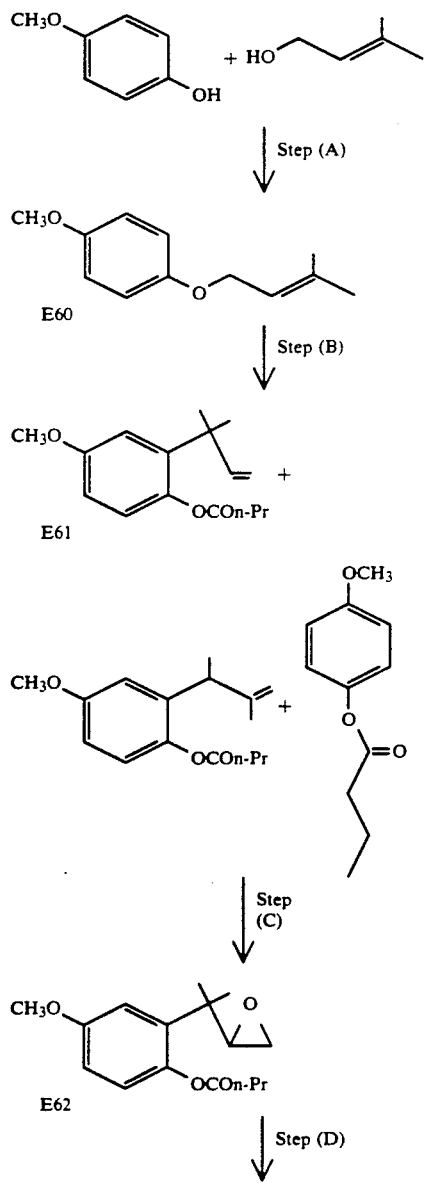

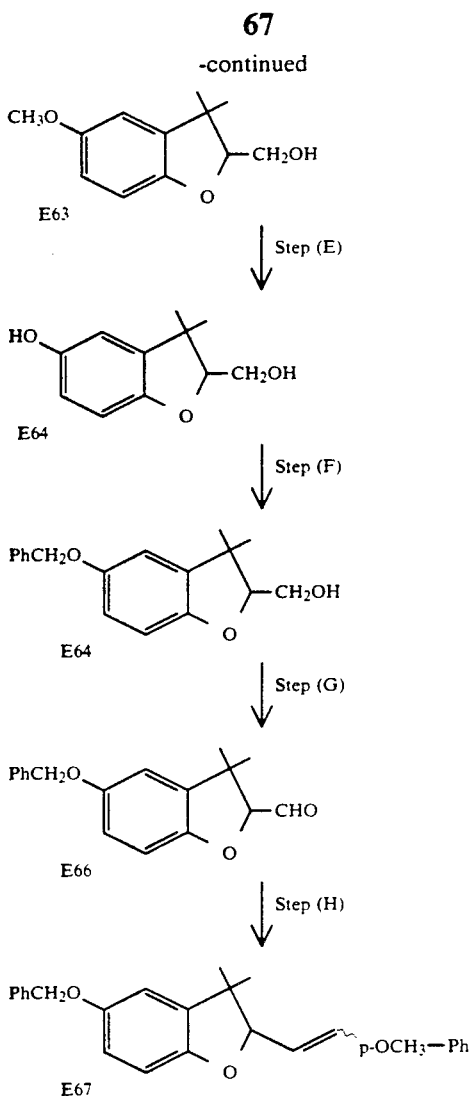

Step A

To a mixture of p-methoxyphenol (62 gm; 500 mmoles), 3-methyl-2-buten-1-ol (4.3 gm; 500 mmoles), and diethyl azodicarboxylate (108 gm; 625 mmoles) in tetrahydrofuran (2 L) at 5° C. was added a solution of triphenylphosphine (163 gm; 625 mmoles) in tetrahydrofuran (500 mL) over 30 minutes. The mixture was then stirred at room temperature for 1 hour and then concentrated in vacuo. The residue was triturated with 5% ethylacetate in hexane. The solid was filtered off and the filtrate concentrated in vacuo. The residue was chromatographed on silica gel using 5% ethylacetate in hexane as eluent to obtain 67 gm (70%) of 3-methyl-2-buten-1-yl-p-methoxyphenylether, E60, as an oil.

$^1$H NMR δ: 1.70 (s, 3H), 1.76 (s, 3H), 3.7 (s, 3H), 4.36 (d, 2H, J=6 Hz), 5.23–5.6 (m, 1H), 6.76 (s, 4H).

Step B

A mixture of E60 (42 gm; 219 mmoles) n-butyric anhydride (69 gm; 438 mmoles), and N,N-dimethylaniline (66 gm; 547 mmoles) in 1,2-dichlorobenzene (200 mL) was refluxed for 24 hours under nitrogen atmosphere. After cooling to room temperature, water (100 mL) was added and the mixture stirred for 2 hours. 3N hydrochloric acid (200 mL) was then added followed by dichloromethane (100 mL). The organic layer was separated, washed with 3N hydrochloric acid (200 mL), 1N sodium bicarboante (300 mL), dried (MgSO$_4$), filtered and concentrated in vacuo until most of the 1,2-dichlorobenzene was driven off. The residue was chromatographed on silica gel using 10% ethyl acetate in hexane to obtain 39.5 gm (68%) of a mixture containing 2-(1,1-dimethylallyl)-p-methoxyphenyl n-butyrate, E61, 2-(1,2-dimethylallyl)-p-methoxyphenyl n-butyrate and 4-methoxyphenyl n-butyrate. The olefinic mixture was separated in the next step as their epoxides.

Step C

To a mixture of E61, o-(1,2-dimethylallyl)-p-methoxyphenyl n-butyrate and p-methoxyphenyl n-butyrate (39.5 gm) in dichloromethane (900 mL) was added in portions metachloroperbenzoic acid (52 gm; 300 mmoles). The mixture was stirred at room temperature overnight. The reaction mixture was cooled in an ice-water bath and calcium hydroxide (150 gm) was added. After stirring for 15 minutes the mixture was filtered through a celite pad and the filtrate concentrated in vacuo. The residue was chromatographed in silica gel using 10% ethyl acetate in hexane to obtain 20 gm (47%) of o-(1,1-dimethyl-2,3-epoxypropyl)-p-methoxyphenyl n-butyrate, E62, as an oil.

$^1$H NMR δ: 1.03 (t, 3H, J=7.5 Hz), 1.2 (s, 3H), 1.3 (s, 3H), 1.6–2.0 (m, 2H), 2.43–2.83 (m, 4H), 3.06–3.20 (m, 1H), 3.76 (s, 3H) 6.6–7.06 (m, 3H).

Step D

To a solution of E62 (41 gm; 147 mmoles) in ethanol (600 mL) at 5° C. was added 0.5M sodium ethoxide in ethanol (328 mL). The mixture was stirred for 30 minutes and then water added. The mixture was extracted with diethyl ether, backwashed with brine, dried over MgSO, filtered and concentrated in vacuo to give 30 gm (98%) of 3,3-dimethyl-2-hydroxymethyl-5-methoxy-2,3-dihydrobenzofuran, E63, m.p. 65°–67° C.

$^1$H NMR δ: 1.13 (s, 3H), 1.33 (s, 3H), 1.96 (t, 1H, J=6 Hz), 3.6–3.93 (m, 5H), 4.2–4.4 (m, 1H), 6.5–6.8 (m, 3H).

Step E

To a solution of E63 (30 gm; 144 mmoles) in dichloromethane (1 L) at 78° C. was added dropwise 1M boran tribromide in dichloromethane (300 mL). The mixture was permitted to rise to room temperature over 1 hour and then re-cooled to 5° C. 1M sodium bicarbomate was added slowly and the mixture was stirred at room temperature until 2 clear layers were obtained. The organic layer was separated, dried over MgSO$_4$ filtered and concentrated in vacuo. The residue was chromatographed on silica gel using 40% ethylacetate in hexane as eluent to obtain 13.1 gm (47%) of 3,3-dimethyl-5-hydroxy-2-hydroxymethyl-2,3-dihydrobenzofuran, E64, m.p. 79°–80° C.

$^1$H NMR δ: 1.16 (s, 3H), 1.36 (s, 3H), 2.06 (t, 1H, J=6 Hz), 3.73–3.93 (m, 2H), 4.23–4.46 (m, 1H), 4.96 (s, 1H) 6.5–6.6 (m, 3H).

Step F

A mixture of E64 (14 gm; 72 mmoles), potassium carbonate (21 gm; 155 mmoles) and benzyl chloride (19.5 gm; 155 mmoles) in methyl ethyl ketone was stirred at reflux for 18 hours. The mixture was filtered through a celite pad and the filtrate concentrated in vacuo. The residue was chromatographed on silica gel using 30% ethyl acetate as eluent to obtain 14.5 gm (71%) of 5-benzyloxy-3,3-dimethyl-2-hydroxymethyl-2,3-dihydrobenzofuran, E65, m.p. 55°–58° C.

¹H NMR δ: 1.16 (s, 3H), 1.36 (s, 3H), 1.96 (t, 1H, J=6 Hz), 3.7–3.9 (m, 2H), 4.26–4.46 (m, 1H), 4.96 (s, 2H) 6.63–6.76 (m, 3H, 7.2–7.53 (m, 5H).

Step G

To a cold (−78° C.) solution of oxalyl chloride (1.78 gm, 14 mmoles) in CH₂Cl₂ (50 mL) was added DMSO (2.18 gm, 28 mmoles) in (10 ml) CH₂Cl₂ dropwise. This solution was stirred for 15 minutes. Then E65 (2.0 gm, 7 mmoles) was added and the resulting mixture was stirred at −78° C. for 30 minutes. To the reaction mixture was added ET₃N (3.55 gm, 35 mmoles) and the temperature was raised to room temperature. Then H₂O (100 mL) was poured into the reaction mixture and stirred for 15 minutes. The organic phase was separated from the aqueous. The organic phase was concentrated in vacuo, and the residue was chromatographed on silica gel. The elution with 15% ethyl acetate in hexane yielded 1.8 gm (91%) of 5-benzyloxy-3,3-dimethyl-2,3-dihydrobenzofuran-2-carboxyaldehyde, E66.

¹H NMR δ: 1.2 (s, 3H), 1.5 (s, 3H), 4.5 (d, J=1.5 Hz, 1H, methyne) 5 (s, 2H), 6.75 (m, 3H), 7.35 (m, 5H), 9.8 (d, J=1.5 Hz, 1H, aldehyde proton).

Step H

To p-methoxybenzyl diethyl phosphate (0.6 gm, 2.3 mmoles) cooled at −78° C. in THF (20 ml) was added potassium hexamethyl disilazide (3.6 mL, 2.3 mmoles) and the yellow solution was stirred for 30 minutes. Then E66 (0.2 gm, 0.7 mmoles) dissolved in 5 mL THF was added to the phosphonate solution. The reaction mixture was warmed to 0° C. and stirred for 30 minutes. Subsequently the reaction mixture was acidified with HCl 1N, diluted with brine and extracted with ethyl acetate twice. The combined organic phases were dried (Na₂SO₄) and evaporated. The residue was concentrated in vacuo and was chromatographed on silica gel. The elution with 10% ethyl acetate in hexane yielded 0.1 gm, (37%) of 2-(2-p-methoxystyryl)-3,3-dimethyl-5-benzyloxy-2,3-dihydrobenzofuran, E67.

¹H NMR δ: 1.1 (s, 3H), 1.35 (s, 3H), 3.7 (s, 3H), 4.75 (d, 1H, J=9 Hz), 4.95 (s, 2H, benzyloxy), 6.25 (dd, J=7.5 Hz, J″=12 Hz, 1H), 6.75 (m, 4H), 7.35 (m, 5H, benzyl).

EXAMPLE 24

One Step Preparation of 2-(2-p-methoxyphenylethyl)-3,3-dimethyl-5-hydroxy-2,3-dihydrobenzofuran

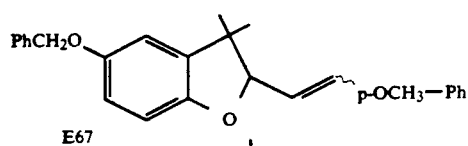

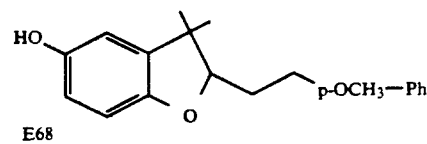

Step A

A solution of E67 (0.1 gm, 0.26 mmoles) in ethanol (5 mL) was hydrogenated in a Parr apparatus in the presence of 5% palladium on carbon for 4 hours. The catalyst was removed by filtration and the filtrate was concentrated to dryness. The residue was chromatographed on silica gel using 20% ethyl acetate in hexane as eluant to yield 60 mg, 78% of 2-(2-p-methoxyphenylethyl)-3,3-dimethyl-5-hydroxy-2,3-dihydrobenzofuran, E68.

¹H NMR δ: 1.05 (s, 3H), 1.18 (s, 3H), 1.5–2.1 (m, 2H), 2.4–3.1 (m, 2H), 3.7 (s, 3H), 4.1 (dd, J=3H, J′=9 Hz, 1H, methyne), 4.75 (m, 1H, OH), 6.55 (m, 3H), 6.8 (d, J=9 Hz, 2H), 7.1 (d, J=9 Hz, 2H).

EXAMPLE 25

Ten Step Preparation of 2-(2-p-chlorophenylethyl)-3,3-di-methyl-5-hydroxy-6-(3-phenoxypropyl)-2,3-dihydrobenzofuran E78

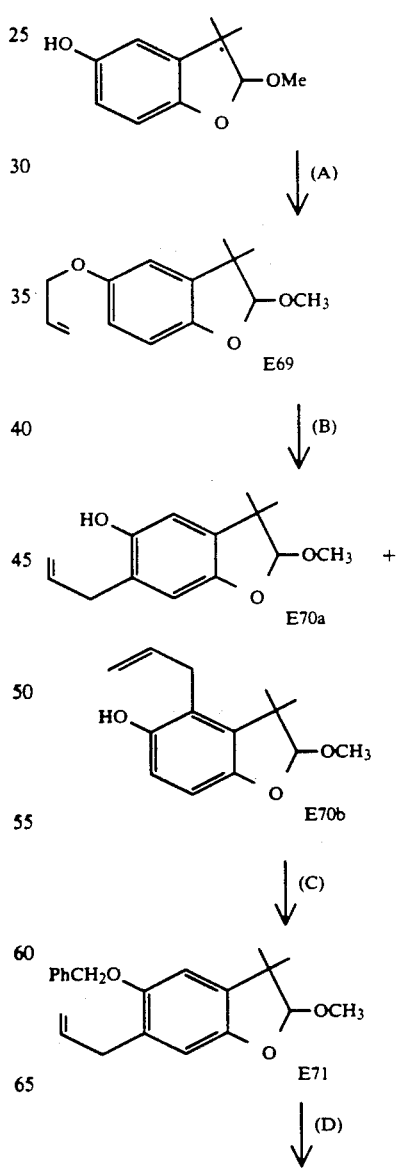

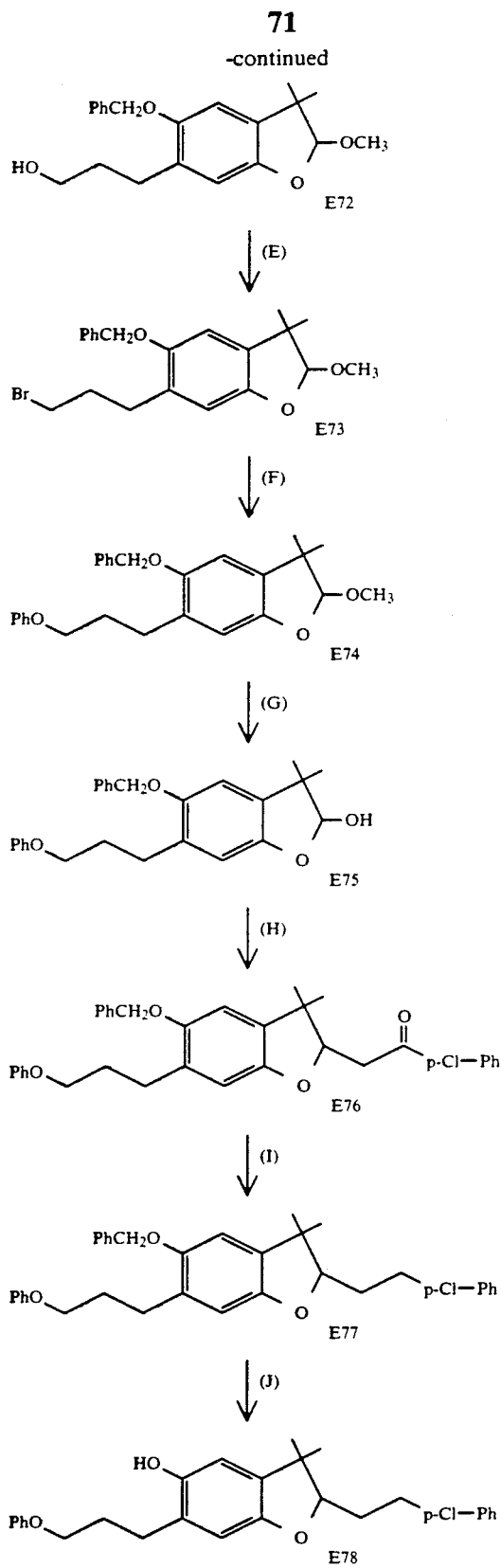

3346-3347. Otherwise, this material might be manufactured from compound 8 of Flow Sheet B. Firstly, an ozonolysis is performed with reductive work up to make an aldehyde of the potential 2-position carbon. Subsequently, this aldehyde is treated with methanol and acid to close the furanyl ring and produce a 2-position methoxy substitution. Finally, the 5-position protecting group is removed.

A mixture of starting material from above (74 gm; 380 mmoles), allylbromide (92 gm; 760 mmoles) potassium carbonate (104 gm; 760 mmoles) and methylethylketone (500 mL) was refluxed for 4 hours. The mixture was cooled, filtered through celite and the filtrate concentrated in vacuo. The residue was chromatographed on silica gel using 15% ethyl acetate in hexane as eluent to yield 68 gm (77%) of 5-allyloxy-3,3-dimethyl-2-methoxy-2,3-dihydrobenzofuran, E69 as an oil.

$^1$H NMR δ: 1.26 (s, 3H), 1.33 (s, 3H), 3.53 (s, 3H), 1.4-4.63 (m, 2H), 5.0-5.63 (m, 2H), 5.8-6.4 (m, 1H), 6.73 (s, 2H).

Step B

A mixture of E69 (68 gm; 290 mmoles) in 1,2-dichlorobenzene (136 mL) was refluxed under nitrogen atmosphere for 18 hours. The mixture was concentrated in vacuo to remove most of the dichlorobenzene and the residue was chromatographed on silica gel using 5% ethyl acetate in hexane to obtain 51 gm (75%) of 6-allyl-3,3-dimethyl-5-hydroxy-2-methoxy-2,3-dihydrobenzofuran, E70a, as an oil. The more polar isomeric 4-allyl-3,3-dimethyl-5-hydroxy-2-methoxy-2,3-dihydrobenzofuran, E70b, 10 gm (15%) was also isolated as an oil.

6-allyl isomer E70a $^1$H NMR δ: 1.24 (s, 3H), 1.28 (s, 3H), 3.28-3.40 (m, 2H) 3.52 (s, 3H) 4.87 (s, 1H), 5.04-5.22 (m, 3H), 5.88-6.07 (m, 1H), 6.55-6.63 (m, 2H).

4-allyl isomer E70b $^1$H NMR δ: 1.40 (s, 3H), 1.46 (s, 3H), 3.0-3.66 (m, 5H), 4.73-5.30 (m, 4H), 5.73-6.33 (m, 1H), 6.73 (s, 2H).

Step C

A mixture of E70a (12 gm; 51 mmoles) potassium carbonate (20 gm; 150 mmoles), benzyl chloride (19 gm; 150 mmoles) and methylethylketone (300 mL) was refluxed for 22 hours. The mixture was filtered through celite, concentrated in vacuo and the reside was chromatographed on silica gel using 5% ethyl acetate as eluent to obtain 15 gm (90%) of 6-allyl-5-benzyloxy-3,3-dimethyl-2-methoxy-2,3-dihydrobenzofuran, E71, as an oil.

$^1$H NMR δ: 1.24 (s, 3H), 1.28 (s, 3H), 3.28-3.40 (m, 2H), 3.52 (s, 3H), 4.73-5.33 (m, 5H), 5.66-6.33 (m, 1H), 6.66 (s, 2H), 7.16-7.63 (m, 5H).

Step D

To a solution of E71 (14 gm; 43 mmoles) in tetrahydrofuran at 0° C. was added dropwise over 15 minutes 1 molar diborane in tetrahydrofuran (250 mL). The mixture was stirred for 75 minutes and then methanol (40 mL) was added dropwise followed by 1N sodium hydroxide (50 mL) and 30% hydrogen peroxide (20 mL). After stirring for 30 minutes, a solution of sodium sulfite (18 gm, 3.0 mmoles) in water (120 mL) was added slowly. Diethyl ether (500 mL) was then added. The organic layer was separated, washed with brine, dried (MgSO$_4$), filtered and concentrated in vacuo. The

Step A

Starting material, 3,3-dimethyl-5-hydroxy-2-2,3-dihydrobenzofuran was purchased on the market. Also, it is a material readily available from benzoquinone by the procedure of G. Allen, Jr., J. Org. Chem. (1968)

crude was chromatographed on silica gel using 20% ethyl acetate in hexane to yield 9.1 gm (65%) of 5-benzyloxy-3,3-dimethyl-6-(3-hydroxypropyl)-2-methoxy-2,3-dihydrobenzofuran, E72, as an oil.

$^1$H NMR δ: 1.23 (s, 3H), 1.30 (s, 3H), 1.53-2.06 (m, 3H), 2.70 (t, 2H, J=9.3 Hz), 3.36-3.70 (m, 5H), 5.0 (s, 2H), 5.03 (s, 1H), 6.66 (s, 1H), 6.70 (s, 1H), 7.2-7.6 (m, 5H).

Step E

To a solution of E72 (9.1 gm; 28 mmoles) and triphenylphosphine (14.7 gm; 156 mmoles), in dichloromethane (600 mL) was added carbon tetrabromide (18.5 gm; 56 mmoles). The mixture was stirred for 45 minutes and concentrated in vacuo. The residue was slurried with diethyl ether and the heterogeneous mixture filtered through celite. The filtrate was concentrated in vacuo and the crude residue was chromatographed using 15% ethyl acetate in hexane to yield 7.7 gm (68%) of 5-benzyloxy-6-(3-bromopropyl)-3,3-dimethyl-2-methoxy-2,3-dihydrobenzofuran, E73, as an oil.

$^1$H NMR δ: 1.26 (s, 3H), 1.3 (s, 3H), 1.93-2.33 (m, 2H) 1.76 (t, 2H, J=7.4 Hz), 3.36 (t, 2H, J=7.4 Hz), 3.56 (s, 3H), 5.0 (s, 2H), 5.03 (s, 1H), 6.7 (s, 2H) 7.23-7.56 (m, 5H).

Step F

A solution of E73 (7.7 gm; 19 mmoles) in dimethylformamide (20 mL) was added under nitrogen atmosphere to a mixture of phenol (4.7 gm; 50 mmoles), and 50% sodium hydroxide dispersion (2.4 gm; 50 mmoles) in dimethylformamide (250 mL). The mixture was stirred at room temperature for 1 hour and then poured into 20% citric acid solution (500 mL) and the lot extracted with diethyl ether. The organic layer was washed with water, 1N sodium hydroxide twice, dried (MgSO$_4$) filtered and concentrated in vacuo to obtain 7.1 gm (90%) of 5-benzyloxy-3,3-dimethyl-6-(3-phenoxypropyl)-2-methoxy-2,3-dihydrobenzofuran, E74, as an oil.

$^1$H NMR δ: 1.23 (s, 3H), 1.3 (s, 3H), 1.9-2.26 (m, 2H), 2.76 (t, 2H, J=7.4 Hz), 3.5 (s, 3H), 3.93 (t, 2H, J=7.4 Hz), 5.0 (s, 2H), 5.03 (s, 1H), 6.6-7.63 (m, 12H).

Step G

A solution of E74 (7.1 gm; 16.9 mmoles) acetic acid (320 mL) and water (80 mL) was refluxed under nitrogen atmosphere for 18 hours. The mixture was concentrated. The residue was dissolved in diethyl ether and washed with 1N sodium bicarbonate, dried (MgSO$_4$), filtered and concentrated in vacuo. The residue was chromatographed on silica gel using 15% ethyl acetate in hexane as eluent to obtain 5.4 gm (78%) of 5-benzyloxy-3,3-dimethyl-2-hydroxy-6-(3-phenoxypropyl)-2,3-dihydrobenzofuran, E75, as an oil.

$^1$H NMR δ: 1.26 (s, 3H), 1.33 (s, 3H), 1.86-2.26 (m, 1H), 2.66-3.10 (m, 3H), 3.93 (t, 2H, J=7.4 Hz), 5.0 (s, 2H), 5.46 (d, 1H, J=7.4 Hz), 6.56-7.0 (m, 4H), 7.1-7.6 (m, 8H).

Step H

To a solution of E75 (2.5 gm; 6.1 mmoles) and 2-(p-chlorophenyl)-2-oxoethyl diethylphosphonate (8 gm; 21 mmoles) in dimethylformamide (110 mL) was added potassium-t-butoxide (4.1 gm; 37 mmoles) in one portion. The mixture was stirred at room temperature for 15 minutes and then heated in an oil bath at 110°-120° C. for 2 hours. The mixture was cooled, poured into 1N hydrochloric acid (300 mL) and extracted with diethyl ether. The ether layer was washed twice with water, dried (MgSO$_4$), filtered concentrated in vacuo and the residue chromatographed on silica gel using 15% ethylacetate in hexane as eluent to obtain 1.5 gm (45%) of 5-benzyloxy-2-[2-(p-chlorophenyl)-2-oxoethyl]-3,3-dimethyl-6-(3-phenoxypropyl)-2,3-dihydrobenzofuran, E76, as an oil.

$^1$H NMR δ: 1.23 (s, 3H), 1.4 (s, 3H), 1.86-2.3 (m, 2H), 2.66-3.26 (m, 4H), 4.0 (t, 2H, J=7.4 Hz), 4.8-5.1 (m, 3H), 6.6-7.06 (m, 4H), 7.06-7.66 (m, 10H), 8.0 (d, 2H, J=11.1 Hz).

Step I

A mixture of E76 (1.2 gm; 2.2 mmoles), triethylsilane (50 mL) and boron trifluoride etherate (1.2 mL; 10 mmoles) in 1,2-dichloroethane (50 mL) was stirred at room temperature for 3 hours. The mixture was poured into water and extracted with diethyl ether. The ether layer was washed with 1N sodium bicarbonate, dried (MgSO$_4$), filtered concentrated in vacuo. The residue was chromatographed on silica gel using 10% ethyl acetate in hexane as eluent to obtain 780 mgs (67%) of 5-benzyloxy-2-(2-p-chlorophenylethyl)-3,3-dimethyl-6-(3-phenoxypropyl)-2,3-dihydrobenzofuran, E77, as an oil.

$^1$H NMR δ: 1.10 (s, 3H), 1.28 (s, 3H), 1.73-2.18 (m, 4H), 2.65-3.09 (m, 4H), 3.98 (t, 2H, J=7.4 Hz), 4.06-4.18 (m, 1H), 5.04 (s, 2H), 6.73 (s, 1H), 6.74 (s, 1H), 6.77-6.97 (m, 2H), 7.03-7.46 (m, 12H).

Step J

To a solution of E77 (750 mgs; 1.4 mmoles), in dichloromethane (120 mL) at −78° C. was added dropwise 1M boron tribromide in dichloromethane (1.7 mL). The mixture was stirred for 10 minutes and then methanol (5 mL) was added followed by solid potassium carbonate (1 gm, 7.2 mmoles). The mixture was stirred at room temperature for 15 minutes, filtered and the filtrate concentrated in vacuo. The residue was chromatographed on silica gel using 15% ethyl acetate in hexane as eluent to obtain 330 mgs (53%) of 2-(2-p-chlorophenylethyl)-3,3-dimethyl-5-hydroxy-6-(3-phenoxypropyl)-2,3-dihydrobenzofuran, E78, as an oil.

$^1$H NMR δ: 1.10 (s, 3H), 1.28 (s, 3H), 1.74-2.25 (m, 4H), 2.62-3.12 (m, 4H), 4.03 (t, 2H, J=7.4 Hz), 4.10-4.21 (m, 1H), 5.3 (s, 1H), 6.61 (s, 1H), 6.64 (s, 1H), 6.82-7.42 (m, 14H).

EXAMPLE 26

Nine Step Synthesis of 3,3-dimethyl-5-hydroxy-2-(2-p-methylthiophenylethyl)-6-propyl-2,3-dihydrobenzofuran E87

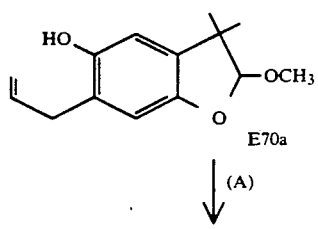

E70a

↓ (A)

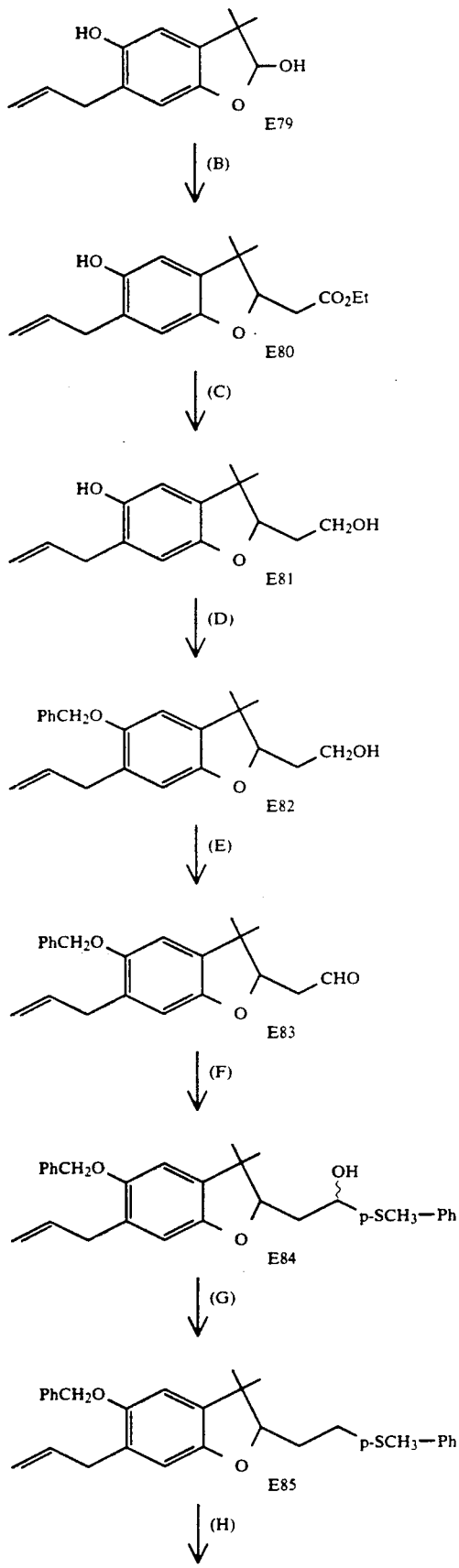

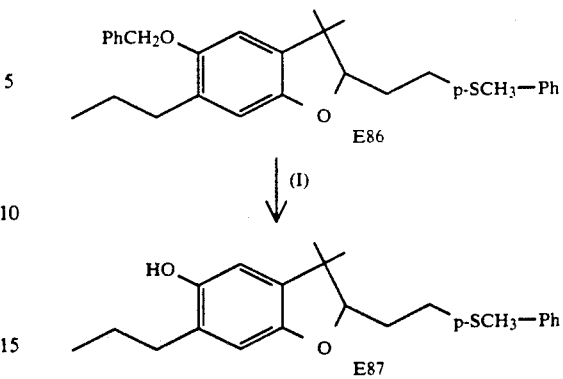

Step A

A mixture of 6-allyl-3,3-dimethyl-5-hydroxy-2-methoxy-2,3-dihydrobenzofuran, E70a, (20 gm; 85 mmoles), acetic acid (160 mL) and water (40 mL) was refluxed for 18 hours. The mixture was concentrated in vacuo and the residue chromatographed on silica gel using 20% ethyl acetate in hexane as eluent to obtain 17.8 gm (94%) of 6-allyl-2,5-dihydroxy-3,3-dimethyl-2,3-dihydrobenzofuran, E79, m.p. 66°–67° C.

$^1$H NMR δ: 1.23 (s, 3H), 1.3 (s, 3H), 3.16–3.46 (m, 2H), 4.66–5.6 (m, 5H), 5.7–6.26 (m, 1H), 6.6 (s, 2H).

Step B

A mixture of E79 (30 gm; 138 mmoles), carbethoxymethylene triphenylphosphorane (125 gm; 360 mmoles) and tetrahydrofuran (650 mL) was refluxed for 20 hours. The mixture was concentrated in vacuo and the residue chromatographed on silica gel using 30% ethyl acetate in hexane as eluent to obtain 33 gms (82%) of 6-allyl-2-carbethoxymethyl-3,3-dimethyl-5-hydroxy-2,3-dihydrobenzofuran, E80.

$^1$H NMR δ: 1.1–1.4 (m, 9H), 2.53–2.76 (m, 2H), 3.2–3.4 (m, 2H), 4.2 (q, 2H, J=13 Hz), 4.53–4.8 (m, 2H), 4.93–5.3 (m, 2H), 5.63–6.23 (m, 1H), 6.36 (s, 1H), 6.40 (s, 1H).

Step C

To a solution of E80 (11.9 gm; 41 mmoles) in tetrahydrofuran (500 mL) at 5° C. and under nitrogen atmosphere was added dropwise a 1.5 molar solution in toluene of Dibal-M (110 mL; 164 mmoles). The mixture was stirred for 10 minutes and then poured slowly into a stirring mixture of 3N hydrochloric acid (300 mL) and ice (300 mL). After stirring for 30 minutes and the addition of ethyl acetate to facilitate separation, the organic layer was separated, dried (MgSO$_4$), filtered and concentrated in vacuo. The residue was chromatographed on silica gel using 30% ethyl acetate in hexane as eluent to obtain 9.9 gm (97%) of 6-allyl-3,3-dimethyl-5-hydroxy-2-(2-hydroxyethyl)-2,3-dihydrobenzofuran, E81, m.p. 55°–58° C.

$^1$H NMR δ: 0.96 (s, 3H), 1.16 (s, 3H), 1.56–2.33 (m, 3H), 3.1–3.3 (m, 2H), 3.66–4.30 (m, 3H), 4.86–5.2 (m, 3H), 5.6–6.23 (m, 1H) 6.43 (s, 1H), 6.46 (s, 1H).

Step D

A mixture of E81 (7.5 gm; 30 mmoles), potassium carbonate (12.4 gm; 90 mmoles) and benzyl chloride (11.3 gm; 90 mmoles) in methyl ethyl ketone (200 mL) was refluxed for 18 hours. Another portion of benzyl chloride (2.75 gm; 21 mmoles) and potassium carbonate (3.1 gm; 21 mmoles) was added and refluxing continued for 7 more hours. The mixture was cooled, filtered and the filtrate concentrated in vacuo. The residue was chromatographed on silica gel using 30% ethyl acetate in hexane as eluent to obtain 9.4 gm (92%) of 6-allyl-5-benzyloxy-3,3-dimethyl-2-(2-hydroxyethyl)-2,3-dihydrobenzofuran, E82, as an oil.

$^1$H NMR δ: 1.13 (s, 3H), 1.33 (s, 3H), 1.73-2.3 (m, 3H), 3.26-3.50 (m, 2H), 3.93-4.06 (m, 2H), 4.2-4.46 (m, 1H), 4.86-5.23 (m, 4H) 6.66 (s, 1H), 6.73 (s, 1H), 7.23-7.6 (m, 5H).

Step E

Dimethyl sulfoxide (1.71 gm; 22 mmoles) was added dropwise to oxalyl chloride (1.39 gm; 11 mmoles) in dichloromethane (125 mL) at −78° C. To this mixture was added a solution of E82 (2.5 gm; 7.4 mmoles) in dichloromethane (25 mL). After stirring for 20 minutes triethylamine (4.4 gm; 44 mmoles) was added and the mixture brought up to room temperature and then diluted with water. The organic layer was separated, dried (MgSO$_4$), filtered and concentrated in vacuo to obtain 2.8 gm of 6-allyl-5-benzyloxy-3,3-dimethyl-2-formylmethyl-2,3-dihydrobenzofuran, E82, as an oil which was used in the next step without further purification.

$^1$H NMR δ: 1.1 (s, 3H), 1.33 (s, 3H), 2.43-3.03 (m, 2H) 3.36 (d, 2H, J=7.4 Hz), 4.7 (q, 1H, J=11 Hz, J'=5.5 Hz), 4.83-5.23 (m, 4H), 5.6-6.2 (m, 1H), 6.63 (s, 1H), 6.7 (s, 1H), 7.13-7.56 (m, 5H), 9.9 (t, 1H, J=1.86 Hz).

Step F

To a solution of E83, (2.8 gm; 7.4 mmoles) in tetrahydrofuran (125 mL) at 5° C. was added the Grignard reagent p-methylthiophenyl magnesium bromide in tetrahydrofuran (0.8 molar) (19 mL; 15 mmoles) which was previously prepared by refluxing for 2 hours a mixture of p-bromothioanisole (8.1 gm; 40 mmoles) and magnesium turnings (1 gm; 41 mmoles) in tetrahydrofuran (50 ml). The mixture was stirred for 1 hour at room temperature and then excess 1N hydrochloric acid was added. The organic layer was separated dried (MgSO$_4$), filtered and concentrated in vacuo. The residue was chromatographed on silica gel using 30% ethyl acetate as eluent to obtain 3.1 gm (91%) of 6-allyl-5-benzyloxy-3,3-dimethyl-2[2-hydroxy-2-(p-methylthiophenylethyl)-2,3-dihydrobenzofuran, E84 as an oil (erythro-threo isomer mixture).

$^1$H NMR δ: 1.06 (s, 3H), 1.23 (s, 3H), 1.63-2.2 (m, 2H), 2.3-2.56 (m, 4H), 3.23-3.53 (m, 3H), 4.06-4.6 (m, 1H), 4.8-5.3 (m, 4H) 5.7-6.26 (m, 1H), 6.66 (s, 2H), 6.8-7.73 (m, 9H).

Step G

A mixture of E84, (3.1 gm; 6.7 mmoles) zinc iodide (3.2 gm; 10 mmoles) and sodium cyanoborohydride (3.1 gm; 50 mmoles) in 1,2-dichloroethane (125 mL) was refluxed for 18 hours under nitrogen atmosphere. The mixture was filtered and the filtrate stirred for 15 minutes with 3N hydrochloric acid (50 mL). The organic layer was separated, dried (MgSO$_4$), filtered and concentrated. The residue was chromatographed on silica gel using 15% ethyl acetate in hexane as eluent to obtain 750 mgs (25%) of 6-allyl-5-benzyloxy-3,3-dimethyl-2-(2-p-methylthiophenylethyl)-2,3-dihydrobenzofuran, E85, as an oil.

$^1$H NMR δ: 1.08 (s, 3H), 1.28 (s, 3H), 1.63-2.23 (m, 2H), 2.15 (s, 3H), 2.56-3.23 (m, 2H), 3.3-3.5 (m, 2H), 4.11 (dd, 1H, J=7.45 Hz, J'=3.7 Hz), 4.86-5.2 (m, 4H), 5.6-6.3 (m, 1H), 6.63 (s, 1H), 6.66 (s, 1H), 6.93-7.63 (m, 9H).

Step H

A mixture of E85, (744 mgs; 1.6 mmoles), ethanol (25 mL), ethyl acetate (25 mL) and 10% palladium on carbon (700 mgs) was hydrogenated on a Parr apparatus for 1.5 hours at 40 psi. The mixtured was filtered through celite and the filtrated concentrated to obtain 667 mgs (89%) of 5-benzyloxy-3,3-dimethyl-2-(2-p-methylthiophenylethyl)-6-propyl-2,3-dihydrobenzofuran, E86, as an oil.

$^1$H NMR δ: 0.73-2.16 (m, 13H), 2.36-3.16 (m, 7H), 4.16 (dd, 1H, J=9.3 Hz, J'=3.7 Hz), 5.0 (s, 2H), 6.66 (s, 1H), 6.70 (s, 1H), 7.0-7.66 (m, 9H).

Step I

A mixture of E86, (55 mgs; 0.123 mmoles), acetic acid (4.5 mL) and 6N hydrochloric acid (0.5 mL) was heated in an oil bath maintained at 115° C. for 1 hour. The mixture was partitioned between diethyl ether and water. The ether layer was washed with saturated sodium bicarbonate solution, dried (MgSO$_4$), filtered and concentrated in vacuo. The residue was chromatographed on silica gel using 15% ethyl acetate in hexane as eluent to obtain 22 mgs (50%) of 3,3-dimethyl-5-hydroxy-2-(2-p-methylthiophenylethyl)-6-propyl-2,3-dihydrobenzofuran, E87, as an oil.

$^1$H NMR δ: 0.7-2.3 (m, 13H), 2.3-3.26 (m, 7H), 4.0-4.56 (m, 2H), 6.53 (s, 1H), 6.6 (s, 1H), 7.06-7.36 (m, 5H).

What is claimed is:

1. The leukotriene biosynthesis inhibitor of the formula:

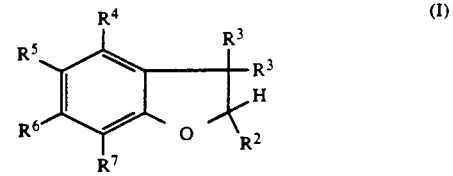

(I)

wherein:

R$^2$ is

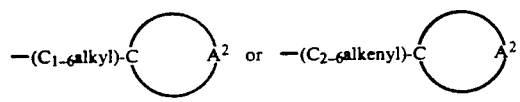

with A$^2$ completing a ring selected from the group consisting of (Y$^6$)$_5$ substituted phenyl or (Y$^6$)$_7$ substituted naphthyl;

R$^3$ is independently, hydrogen or C$_{1-6}$alkyl;

R$^5$ is hydroxy or metabolizeable to hydroxy;

R$^4$ is hydrogen, halogen, —C$_{1-6}$alkyl, C$_{2-6}$alkenyl, —(C$_{1-6}$alkyl)—R$^{6a}$, —(C$_{2-6}$alkenyl)—R$^{6a}$, —(C$_{1-6}$alkyl)$_p$—OR$^{6b}$, —(C$_{2-6}$alkenyl)—OR$^{6b}$, —(C$_{1-6}$alkyl)$_p$—SR$^{6b}$, —(C$_{2-6}$alkenyl)—SR$^{6b}$, —(C$_{1-6}$alkyl)$_p$—S(O)R$^{6b}$, —(C$_{2-6}$alkenyl)—S(O)R$^{6b}$, —(C$_{1-6}$alkyl)$_p$—S(O)$_2$R$^{6b}$, —(C$_{2-6}$alkenyl)-S(O)$_2$R$^{6b}$, —(C$_{1-6}$alkyl)$_p$—N(R$^{6c}$)(R$^{6b}$) or —(C$_{2-6}$alkenyl)—N(R$^{6c}$)(R$^{6b}$);

R$^6$ is, hydrogen, halogen, C$_{2-6}$alkenyl, —(C$_{1-6}$alkyl)—R$^{6a}$, —(C$_{2-6}$alkenyl)—R$^{6a}$, —(C$_{1-6}$alkyl)$_p$—OR$^{6b}$, —(C$_{2-6}$alkenyl)—OR$^{6b}$, —(C$_{1-6}$alkyl)-

$p$—SR$^{6b}$, —(C$_{2-6}$alkenyl)—SR$^{6b}$, —(C$_{1-6}$alkyl)-$p$—S(O)R$^{6b}$, —(C$_{2-6}$alkenyl)—S(O)R$^{6b}$, —(C$_{1-6}$alkyl)$_p$—S(O)$_2$R$^{6b}$, —(C$_{2-6}$alkenyl)S(O)$_2$R$^{6b}$, —(C$_{1-6}$alkyl)$_p$—N(R$^{6c}$)(R$^{6b}$) or —(C$_{2-6}$alkenyl)—N(R$^{6c}$)(R$^{6b}$), provided that when one of R$^4$ or R$^6$ is hydrogen or halogen then the other is not hydrogen or halogen and provided that R$^6$ is not —O—C$_{1-6}$alkyl when R$^4$ is —C$_{1-6}$alkyl;

R$^7$ is hydrogen, halogen or C$_{2-6}$alkenyl;

R$^{6a}$ is (Y$^6$)$_5$ substituted phenyl, (Y$^6$)$_7$ substituted naphthyl, —C(O)NR$^{6c}$, or

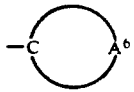

where A$^6$ completes a substituted or unsubstituted 6-membered heterocycle, substituted or unsubstituted 5-membered heterocycle having fused thereto a (Y$^2$)$_{3\ or\ 4}$ substituted benzene ring, or a substituted or unsubstituted 6-membered heterocycle having fused thereto a (Y$^2$)$_{3\ or\ 4}$ substituted benzene ring (wherein said 6-membered heterocycles are selected from the group consisting of alpha-pyronyl, gamma-pyronyl, pyridinyl, pyridazinyl, pyrimidinyl, pyrazinyl and thiopyronyl, wherein said 5-membered heterocycles fused with a benzene ring are selected from the group consisting of benzofuran-2-yl, benzofuran-6-yl, benzothiophen-2-yl benzothiophen-5-yl, indol-2-yl, indol-5-yl, benzopyrazol-3-yl, benzopyrazol-5-yl, benzimidazol-2-yl, benzimidazol-5-yl, benzoxazol-2-yl and benzoxazol-5-yl, wherein said 6-membered heterocycles fused with a benzene ring are selected from the group consisting of quinolin-2-yl, quinolin-4-yl, quinolin-7-yl, isoquinolin-1-yl, isoquinolin-3-yl, isoquinolin-7-yl, cinnolin-3-yl and quinazolin-2-yl, and where the heterocycle substituents are selected from the group consisting of hydrogen, C$_{1-6}$alkyl, phenyl, halogen, —C(O)OH, —C(O)OC$_{1-6}$alkyl and —OC$_{1-6}$alkyl);

R$^{6b}$ is C$_{1-6}$alkyl, C$_{2-6}$alkenyl, —(C$_{1-6}$alkyl)$_p$—((Y$^6$)$_7$ substituted naphthyl), —(C$_{1-6}$alkyl)$_p$—((Y$^6$)$_5$ substituted phenyl), —(C$_{1-6}$alkyl)—C(O)N(R$^{6c}$)$_2$, —(C$_{1-6}$alkyl)—C(O)OR$^{6c}$ or

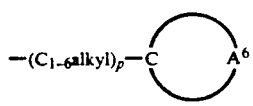

(where A$^6$ is defined immediately above);
R$^{6c}$ is hydrogen or C$_{1-6}$alkyl;

Y$^2$ is —H, halogen, —OH, C$_{1-6}$alkyl, —CN, —CF$_3$, —(C$_{1-6}$alkyl)$_p$—O—C$_{1-6}$alkyl, —(C$_{1-6}$alkyl)-$p$—S—C$_{1-6}$alkyl, —(C$_{1-6}$alkyl)$_p$—S(O)—C$_{1-6}$alkyl, —(C$_{1-6}$alkyl)$_p$—S(O)$_2$—C$_{1-6}$alkyl, —(C$_{1-6}$alkyl)-$p$—C(O)—C$_{1-6}$alkyl, —O—(C$_{1-6}$alkyl)$_p$—C(O)OR$^{6c}$, —(C$_{1-6}$alkyl)$_p$—C(O)OR$^{6c}$, —(C$_{1-6}$alkyl)$_p$—C(O)NHOR$^{6c}$, —(C$_{1-6}$alkyl)$_p$—C(O)NHR$^{6c}$, —(C$_{1-6}$alkyl)$_p$—NHC(O)O(C$_{1-6}$alkyl), —(C$_{1-6}$alkyl)$_p$—NHR$^{6c}$, —(C$_{1-6}$alkyl)$_p$—NHS(O)$_2$—C$_{1-6}$alkyl, —(C$_{1-6}$alkyl)$_p$—NHS(O)$_2$—(R$^7$)$_5$ substituted phenyl, or —(C$_{1-6}$alkyl)$_p$—NO$_2$;

Y$^6$ is Y$^2$ or

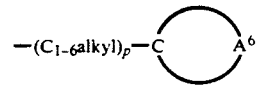

(where A$^6$ is defined immediately above); and
p is 0 or 1.

2. The compound of claim 1 wherein —C$_{1-6}$alkyl is selected from the group consisting of methyl, ethyl, propyl, i-butyl, t-butyl, n-butyl, pentyl, hexyl, cyclopropyl, and cyclohexyl.

3. The compound of claim 1 wherein —C$_{2-6}$alkenyl is selected from the group consisting of —CHCH$_2$, —CH$_2$CHCH$_2$, —CH$_2$CHCHCH$_3$ and —CH$_2$C(CH$_3$)CH$_2$.

4. The compound of claim 1 wherein —(C$_{1-6}$alkyl)— is selected from the group consisting of —CH$_2$—, —(CH$_2$)$_2$—, —(CH$_2$)$_3$—, —(CH$_2$)—C—(CH$_3$)$_2$— and —(CH$_2$)—C—(CH$_3$)—.

5. The compound of claim 1 wherein —(C$_{2-6}$alkenyl)— is selected from the group consisting of —CHCH—, —CH$_2$CHCH—, —CH$_2$CH$_2$CHCH— and —CH$_2$C—(CH$_3$)CH—.

6. The compound of claim 1 wherein said heterocycles are aromatic.

7. The compound of claim 1 wherein said R$^2$ is —(C$_{1-6}$alkyl)—(Y$^6$)$_5$ substituted phenyl or —(C$_{2-6}$alkenyl)—(Y$^6$)$_5$ substituted phenyl.

8. The compound of claim 1 wherein R$^5$ is selected from the group consisting of hydroxy, —OC(O)—(C$_{1-6}$alkyl), —OC(O)O—(C$_{1-6}$alkyl), —OC(O)O—(phenyl), —OC(O)—(phenyl), —OSO$_3$NH$_4$, —OC(O)NR$_2$', —O(O)P(OH)$_2$, —OC(O)—(C$_{1-6}$alkyl)—COOR' and —OC(O)—(C$_{1-6}$alkyl)—NR$_2$'.HCl, where R' is hydrogen, C$_{1-6}$alkyl or phenyl.

9. The compound of claim 1 wherein R$^4$ is selected from the group consisting of hydrogen, halogen, —C$_{1-6}$alkyl and C$_{2-6}$alkenyl.

10. The compound of claim 1 wherein R$^6$ is selected from the group consisting of —(C$_{1-6}$alkyl)—R$^{6a}$, —(C$_{2-6}$alkenyl)—R$^{6a}$, —(C$_{1-6}$alkyl)$_p$—OR$^{6b}$, —(C$_{2-6}$alkenyl)—OR$^{6b}$, —(C$_{1-6}$alkyl)$_p$—SR$^{6b}$, —(C$_{2-6}$alkenyl)—SR$^{6b}$, —(C$_{1-6}$alkyl)$_p$—S(O)R$^{6b}$, —(C$_{2-6}$alkenyl)—S(O)R$^{6b}$, —(C$_{1-6}$alkyl)$_p$—S(O)$_2$R$^{6b}$ and —(C$_{2-6}$alkenyl)—S(O)$_2$R$^{6b}$.

11. The compound of claim 1 wherein R$^{6a}$ is (Y$^6$)$_5$ substituted phenyl, or

12. The compound of claim 1 wherein R$^{6a}$ is (Y$^6$)$_5$ substituted phenyl or

13. The compound of claim 1 wherein R$^{6b}$ is —(C$_{1-6}$alkyl)$_p$—((Y$^6$)$_7$ substituted naphthyl), —(C$_{1-6}$alkyl)-$p$—((Y$^6$)$_5$ substituted phenyl), —(C$_{1-6}$alkyl)—C(O)N(R$^{6c}$)$_2$, —(C$_{1-6}$alkyl)—C(O)OR$^{6c}$ or

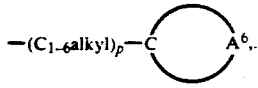

14. The compound of claim 1 wherein $R^{6b}$ is —($C_{1-6}$alkyl)$_p$—(($Y^6$)$_5$ substituted phenyl), —($C_{1-6}$alkyl)—C(O)OR$^{6c}$, or

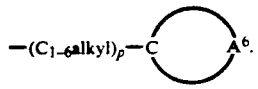

15. The compound of claim 1 wherein $R^{6b}$ is —($C_{1-6}$alkyl)$_p$—(($Y^6$)$_5$ substituted phenyl) or

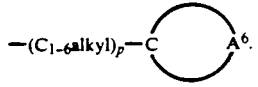

16. The compound of claim 1 wherein $A^6$ completes substituted or unsubstituted 6-membered heterocycle, or a substituted or unsubstituted 6-membered heterocycle having fused thereto a $(Y^2)_{3\text{ or }4}$ substituted benzene ring.

17. The compound of claim 1 wherein where $A^6$ completes substituted or unsubstituted 6-membered aromatic heterocycle (where the heterocycle contains 1 to 3 nitrogens the valences of which are satisfied by the ring and heterocycle substitution are defined above).

18. The compound of claim 1 wherein $Y^2$ is —H, halogen, —OH, $C_{1-6}$alkyl, —CN, —CF$_3$, —($C_{1-6}$alkyl)$_p$—O—$C_{1-6}$alkyl, —($C_{1-6}$alkyl)$_p$—S—$C_{1-6}$alkyl, —($C_{1-6}$alkyl)$_p$—S(O)—$C_{1-6}$alkyl, —($C_{1-6}$alkyl)$_p$—S(O)$_2$—$C_{1-6}$alkyl, —O—($C_{1-6}$alkyl)$_p$—C(O)OR$^{6c}$, —($C_{1-6}$alkyl)$_p$—C(O)OR$^{6c}$, —($C_{1-6}$alkyl)$_p$—C(O)NHOR$^{6c}$, —($C_{1-6}$alkyl)$_p$—C(O)NHR$^{6c}$, —($C_{1-6}$alkyl)$_p$—NHC(O)O($C_{1-6}$alkyl), —($C_{1-6}$alkyl)$_p$—NHS(O)$_2$—$C_{1-6}$alkyl, —($C_{1-6}$alkyl)$_p$—NHS(O)$_2$—($R^7$)$_5$ substituted phenyl, or —($C_{1-6}$alkyl)$_p$—NO$_2$.

19. The compound of claim 1 wherein $Y^2$ is —H, halogen, —OH, $C_{1-6}$alkyl, —CN, —CF$_3$, —($C_{1-6}$alkyl)$_p$—O—$C_{1-6}$alkyl, —($C_{1-6}$alkyl)$_p$—S—$C_{1-6}$alkyl, —($C_{1-6}$alkyl)$_p$—S(O)—$C_{1-6}$alkyl, —($C_{1-6}$alkyl)$_p$—S(O)$_2$—$C_{1-6}$alkyl, —O—($C_{1-6}$alkyl)$_p$—C(O)OR$^{6c}$, —($C_{1-6}$alkyl)$_p$—C(O)OR$^{6c}$, —($C_{1-6}$alkyl)$_p$—C(O)NHOH, —($C_{1-6}$alkyl)$_p$—C(O)NHR$^{6c}$ or —($C_{1-6}$alkyl)$_p$—NHS(O)$_2$—($R^7$)$_5$ substituted phenyl.

20. The compound of claim 1 wherein $R^7$ is hydrogen or halogen.

21. The leukotriene biosynthesis inhibitor of the formula:

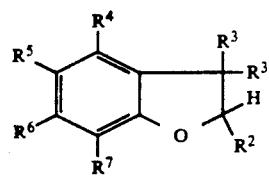

(I)

wherein
$R^2$ is —($C_{1-6}$alkyl)—($Y^6$)$_5$ substituted phenyl or —($C_{2-6}$alkenyl)—($Y^6$)$_5$ substituted phenyl;
$R^3$ is independently hydrogen or $C_{1-6}$alkyl;
$R^5$ is hydroxy or metabolizeable to hydroxy:

$R^4$ is hydrogen, halogen, —$C_{1-6}$alkyl, $C_{2-6}$alkenyl, —($C_{1-6}$alkyl)—R$^{6a}$, —($C_{2-6}$alkenyl)—R$^{6a}$, —($C_{1-6}$alkyl)$_p$—OR$^{6b}$, —($C_{2-6}$alkenyl)—OR$^{6b}$, —($C_{1-6}$alkyl)$_p$—SR$^{6b}$, —($C_{2-6}$alkenyl)—SR$^{6b}$, —($C_{1-6}$alkyl)$_p$—S(O)R$^{6b}$, —($C_{2-6}$alkenyl)—S(O)R$^{6b}$, —($C_{1-6}$alkyl)$_p$—S(O)$_2$R$^{6b}$, —($C_{2-6}$alkenyl)—S(O)$_2$R$^{6b}$, —($C_{1-6}$alkyl)$_p$—N(R$^{6c}$)(R$^{6b}$) or —($C_{2-6}$alkenyl)—N(R$^{6c}$)(R$^{6b}$);

$R^6$ is —($C_{1-6}$alkyl)—R$^{6a}$, —($C_{2-6}$alkenyl)—R$^{6a}$, —($C_{1-6}$alkyl)$_p$—OR$^{6b}$, —($C_{2-6}$alkenyl)—OR$^{6b}$, —($C_{1-6}$alkyl)$_p$—SR$^{6b}$, —($C_{2-6}$alkenyl)—SR$^{6b}$, —($C_{1-6}$alkyl)$_p$—S(O)R$^{6b}$, —($C_{2-6}$alkenyl)—S(O)R$^{6b}$, —($C_{1-6}$alkyl)$_p$—S(O)$_2$R$^{6b}$ or —($C_{2-6}$alkenyl)—S(O)$_2$R$^{6b}$;

$R^7$ is hydrogen, halogen or $C_{2-6}$alkenyl;

$R^{6a}$ is $(Y^6)_5$ substituted phenyl, $(Y^6)_7$ substituted naphthyl, —C(O)NR$^{6c}$, or

where $A^6$ completes a substituted or unsubstituted 6-membered heterocycle, substituted or unsubstituted 5-membered heterocycle having fused thereto a $(Y^2)_{3or4}$ substituted benzene ring, or a substituted or unsubstituted 6-membered heterocycle having fused thereto a $(Y^2)_{3or4}$ substituted benzene ring (wherein said 6-membered heterocycles are selected from the group consisting of alpha-pyronyl, gamma-pyronyl, pyridinyl, pyridazinyl, pyrimidinyl, pyrazinyl and thiopyronyl, wherein said 5-membered heterocycles fused with a benzene ring are selected from the group consisting of benzofuran-2-yl, benzofuran-6-yl, benzothiophen-2-yl benzothiophen-5-yl, indol-2-yl, indol-5-yl, benzopyrazol-3-yl, benzopyrazol-5-yl, benzimidazol-2-yl, benzimidazol-5-yl, benzoxazol-2-yl and benzoxazol-5-yl, wherein said 6-membered heterocycles fused with a benzene ring are selected from the group consisting of quinolin-2-yl, quinolin-4-yl, quinolin-7-yl, isoquinolin-1-yl, isoquinolin-3-yl, isoquinolin-7-yl, cinnolin-3-yl and quinazolin-2-yl, and where the heterocycle substituents are selected from the group consisting of hydrogen, $C_{1-6}$alkyl, phenyl, halogen, —C(O)OH, —C(O)OC$_{1-6}$alkyl and —OC$_{1-6}$alkyl);

$R^{6b}$ is —($C_{1-6}$alkyl)$_p$—(($Y^6$)$_7$ substituted naphthyl), —($C_{1-6}$alkyl)$_p$—(($Y^6$)$_5$ substituted phenyl), —($C_{1-6}$alkyl)—C(O)N(R$^{6c}$)$_2$, —($C_{1-6}$alkyl)—C(O)OR$^{6c}$ or

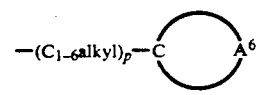

(where $A^6$ is defined immediately above);
$R^{6c}$ is hydrogen or $C_{1-6}$alkyl;
$Y^2$ is —H, halogen, —OH, $C_{1-6}$alkyl, —CN, —CF$_3$, —($C_{1-6}$alkyl)$_p$—O—$C_{1-6}$alkyl, —($C_{1-6}$alkyl)$_p$—S—$C_{1-6}$alkyl, —($C_{1-6}$alkyl)$_p$—S(O)—$C_{1-6}$alkyl, —($C_{1-6}$alkyl)$_p$—S(O)$_2$—$C_{1-6}$alkyl, —O—($C_{1-6}$alkyl)$_p$—C(O)OR$^{6c}$, —($C_{1-6}$alkyl)$_p$—C(O)OR$^{6c}$, —($C_{1-6}$alkyl)$_p$—C(O)NHOR$^{6c}$, —($C_{1-6}$alkyl)$_p$—C(O)NHR$^{6c}$, —($C_{1-6}$alkyl)$_p$—NHC(O)O($C_{1-6}$alkyl), —($C_{1-6}$alkyl)$_p$—NHS(O)$_2$—$C_{1-6}$alkyl, —($C_{1-6}$alkyl)$_p$—NHS(O)$_2$—(R$^7$)$_5$ substituted phenyl, or —(C$_{1-6}$alkyl)$_p$—NO$_2$;
Y$^6$ is Y$^2$ or

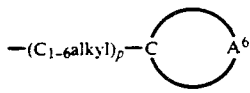

(where A$^6$ is defined immediately above); and
p is 0 or 1.

22. The leukotriene biosynthesis inhibitor of the formula:

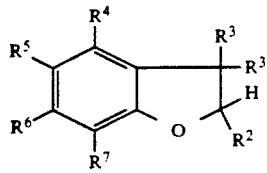

(I)

wherein
R$^2$ is —(C$_{1-6}$alkyl)—(Y$^6$)$_5$ substituted phenyl or —(C$_{2-6}$alkenyl)—(Y$^6$)$_5$ substituted phenyl;
R$^3$ is independently hydrogen or C$_{1-6}$alkyl;
R$^5$ is hydroxy or metabolizeable to hydroxy:
R$^4$ is hydrogen, halogen, —C$_{1-6}$alkyl, C$_{2-6}$alkenyl, —(C$_{1-6}$alkyl)—R$^{6a}$, —(C$_{2-6}$alkenyl)—R$^{6a}$, —(C$_{1-6}$alkyl)$_p$—OR$^{6b}$, —(C$_{2-6}$alkenyl)—OR$^{6b}$, —(C$_{1-6}$alkyl)$_p$—SR$^{6b}$, —(C$_{2-6}$alkenyl)—SR$^{6b}$, —(C$_{1-6}$alkyl)$_p$—S(O)R$^{6b}$, —(C$_{2-6}$alkenyl)—S(O)R$^{6b}$, —(C$_{1-6}$alkyl)$_p$—S(O)$_2$R$^{6b}$, —(C$_{2-6}$alkenyl)-S(O)$_2$R$^{6b}$, —(C$_{1-6}$alkyl)$_p$—N(R$^{6c}$)(R$^{6b}$) or —(C$_{2-6}$alkenyl)—N(R$^{6c}$)(R$^{6b}$);
R$^6$ is —(C$_{1-6}$alkyl)—R$^{6a}$, —(C$_{2-6}$alkenyl)—R$^{6a}$, —(C$_{1-6}$alkyl)$_p$—OR$^{6b}$, —(C$_{2-6}$alkenyl)—OR$^{6b}$, —(C$_{1-6}$alkyl)$_p$—SR$^{6b}$, —(C$_{2-6}$alkenyl)—SR$^{6b}$, —(C$_{1-6}$alkyl)$_p$—S(O)R$^{6b}$, —(C$_{2-6}$alkenyl)—S(O)R$^{6b}$, —(C$_{1-6}$alkyl)$_p$—S(O)$_2$R$^{6b}$ or —(C$_{2-6}$alkenyl)—S(O)$_2$R$^{6b}$;
R$^7$ is hydrogen or halogen;
R$^{6a}$ is (Y$^6$)$_5$ substituted phenyl, or

where A$^6$ completes substituted or unsubstituted 6-membered heterocycle, or a substituted or unsubstituted 6-membered heterocycle having fused thereto a (Y$^2$)$_{3or4}$ substituted benzene ring (wherein said 6-membered heterocycles are selected from the group consisting of alpha-pyronyl, gamma-pyronyl, pyridinyl, pyridazinyl, pyrimidinyl, pyrazinyl and thiopyronyl, wherein said 6-membered heterocycles fused with a benzene ring are selected from the group consisting of quinolin-2-yl, quinolin-4-yl, quinolin-7-yl, isoquinolin-1-yl, isoquinolin-3-yl, isoquinolin-7-yl, cinnolin-3-yl and quinazolin-2-yl, and where the heterocycle substituents are selected from the group consisting of hydrogen, C$_{1-6}$alkyl, phenyl, halogen, —C(O)OH, —C(O)OC$_{1-6}$alkyl and —OC$_{1-6}$alkyl);
R$^{6b}$ is —(C$_{1-6}$alkyl)$_p$—((Y$^6$)$_5$ substituted phenyl), —(C$_{1-6}$alkyl)—C(O)OR$^{6c}$, or

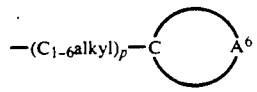

(where A$^6$ is defined immediately above);
R$^{6c}$ is hydrogen or C$_{1-6}$alkyl;
Y$^2$ is —H, halogen, —OH, C$_{1-6}$alkyl, —CN, —CF$_3$, —(C$_{1-6}$alkyl)$_p$—O—C$_{1-6}$alkyl, —(C$_{1-6}$alkyl)$_p$—S—C$_{1-6}$alkyl, —(C$_{1-6}$alkyl)$_p$—S(O)—C$_{1-6}$alkyl, —(C$_{1-6}$alkyl)$_p$—S(O)$_2$—C$_{1-6}$alkyl, —O—(C$_{1-6}$alkyl)$_p$—C(O)OR$^{6c}$, —(C$_{1-6}$alkyl)$_p$—C(O)OR$^{6c}$, —(C$_{1-6}$alkyl)$_p$—C(O)NHOH, —(C$_{1-6}$alkyl)$_p$—C(O)NHR$^{6c}$ or —(C$_{1-6}$alkyl)$_p$—NHS(O)$_2$—(R$^7$)$_5$ substituted phenyl;
Y$^6$ is Y$^2$ or

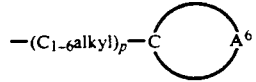

(where A$^6$ is defined immediately above); and
p is 0 or 1.

23. The leukotriene biosynthesis inhibitor of the formula:

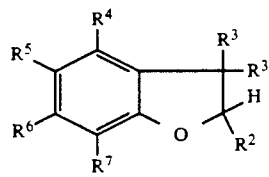

(I)

wherein
R$^2$ is —(C$_{1-6}$alkyl)—(Y$^6$)$_5$ substituted phenyl or —(C$_{2-6}$alkenyl)—(Y$^6$)$_5$ substituted phenyl;
R$^3$ is independently hydrogen or C$_{1-6}$alkyl;
R$^4$ is hydrogen, halogen, —C$_{1-6}$alkyl, C$_{2-6}$alkenyl, —(C$_{1-6}$alkyl)—R$^{6a}$, —(C$_{2-6}$alkenyl)—R$^{6a}$, —(C$_{1-6}$alkyl)$_p$—OR$^{6b}$, —(C$_{2-6}$alkenyl)—OR$^{6b}$, —(C$_{1-6}$alkyl)$_p$—SR$^{6b}$, —(C$_{2-6}$alkenyl)—SR$^{6b}$, —(C$_{1-6}$alkyl)$_p$—S(O)R$^{6b}$, —(C$_{2-6}$alkenyl)—S(O)R$^{6b}$, —(C$_{1-6}$alkyl)$_p$—S(O)$_2$R$^{6b}$, —(C$_{2-6}$alkenyl)-S(O)$_2$R$^{6b}$, —(C$_{1-6}$alkyl)$_p$—N(R$^{6c}$)(R$^{6b}$) or —(C$_{2-6}$alkenyl)—N(R$^{6c}$)(R$^{6b}$);
R$^5$ is hydrogen, —OC(O)—(C$_{1-6}$alkyl), —OC(O)O—(C$_{1-6}$alkyl), —OC(O)O—(phenyl), —OC(O)—(phenyl), —OSO$_3$NH$_4$, —OC(O)NR$_2$', —O(O)P(OH)$_2$ or —OC(O)—(C$_{1-6}$alkyl)—COOR' where R' is hydrogen, C$_{1-6}$alkyl or phenyl;
R$^6$ is —(C$_{1-6}$alkyl)—R$^{6a}$, —(C$_{2-6}$alkenyl)—R$^{6a}$, —(C$_{1-6}$alkyl)$_p$—OR$^{6b}$, —(C$_{2-6}$alkenyl)—OR$^{6b}$, —(C$_{1-6}$alkyl)$_p$—SR$^{6b}$, —(C$_{2-6}$alkenyl)—SR$^{6b}$, —(C$_{1-6}$alkyl)$_p$—S(O)R$^{6b}$, —(C$_{2-6}$alkenyl)—S(O)R$^{6b}$, —(C$_{1-6}$alkyl)$_p$—S(O)$_2$R$^{6b}$ or —(C$_{2-6}$alkenyl)—S(O)$_2$R$^{6b}$;
R$^{6a}$ is (Y$^6$)$_5$ substituted phenyl or

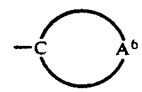

where A$^6$ completes substituted or unsubstituted 6-membered aromatic heterocycle (where the heterocycle contains 1 to 3 nitrogens the valences of which are satisfied by the ring and where the heterocycle substituents are selected from the group consisting of hydrogen, $C_{1-6}$alkyl, phenyl, halogen, —C(O)OH, —C(O)OC$_{1-6}$alkyl and —OC$_{1-6}$alkyl);

$R^{6b}$ is —(C$_{1-6}$alkyl)$_p$—((Y$^6$)$_5$ substituted phenyl) or

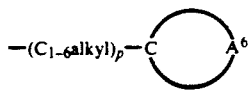

(where $A^6$ is defined immediately above); and
$R^{6c}$ is hydrogen or $C_{1-6}$alkyl;
$R^7$ is hydrogen or halogen;
$Y^2$ is —H, halogen, —OH, $C_{1-6}$alkyl, —CN, —CF$_3$, —(C$_{1-6}$alkyl)$_p$—O—C$_{1-6}$alkyl, —(C$_{1-6}$alkyl)$_p$—S—C$_{1-6}$alkyl, —(C$_{1-6}$alkyl)$_p$—S(O)—C$_{1-6}$alkyl, —(C$_{1-6}$alkyl)$_p$—S(O)$_2$—C$_{1-6}$alkyl, —O—(C$_{1-6}$alkyl)$_p$—C(O)OR$^{6c}$, —(C$_{1-6}$alkyl)$_p$—C(O)OR$^{6c}$, —(C$_{1-6}$alkyl)$_p$—C(O)NHOH, —(C$_{1-6}$alkyl)$_p$—C(O)NHR$^{6c}$ or —(C$_{1-6}$alkyl)$_p$—NHS(O)$_2$—(R$^7$)$_5$ substituted phenyl;

$Y^6$ is $Y^2$ or

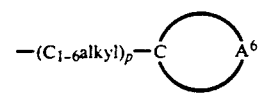

(where $A^6$ is defined immediately above); and
p is 0 or 1.

24. The leukotriene biosynthesis inhibitor of the formula:

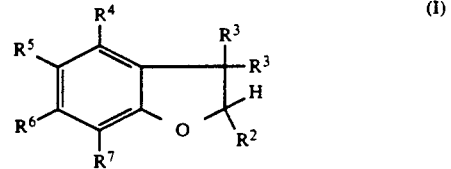

(I)

wherein $R^2$, $R^3$, $R^4$, $R^5$, $R^6$ and $R^7$ are selected from the group consisting of:

TABLE 1

| No. | —R$^2$ | —R$^3$/R$^3$ | —R$^4$ | —R$^5$ | —R$^6$ | —R$^7$ |
|---|---|---|---|---|---|---|
| 1 | CH$_2$Ph | Me/H | H | OH | OH | H |
| 2 | CH$_2$Ph-p-OMe | Me/H | Pr | OH | H | H |
| 4 | CH$_2$Ph-p-OH | Me/H | Pr | OH | H | H |
| 7 | CH$_2$Ph-p-F | Me/H | Pr | OH | H | H |
| 8 | CH$_2$Ph-p-OMe | Me/H | Pr | OAc | H | H |
| 9 | CH$_2$Ph-p-OMe | Me/H | Pr | OCO$_2$Me | H | H |
| 10 | CH$_2$Ph-p-OCH$_2$CO$_2$Et | Me/H | allyl | OH | H | H |
| 11 | CH$_2$Ph-p-OCH$_2$CO$_2$H | Me/H | allyl | OH | H | H |
| 12 | CH$_2$Ph-p-OMe | Me/H | H | OH | allyl | H |
| 13 | CH$_2$Ph-p-OMe | Me/H | H | OH | Pr | H |
| 14 | CH$_2$Ph-p-OMe | Me/H | H | OH | XOH | H |
| 17 | CH$_2$Ph-p-OMe | H/H | H | OH | allyl | H |
| 18 | CH$_2$Ph-p-OMe | Me/H | H | OH | CH$_2$CH$_2$CHCHPh-p-Cl | H |
| 19 | CH$_2$Ph-p-OMe | Me/H | H | OH | (CH$_2$)$_4$Ph-p-Cl | H |
| 20 | CH$_2$Ph-p-OMe | Me/Me | H | OH | allyl | H |
| 21 | CH$_2$Ph-p-OMe | Me/H | H | OH | X—OPh | H |
| 22 | CH$_2$Ph-p-OMe | Me/Me | H | OH | H | H |
| 23 | CH$_2$CH$_2$Ph-p-OMe | Me/Me | H | OH | allyl | H |
| 24 | CH$_2$CH$_2$Ph-p-Cl | Me/Me | H | OH | Pr | H |
| 25 | CH$_2$CH$_2$Ph-p-SMe | Me/Me | H | OH | Pr | H |
| 26 | CH$_2$CH$_2$Ph-p-SMe | Me/Me | H | OH | X—OH | H |
| 27 | CH$_2$CH$_2$Ph-p-SO$_2$Me | Me/Me | H | OH | Pr | H |
| 28 | CH$_2$CH$_2$Ph-p-SOMe | Me/Me | H | OH | Pr | H |
| 29 | CH$_2$CH$_2$Ph-p-Cl | H/H | H | OH | O—X-Ph | H |
| 30 | CH$_2$Ph-p-OMe | H/H | allyl | OH | H | H |
| 31 | CH$_2$CH$_2$Ph | Me/Me | H | OH | X—OPh | H |
| 33 | CH$_2$CH$_2$Ph-p-Cl | Me/Me | H | OH | X—OPh-p-Cl | H |
| 34 | CH$_2$CHCHPh-p-Cl | Me/Me | H | OH | SPh | H |
| 35 | CH$_2$CH$_2$Ph-p-Cl | H/H | H | OH | allyl | H |
| 36 | CH$_2$CH$_2$Ph-p-Cl | H/H | allyl | OH | H | H |
| 37 | CH$_2$CH$_2$Ph | Me/Me | H | OH | X—OH | H |
| 38 | CH$_2$CH$_2$Ph-p-Cl | Me/Me | H | OH | X—OPh-p-Cl | H |
| 39 | CH$_2$CH$_2$Ph-p-Cl | Me/Me | H | OH | X—OPh-p-Cl | H |
| 40 | CH$_2$CH$_2$Ph-p-Cl | Me/Me | H | OH | Pr | H |
| 41 | CH$_2$CH$_2$Ph-p-Cl | Me/Me | H | OH | t-butyl | H |
| 43 | CH$_2$CH$_2$Ph-p-Cl | H/H | H | OH | X—OH | H |
| 44 | CH$_2$CH$_2$Ph-p-Cl | Me/Me | H | OH | X—S-PYRID$^4$ | H |
| 45 | CH$_2$CH$_2$Ph-p-Cl | Me/Me | H | OH | X—S-PYRIM | H |
| 46 | CH$_2$CH$_2$Ph-p-Cl | Me/Me | H | OH | X—S—CH$_2$CH$_2$C(O)NMe$_2$ | H |
| 47 | CH$_2$CH$_2$Ph | H/H | Pr | OH | H | H |
| 48 | CH$_2$CH$_2$Ph | H/H | allyl | OH | H | H |
| 49 | CH$_2$CH$_2$Ph | H/H | H | OH | Pr | H |
| 50 | CH$_2$CH$_2$Ph | H/H | H | OH | allyl | H |
| 52 | CH$_2$CH$_2$Ph | H/H | H | OH | X—OPh | H |
| 53 | CH$_2$CH$_2$Ph | H/H | H | OH | CH$_2$-cyclopropyl | H |
| 57 | CH$_2$CH$_2$Ph-p-Cl | H/H | allyl | OH | allyl | H |
| 60 | CH$_2$CH$_2$Ph | H/H | H | OC(O)NMe$_2$ | X—OPh | H |
| 61 | X-Ph | H/H | H | OH | allyl | H |
| 62 | X-Ph | H/H | allyl | OH | H | H |
| 63 | CH$_2$CH$_2$Ph | H/H | H | OSO$_3$NH$_4$ | X—OPh | H |
| 64 | CH$_2$CH$_2$Ph | H/H | H | OH | X—S-PYRID$^4$ | H |
| 65 | CH$_2$CH$_2$Ph | H/H | H | OH | X—OPh-p-COOH | H |
| 66 | CH$_2$CH$_2$Ph | H/H | Pr | OH | X—OPh | H |

TABLE 1-continued

| No. | −R² | −R³/R³ | −R⁴ | −R⁵ | −R⁶ | −R⁷ |
|---|---|---|---|---|---|---|
| 67 | CH₂CH₂Ph | Me/Me | Pr | OH | X—OPh | H |
| 68 | CH₂CH₂Ph | H/H | H | O-β-glucuronide | X—OPh | H |
| 69 | CH₂CH₂Ph | H/H | Pr | OH | X—OPh-p-COOH | H |
| 70 | CH₂CH₂Ph | H/H | H | MeGLYC(O)O— | X—OPh | H |
| 71 | CH₂CH₂Ph | H/H | H | OH | X—OPh-p-TETR | H |
| 72 | CH₂CH₂Ph | H/H | H | OH | X—OPh-p-MTETR | H |
| 73 | CH₂CH₂Ph | H/H | H | OH | X—NMe₂ | H |
| 74 | CH₂CH₂Ph | H/H | H | OH | X—OPh-p-C(O)NH₂ | H |
| 75 | CH₂CH₂Ph | H/H | H | OH | CH₂CH₂C(CH₃)COOH | H |
| 76 | CH₂CH₂Ph | H/H | H | O(CH₂)₄COOMe | X—OPh | H |
| 77 | CH₂CH₂Ph | H/H | H | O(CH₂)₄COOH | X—OPh | H |
| 78 | CH₂CH₂Ph | H/H | H | OC(O)—S-PROL | X—OPh | H |
| 79 | CH₂CH₂Ph | H/H | H | OC(O)XCOOH | X—OPh | H |
| 80 | CH₂CH₂Ph | H/H | H | OH | X—OPh-p-CH₂COOH | H |
| 81 | CH₂CH₂Ph | H/H | H | OC(O)—S-PROL | X—OPh | H |
| 82 | CH₂CH₂Ph | H/H | H | OH | X—OPh-p-CMe₂COOH | H |
| 83 | CH₂CH₂Ph | H/H | H | OH | X—OPh-p-CHMeCOOH | H |
| 84 | CH₂CH₂Ph | H/H | H | OH | X—S-BENTHIA | H |
| 85 | CH₂CH₂Ph | H/H | H | OH | X—S-BENIMID | H |
| 86 | CH₂CH₂Ph | H/H | H | OH | X—OPh-o-TETR | H |
| 87 | CH₂CH₂Ph | H/H | H | OH | X—OPh-o-Me-p-TETR | H |
| 88 | CH₂CH₂Ph | H/H | H | OH | X—O-NAPT-1-TETR | H |
| 89 | CH₂CH₂Ph | H/H | H | OH | (CH₂)₄Ph | H |
| 90 | CH₂CH₂Ph | H/H | H | OH | X—OPh-p-C(O)NHOH | H |
| 91 | CH₂CH₂Ph | H/H | H | OH | X—OPh-o-Cl-p-TETR | H |
| 92 | CH₂CH₂Ph | H/H | Pr | OH | X—OPh-p-C(CH₃)₂-TETR | H |
| 93 | CH₂CH₂Ph | H/H | H | OH | X—OPh-p-C(CH₃)₂-TETR | H |
| 94 | CH₂CH₂Ph | H/H | X—OPh-p-TETR | OH | H | H |
| 95 | CH₂CH₂Ph | H/H | X—OPh-p-COOH | OH | H | H |
| 96 | CH₂CH₂Ph | H/H | X—S-PYRID⁴ | OH | H | H |
| 98 | CH₂CH₂Ph | H/H | H | OH | X—OPh-p-CH₂CH₂CMe₂COOH | H |
| 99 | CH₂CH₂Ph | H/H | Pr | OH | X—OPh-p-CH₂CH₂CMe₂COOH | H |
| 100 | CH₂CH₂Ph | H/H | Pr | OH | X—OPh-p-CH₂CH₂CMe₂COOH | H |
| 101 | CH₂CH₂Ph | H/H | H | OH | X—OPh-2-Pr-3-OH-4-Ac | H |
| 102 | CH₂CH₂Ph | H/H | H | OH | X—O-NAPT-6-TETR | H |
| 103 | CH₂CH₂Ph | H/H | H | OH | X—S-QUIN-6-COOMe | H |
| 104 | CH₂CH₂Ph | H/H | H | OH | X—S-QUIN-6-COOH | H |
| 105 | CH₂CH₂Ph | H/H | H | OH | X—S-QUINB-2-OMe-3-COOMe | H |
| 106 | CH₂CH₂Ph | H/H | H | OH | X—S-QUINB-2-OMe-3-COOH | H |
| 107 | CH₂CH₂Ph | H/H | H | OH | X—OPh-2,3-Cl-4-CMe₂COOH | H |
| 108 | CH₂CH₂Ph | H/H | H | OH | (CH₂)₄Ph-p-C(CH₃)₂COOH | H |
| 109 | CH₂CH₂Ph | H/H | H | OH | X—OPh-o-Ac-m-OH | H |
| 110 | CH₂CH₂Ph | H/H | H | OH | X—OPh-m-OH-p-Ac | H |
| 111 | CH₂CH₂Ph | H/H | H | OH | X—SPh-p-C(CH₃)₂COOH | H |
| 112 | CH₂CH₂Ph | H/H | H | OH | X—S-QUINB-2-t-bu-3-COOH | H |
| 113 | CH₂CH₂Ph | H/H | H | OH | X-QUINA-3-COOH | H |
| 114 | CH₂CH₂Ph | H/H | H | OH | X—OPh-p-TETR | H |
| 115 | CH₂CH₂Ph | H/H | H | OH | X—S-PYRID²-5-COOH | H |
| 116 | CH₂CH₂Ph | H/H | H | OH | X—S-QUINB-2-Ph-3-COOH | H |
| 117 | CH₂CH₂Ph | H/H | H | OH | CH₂Ph | H |
| 118 | CH₂CH₂Ph | H/H | H | OH | CH₂CH₂CHCHPh-p-CMe₂COOH | H |
| 119 | CH₂CH₂Ph | H/H | H | OH | CH₂Ph-2,4-Cl | H |
| 120 | CH₂CH₂Ph | H/H | H | OH | CH₂Ph-4-OMe | H |
| 121 | CH₂CH₂Ph | H/H | H | OH | CH₂Ph-4-Cl | H |
| 122 | CH₂CH₂Ph | H/H | H | OH | CH₂Ph-4-SMe | H |
| 123 | CH₂CH₂Ph | H/H | H | OH | CH₂Ph-3,5-Cl | H |
| 124 | CH₂CH₂Ph | H/H | H | OH | CH₂Ph-4-SO₂Me | H |
| 125 | CH₂CH₂Ph | H/H | H | OH | CH₂Ph-3,4-Cl | H |
| 126 | CH₂CH₂Ph | H/H | H | OH | CH₂Ph-4-NH₂.HCl | H |
| 127 | CH₂CH₂Ph | H/H | H | OH | CH₂Ph-4-NHSO₂Ph | |
| 128 | CH₂CH₂Ph | H/H | H | OH | CH₂Ph-4-NHC(O)CH₃ | H |
| 129 | CH₂CH₂Ph | H/H | H | OH | CH₂Ph-4-S-iPr | H |
| 130 | CH₂CH₂Ph | H/H | H | OH | CH₂Ph-4-SO₂-iPr | |
| 131 | CH₂CH₂Ph | H/H | H | OH | X—SO₂Ph | |
| 132 | CH₂CH₂Ph | H/H | H | OH | CH₂Ph-4-SO-Me | H |
| 133 | CH₂CH₂Ph | H/H | H | OH | CH₂Ph-2-OMe | H |
| 134 | CH₂CH₂Ph | H/H | H | OH | cis-CHCH-Ph | H |
| 135 | CH₂CH₂Ph | H/H | H | OH | trans-CHCH-Ph | H |
| 136 | CH₂CH₂Ph | H/H | H | OH | CH₂CH₂Ph | H |
| 137 | CH₂CH₂Ph | H/H | H | OH | X-Ph-4-SO₂Me | H |
| 138 | CH₂CH₂Ph | H/H | H | O(O)P(OH)₂ | X-Ph | H |
| 139 | CH₂CH₂Ph | H/H | H | OH | cis-CHCH-Ph-4-Cl | H |
| 140 | CH₂CH₂Ph | H/H | H | OH | trans-CHCH-Ph-4-Cl | H |
| 141 | CH₂CH₂Ph | H/H | H | OH | CH₂Ph-4-NHSO₂Me | H |
| 142 | CH₂CH₂Ph | H/H | H | OH | trans-CHCH-Ph-4-SO₂Me | H |
| 143 | CH₂CH₂Ph | H/H | H | OH | CH₂Ph-4-NO₂ | H |
| 144 | CH₂CH₂Ph | H/H | H | OH | trans-CHCH-Ph-4-OMe | |
| 145 | CH₂CH₂Ph | H/H | H | OH | CH₂CH₂Ph-4-OMe | H |
| 146 | CH₂Ph-p-OMe | Me/H | H | OH | X—O-Ph | H and |

TABLE 1-continued
| No. | -R² | -R³/R³ | -R⁴ | -R⁵ | -R⁶ | -R⁷ |
|-----|-----|--------|-----|-----|-----|-----|
| 147 | CH₂Ph-p-OMe | Me/H | H | OH | X—CH₂Ph-p-Cl | H; |
wherein:
$X = -CH_2CH_2CH_2-$; Ph = 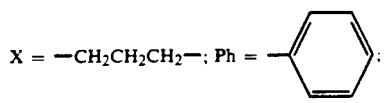
PYRID⁴ = 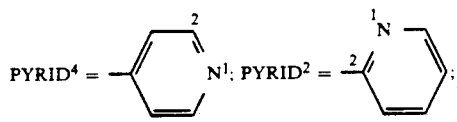; PYRID² = 
PYRIM = 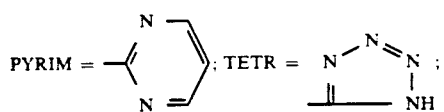; TETR = 
MTETR = 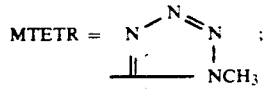
BENTHIA = 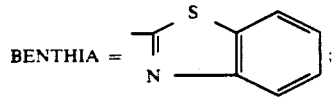
BENIMID = 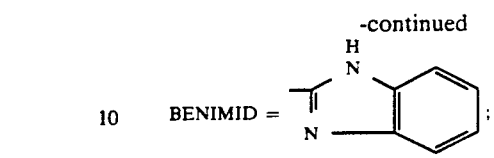
NAPT = 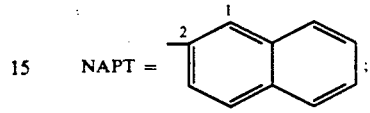
QUIN = 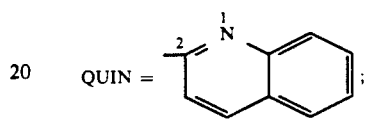
PROL = 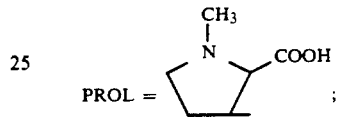
QUINA = 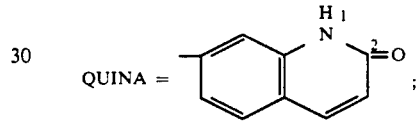
QUINB = 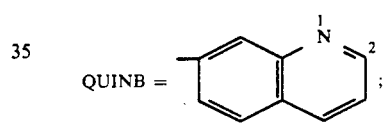
Me=methyl; Pr=propyl; Ac=—C(O)CH₃ and Et=ethyl.
* * * * *